(12) United States Patent
Rosselli et al.

(10) Patent No.: US 9,978,951 B2
(45) Date of Patent: May 22, 2018

(54) PERYLENE-BASED MATERIALS FOR ORGANIC PHOTOELECTRIC CONVERSION LAYERS

(71) Applicant: SONY CORPORATION, Tokyo (JP)

(72) Inventors: Silvia Rosselli, Mannheim (DE); Tzenka Miteva, Stuttgart (DE); Gabriele Nelles, Stuttgart (DE); Ameneh Bamedi Zilai, Stuttgart (DE); Vitor Deichmann, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 0 days. days.

(21) Appl. No.: 15/128,194

(22) PCT Filed: Mar. 20, 2015

(86) PCT No.: PCT/EP2015/055935
§ 371 (c)(1),
(2) Date: Sep. 22, 2016

(87) PCT Pub. No.: WO2015/150120
PCT Pub. Date: Oct. 8, 2015

(65) Prior Publication Data
US 2017/0104162 A1 Apr. 13, 2017

(30) Foreign Application Priority Data

Mar. 31, 2014 (EP) .................... 14162902

(51) Int. Cl.
*H01L 51/00* (2006.01)
*C07D 405/04* (2006.01)
(Continued)

(52) U.S. Cl.
CPC ........ *H01L 51/0062* (2013.01); *C07D 209/86* (2013.01); *C07D 221/18* (2013.01);
(Continued)

(58) Field of Classification Search
None
See application file for complete search history.

(56) References Cited

U.S. PATENT DOCUMENTS 6,491,749 B1 * 12/2002 Langhals ............. C07D 471/06
106/287.21
6,692,562 B2 * 2/2004 Schulz ..................... C09B 5/62
106/494

(Continued)

FOREIGN PATENT DOCUMENTS

EP 1 317 005 A2 6/2003
WO WO 2013/116569 A1 8/2013

OTHER PUBLICATIONS

Ramanan, Charusheela, et al. "Competition between Singlet Fission and Charge Separation in Solution-Processed Blend Films of 6,13-Bis(Triisopropylsilylethynyl)Pentacene with Sterically-Encumbered Perylene-3,4:9,10-Bis(Dicarboximide)s." Journal of the American Chemical Society, vol. 134, No. 1, Nov. 2012, pp. 386-397., doi:10.1021/ja2080482.*

(Continued)

*Primary Examiner* — Joseph Schoenholtz
(74) *Attorney, Agent, or Firm* — Oblon, McClelland, Maier & Neustadt, L.L.P.

(57) ABSTRACT

The present disclosure relates to perylene-based molecules and their use in photoelectric conversion layer(s) and/or an organic or hybrid image sensor. The present disclosure also relates to absorption layer(s) and photoelectric conversion layer(s) comprising a molecule according to the present disclosure. The present disclosure also relates to a device, comprising a photoelectric conversion layer comprising at least one perylene-based molecule. Moreover, the present disclosure relates to an organic image sensor or a hybrid (Continued)

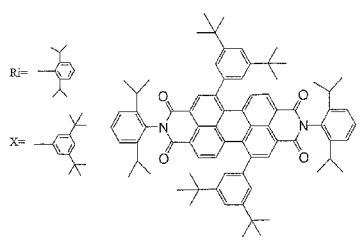

- Abs $\lambda_{max}$ = 561 nm
- PL $\lambda_{max}$ = 613 nm
- $T_{onset}$ ≈ 400 °C Silicon-organic image sensor comprising photoelectric conversion layer(s) according to the present disclosure.

19 Claims, 10 Drawing Sheets

(51) Int. Cl.
| | |
|---|---|
| *C07D 401/12* | (2006.01) |
| *C07D 401/10* | (2006.01) |
| *C07F 5/02* | (2006.01) |
| *C07D 471/06* | (2006.01) |
| *C07D 401/04* | (2006.01) |
| *C09K 11/06* | (2006.01) |
| *C09B 3/14* | (2006.01) |
| *C07D 209/86* | (2006.01) |
| *H01L 27/30* | (2006.01) |
| *C07D 421/14* | (2006.01) |
| *C07D 401/06* | (2006.01) |
| *C07D 421/04* | (2006.01) |
| *C07D 409/14* | (2006.01) |
| *C09B 5/62* | (2006.01) |
| *C07D 409/04* | (2006.01) |
| *C07D 221/18* | (2006.01) |

(52) U.S. Cl.
CPC ......... *C07D 401/04* (2013.01); *C07D 401/06* (2013.01); *C07D 401/10* (2013.01); *C07D 401/12* (2013.01); *C07D 405/04* (2013.01); *C07D 409/04* (2013.01); *C07D 409/14* (2013.01); *C07D 421/04* (2013.01); *C07D 421/14* (2013.01); *C07D 471/06* (2013.01); *C07F 5/025* (2013.01); *C09B 3/14* (2013.01); *C09B 5/62* (2013.01); *C09K 11/06* (2013.01); *H01L 51/0055* (2013.01); *H01L 51/0061* (2013.01); *H01L 51/0065* (2013.01); *H01L 51/0067* (2013.01); *H01L 51/0068* (2013.01); *H01L 51/0072* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *C09K 2211/1096* (2013.01); *H01L 27/307* (2013.01)

(56) References Cited

U.S. PATENT DOCUMENTS

| | | | |
|---|---|---|---|
| 7,307,297 B2 | 12/2007 | Okada et al. | |
| 7,671,202 B2 | 3/2010 | Marks et al. | |
| 2003/0118866 A1* | 6/2003 | Oh | H01L 51/0058 428/690 |
| 2009/0167167 A1* | 7/2009 | Aoyama | C07D 487/04 313/504 |
| 2011/0130566 A1* | 6/2011 | Yoon | C07D 409/14 546/37 |
| 2011/0286263 A1* | 11/2011 | Rosselli | B82Y 10/00 365/151 |
| 2013/0105768 A1 | 5/2013 | Leem et al. | |
| 2013/0181202 A1 | 7/2013 | Yofu et al. | |
| 2014/0042416 A1* | 2/2014 | Imai | H01L 27/307 257/40 |
| 2014/0239271 A1* | 8/2014 | Leem | H01L 51/442 257/40 |
| 2014/0239278 A1* | 8/2014 | Park | H01L 51/442 257/40 |
| 2014/0239284 A1* | 8/2014 | Yoshimura | C08K 3/04 257/40 |
| 2015/0041052 A1 | 2/2015 | Zhang et al. | |

OTHER PUBLICATIONS

Teraoka, Takuro, et al. "Iridium-Catalyzed Direct Tetraborylation of Perylene Bisimides." Organic Letters, vol. 13, No. 10, 2011, pp. 2532-2535., doi:10.1021/ol2004534.*

An, Zesheng, et al. "Synthesis and Photophysical Properties of Donor- and Acceptor-Substituted 1,7-Bis(Arylalkynyl)Perylene-3,4:9,10-Bis(Dicarboximide)s." The Journal of Physical Chemistry A, vol. 113, No. 19, 2009, pp. 5585-5593., doi:10.1021/jp900152r.*

Huang, Chun, et al. "Perylene-3,4,9,10-Tetracarboxylic Acid Diimides: Synthesis, Physical Properties, and Use in Organic Electronics." The Journal of Organic Chemistry, vol. 76, No. 8, 2011, pp. 2386-2407., doi:10.1021/jo200196.*

Lim, Seon-Jeong, et al. "Organic-on-Silicon Complementary Metal-Oxide-Semiconductor Colour Image Sensors." Scientific Reports, vol. 5, No. 1, Dec. 2015, doi:10.1038/srep07708.*

Seo, Hokuto, et al. "Color Sensors with Three Vertically Stacked Organic Photodetectors." Japanese Journal of Applied Physics, vol. 46, No. 49, 2007, doi:10.1143/jjap.46.l1240.*

Meiss, Jan, et al. "Tetrabutyl-Tetraphenyl-Diindenoperylene Derivatives as Alternative Green Donor in Bulk Heterojunction Organic Solar Cells." Solar Energy Materials and Solar Cells, vol. 95, No. 2, 2011, pp. 630-635., doi:10.1016/j.solmat.2010.09.030.*

Shibano, Yuki, et al. "Organic Thin-Film Solar Cells Using Electron-Donating Perylene Tetracarboxylic Acid Derivatives." The Journal of Physical Chemistry C, vol. 113, No. 34, 2009, pp. 15454-15466., doi:10.1021/jp9045726.*

Extended European Search Report dated Nov. 9, 2015 in Patent Application No. PCT/EP2015/055935.

Li Tan, et al., "Characterization of Organic p/n Junction Photodiodes Based on Poly(alkylthiophene)/Perylene Diimide Bilayers" Chemistry of Materials, May 9, 2003, 3 Pages.

Panagiotis E. Keivanidis, et al., "The Dependence of Device Dark Current on the Active-Layer Morphology of Solution-Processed Organic Photodetectors" Advanced Functional Materials, Sep. 3, 2010, 3 Pages.

\* cited by examiner

- Abs $\lambda_{max}$ = 561 nm
- PL $\lambda_{max}$ = 613 nm
- $T_{onset}$ ≈ 400 °C PMI 5 PhNMe2

- Abs $\lambda_{max}$ = 528 nm
- PL $\lambda_{max}$ = 643 nm
- $T_{onset}$ ≈ 400 °C

PERYLENE-BASED MATERIALS FOR ORGANIC PHOTOELECTRIC CONVERSION LAYERS

BACKGROUND

The field of the DISCLOSURE lies in molecules for organic image sensors and organic image sensor modules.

The present disclosure relates to perylene-based molecules and their use in photoelectric conversion layer(s) and/or an organic or hybrid image sensor.

The present disclosure also relates to absorption layer(s) and photoelectric conversion layer(s) including a molecule according to the present disclosure.

The present disclosure also relates to a device, including a photoelectric conversion layer including at least one perylene-based molecule.

Moreover, the present disclosure relates to an organic image sensor or a hybrid Silicon-organic image sensor including photoelectric conversion layer(s) according to the present disclosure.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Image sensors, which are semiconductor devices for converting an optical image into an electric signal, include a light-sensing unit for sensing light and a logic circuit unit for processing the sensed light into an electrical signal to store data.

In the state of the art, the light-sensing unit includes a color filter and a photoelectric conversion film, a semiconductor p-n junction, such as silicon. The color filter separates light according to colors, but reduces the spatial resolution and light collection and utilization efficiency.

In order to overcome this problem geometries are reported where photoelectric conversion units capable of detecting light of different wavelengths are stacked in a longitudinal direction. In particular such photoelectrical conversion unit is an organic photoelectric conversion layer based on p-n junction or bulk heterojunction. The photoelectric conversion efficiency of such a unit depends strongly on the type of material used in the layers. With the organic materials available so far, low conversion efficiencies and/or high dark currents are reported.

In another solution, an organic layer is used that is capable to absorb in the IR region but not in the visible region, that could be combined with a complementary metal oxide semiconductor (CMOS) based imager part for the visible range or with an organic based imager part that could absorb in the visible range. In both cases white light is collected and filter have to be used to get the BGR pixel resolution. In this case, as well as in the case of color filter, light is separated according to colors but the spatial resolution and light collection and utilization efficiency are reduced.

SUMMARY

The present disclosure provides a (perylene-based) molecule represented by a general formula selected from

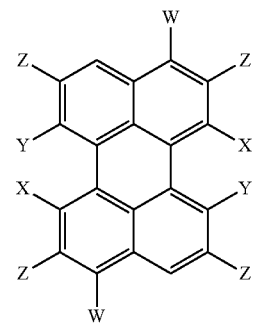

I

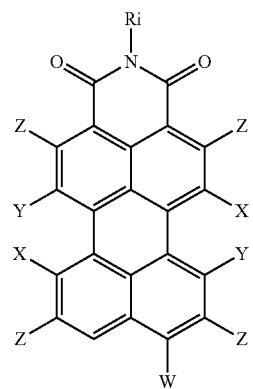

II

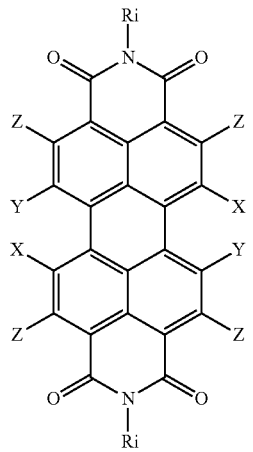

III wherein
X, and Y are the same or different and are, at each occurrence, independently selected from the following electron donating groups (EGD) and electron withdrawing groups (EWD):

hydrogen, halogen,

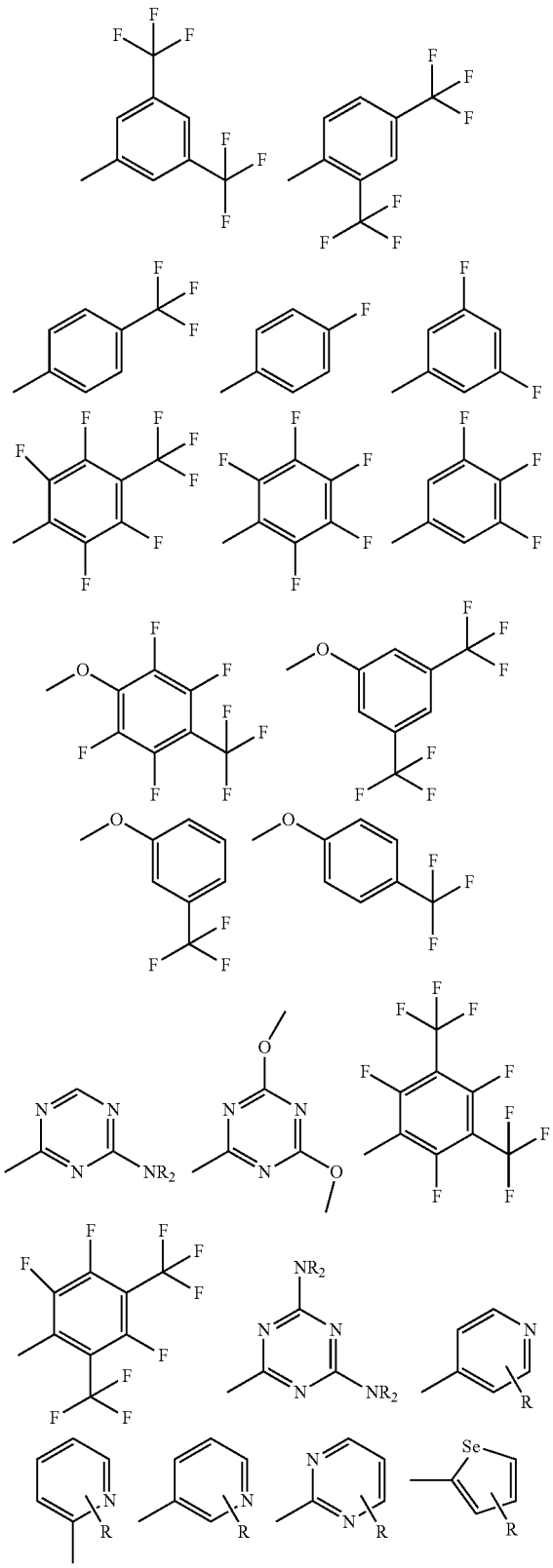

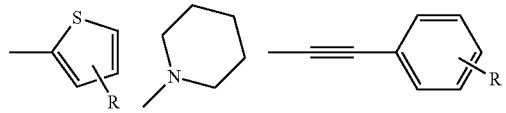

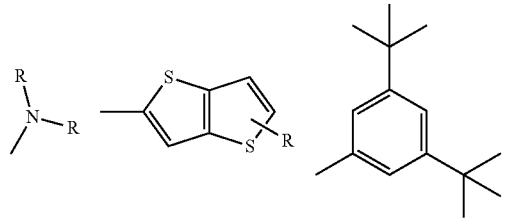

wherein R is independently selected from hydrogen, an alkyl or aryl substituent, Z, at each occurrence, is independently selected from the following electron donating groups (EGD) and electron accepting groups (EAD)

—OCH$_3$,

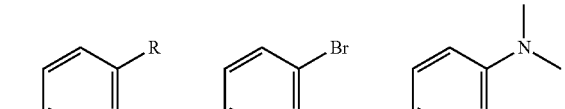

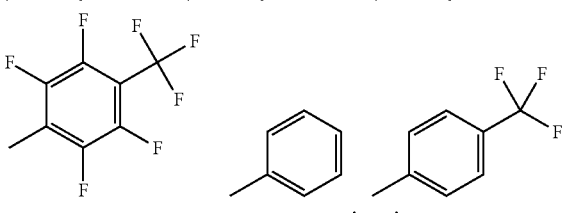

W, at each occurrence, is independently selected from the following electron donating groups (EGD) and electron withdrawing groups (EWD):

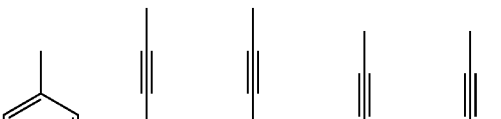

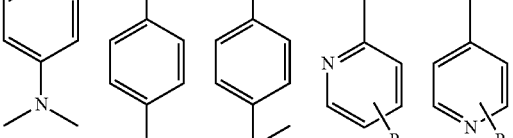

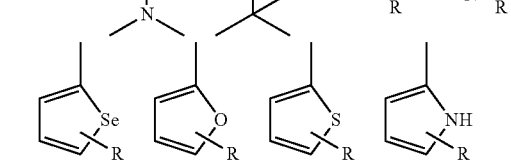

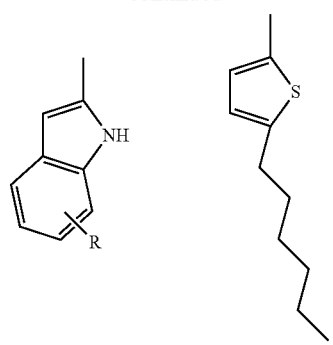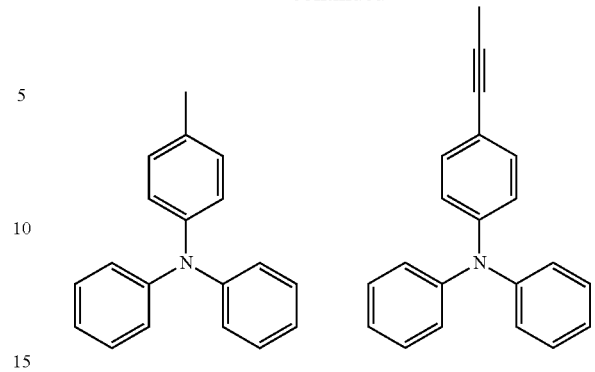

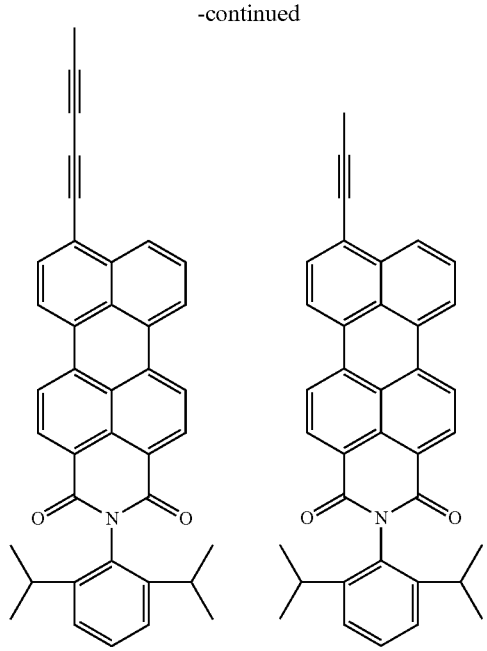
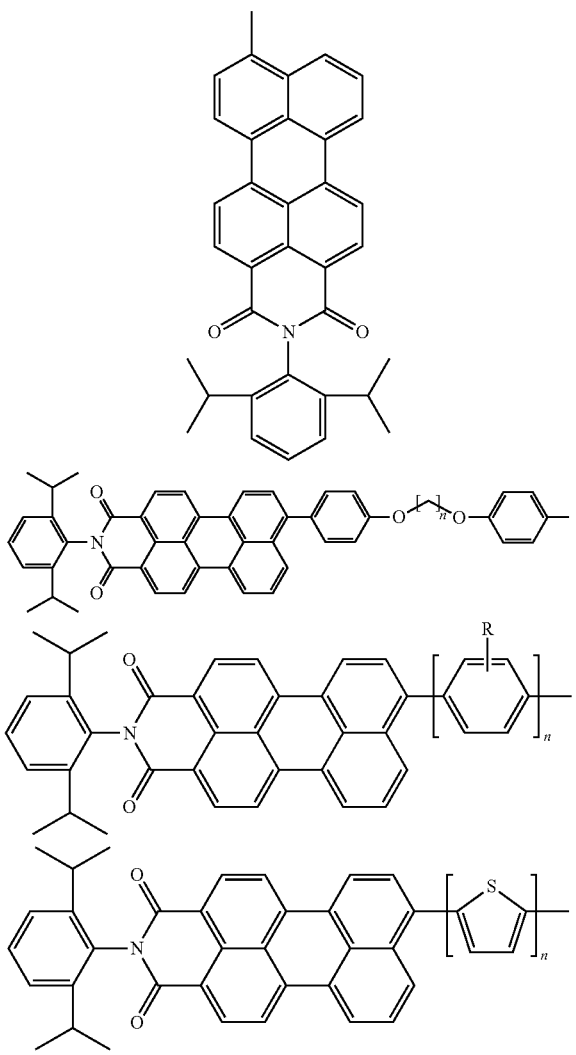
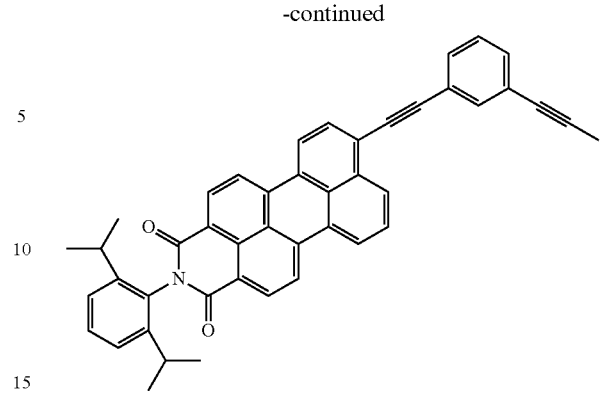
wherein
R is independently selected from hydrogen, an alkyl or aryl substituent,
n is an integer selected from 1 to 10,
and
Ri, at each occurrence, is independently selected from
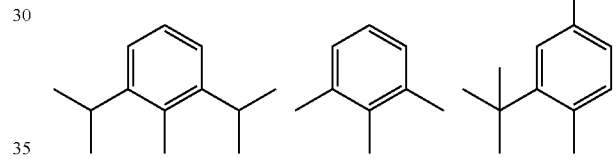
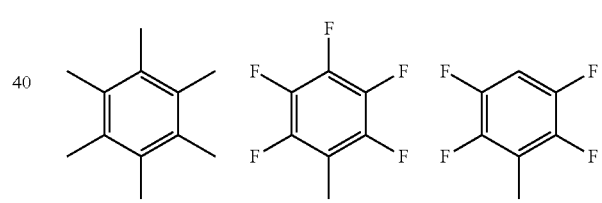
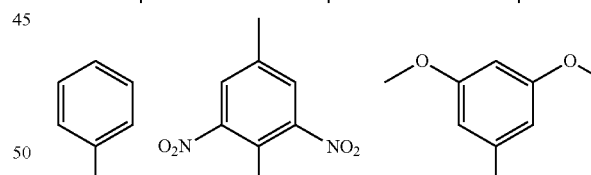
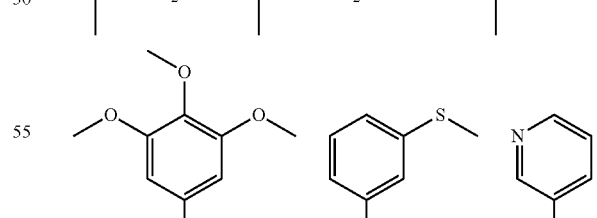
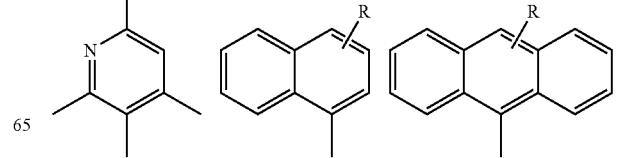

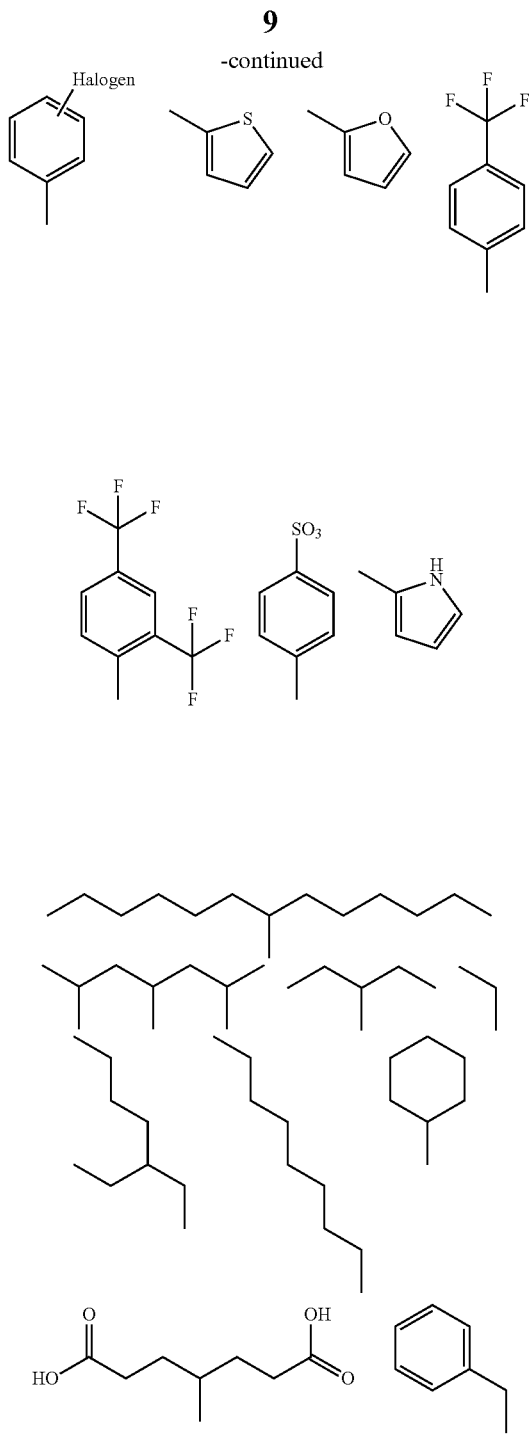
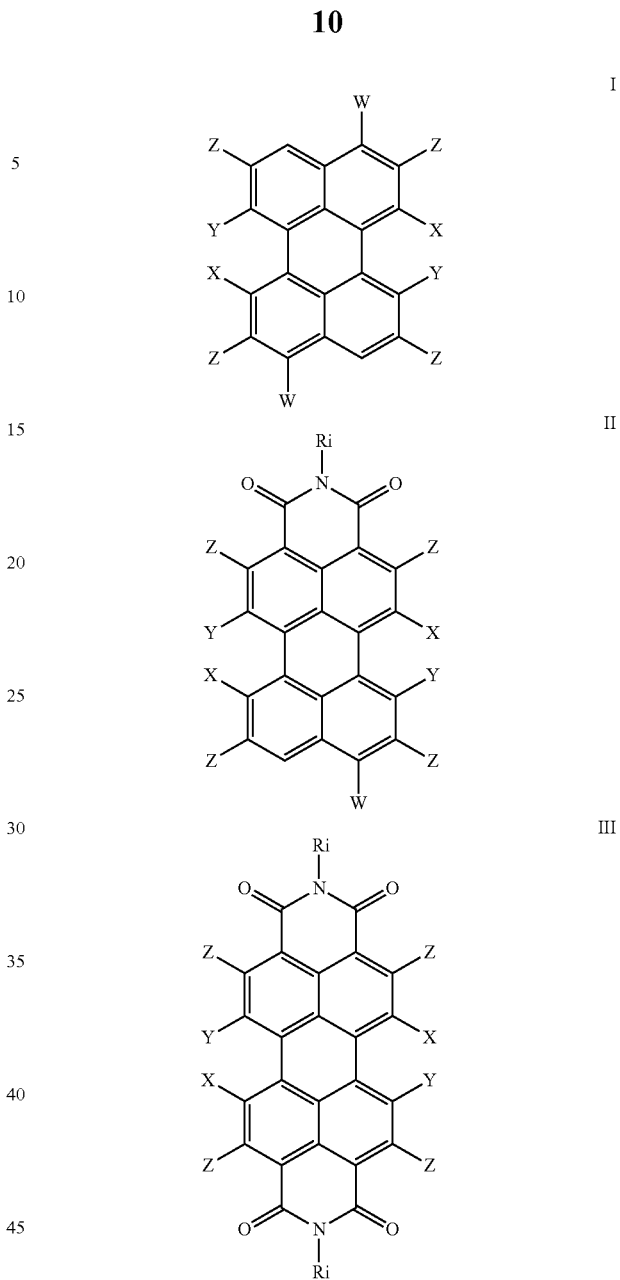

The present disclosure provides the use of a molecule according to the present disclosure in an absorption layer and/or in a photoelectric conversion layer and/or in an organic and/or hybrid module for optoelectronic application.

The present disclosure provides a photoelectric conversion layer including a molecule according to the present disclosure. The present disclosure provides an absorption layer including a molecule according to the present disclosure.

The present disclosure provides a device including a photoelectric conversion layer comprising at least one molecule represented by a general formula selected from wherein X, and Y are the same or different and are, at each occurrence, independently selected from H, electron donating groups (EGD) and electron withdrawing groups (EWD), Z, at each occurrence, is independently selected from H, electron donating groups (EGD) and electron accepting groups (EAD).

W, at each occurrence, is independently selected from H, electron donating groups (EGD) and electron withdrawing groups (EWD), Ri, at each occurrence, is independently selected from alkyl, cycloalkyl, aryl, fluoro-substituted aryl, heteroaryl, fluoro-substituted heteroaryl, halogen-substituted aryl, halogen-substituted heteroaryl.

The present disclosure provides an organic image sensor, including an organic photoelectric conversion unit including photoelectric conversion layer(s) according to the present disclosure.

The present disclosure provides a hybrid Silicon-organic image sensor, including an organic photoelectric conversion unit comprising photoelectric conversion layer(s) according to the present disclosure.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
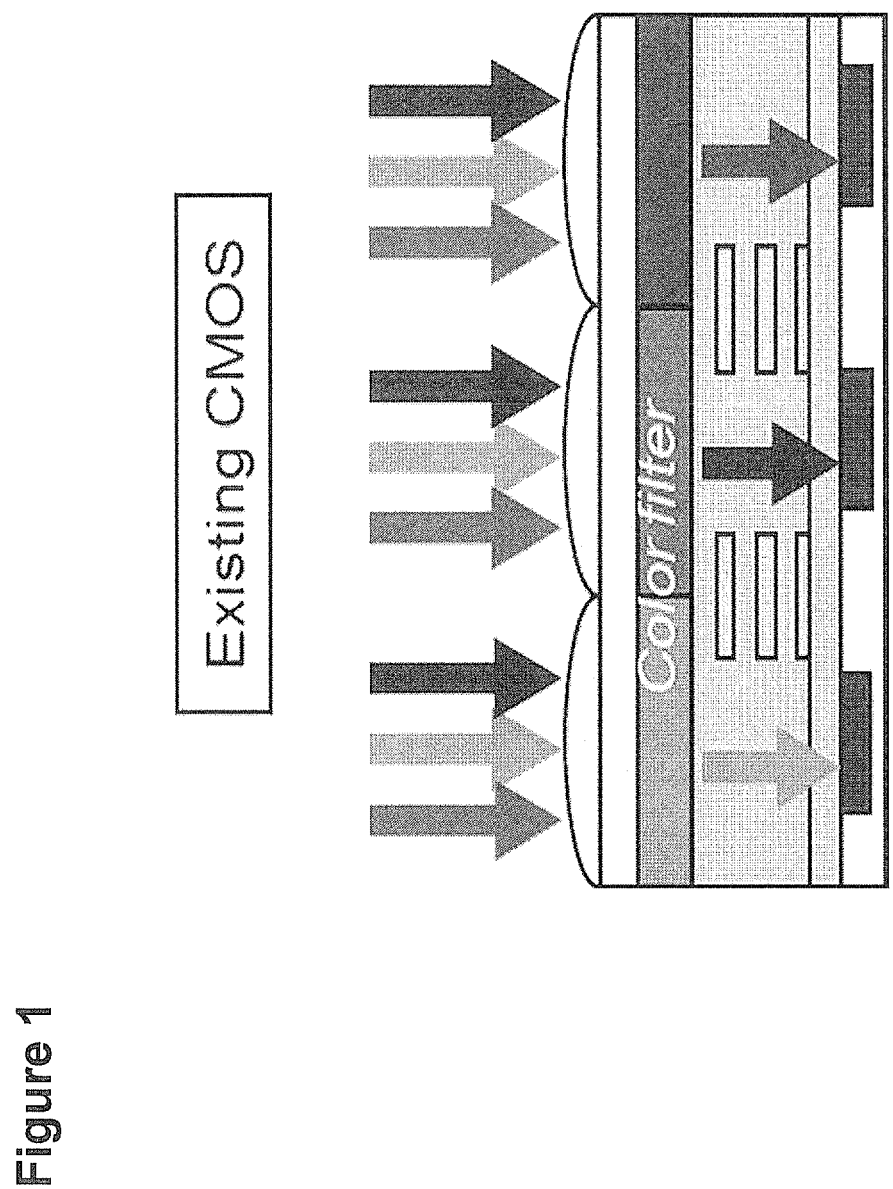
FIG. 1 shows a state of the art CMOS image sensor.

As discussed above, the present disclosure provides a perylene-based molecule represented by a general formula selected from

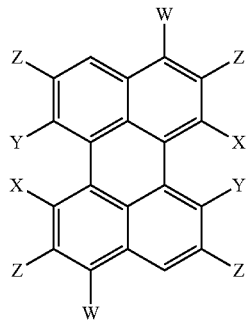

I

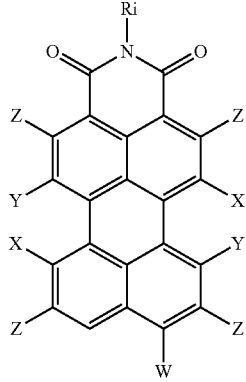

II

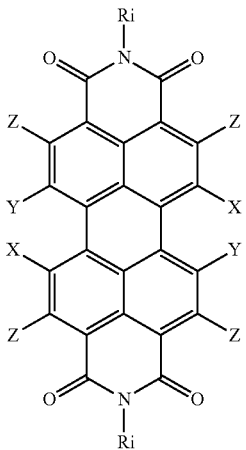

III

At the perylene core, substituents can be attached in the bay position (X. Y), ortho position (Z) and/or the pery position (W). Further substituents can be attached at the imide position (Ri).

The present disclosure provides a perylene-based molecule represented by a general formula selected from I, II or III, wherein X, and Y are the same or different and are at each occurrence, independently selected from the following electron donating groups (EGD) and electron withdrawing groups (EWD):

hydrogen, halogen,

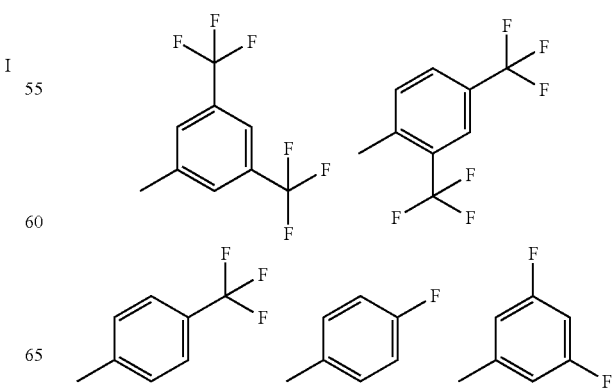

-continued
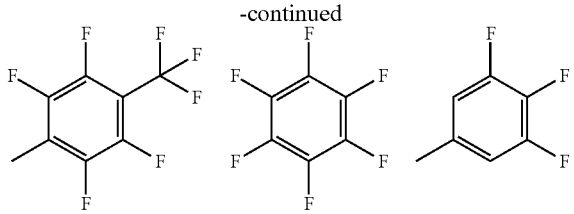
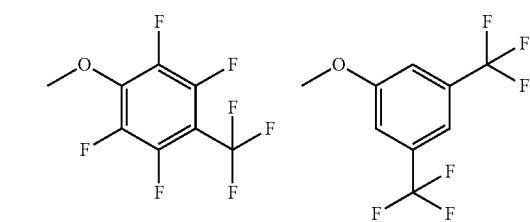
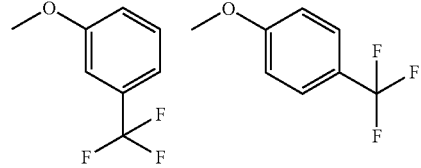
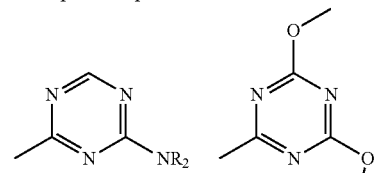
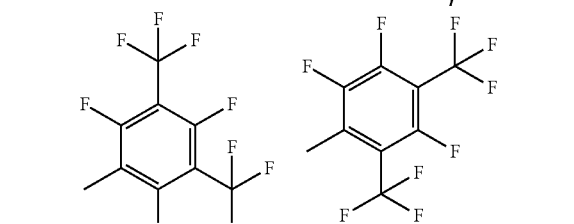
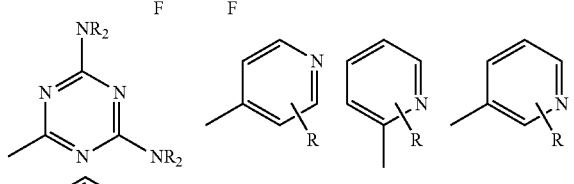
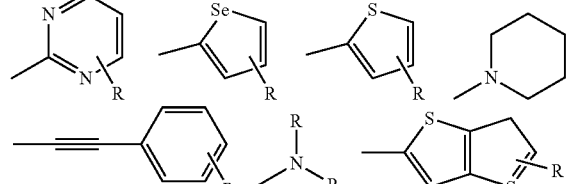
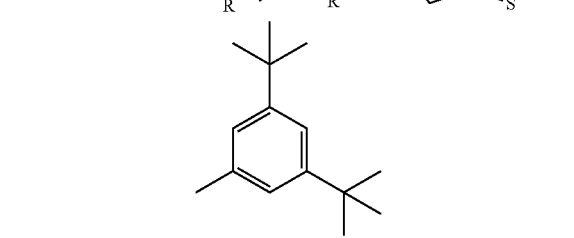
wherein R is independently selected from hydrogen, an alkyl or aryl substituent.
Z, at each occurrence, is independently selected from the following electron donating groups (EGD) and electron accepting groups (EAD)
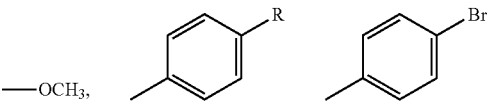
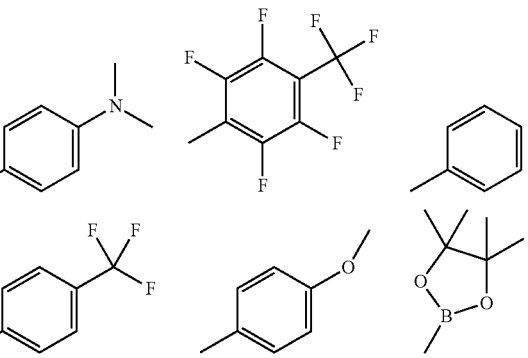
W, at each occurrence, is independently selected from the following electron donating groups (EGD) and electron withdrawing groups (EWD):
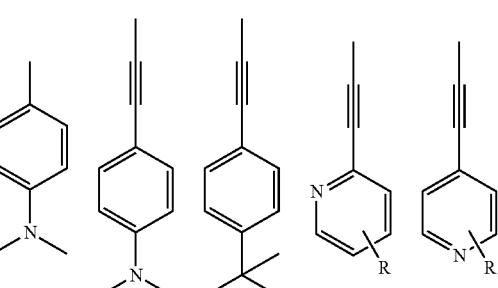
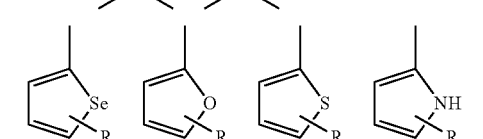
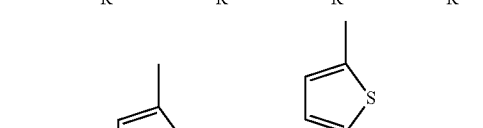
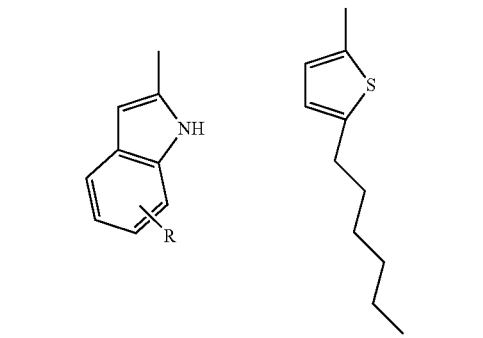

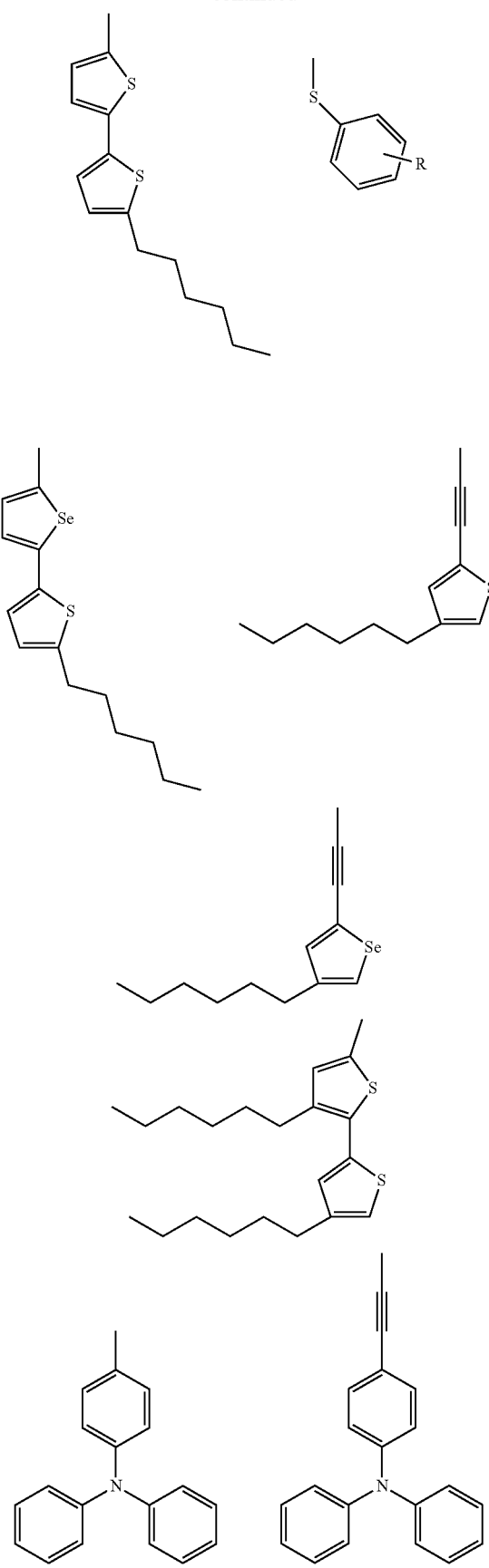
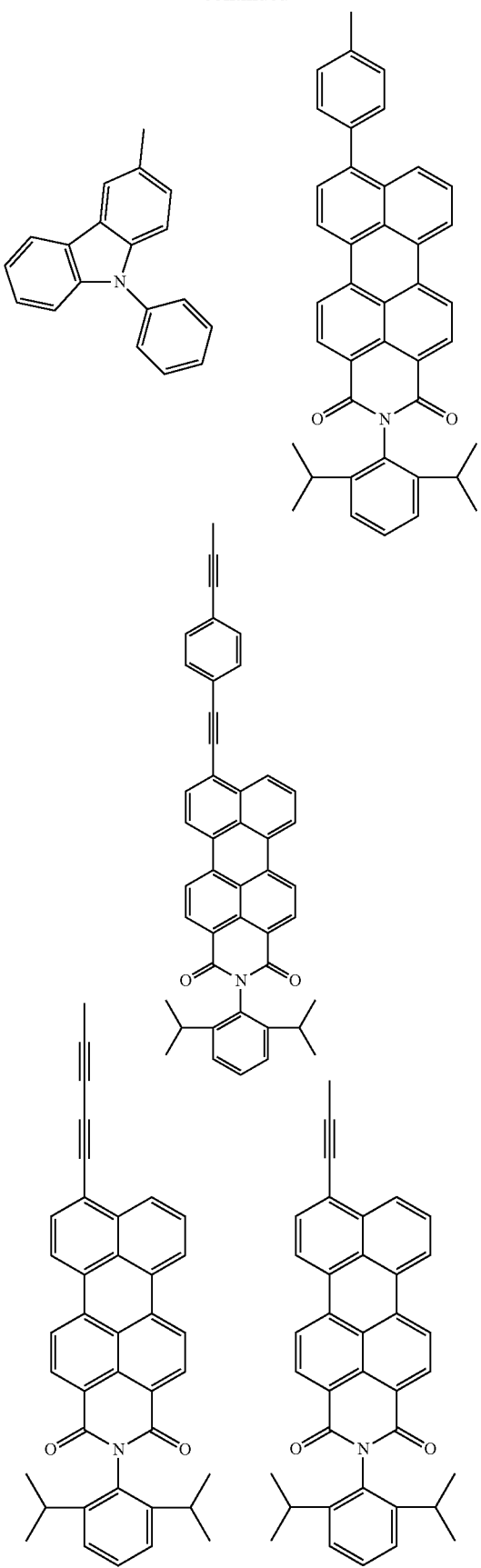

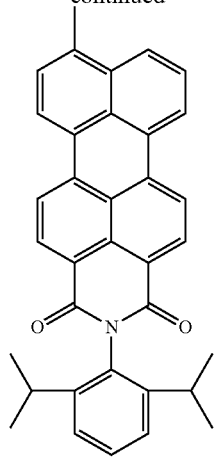
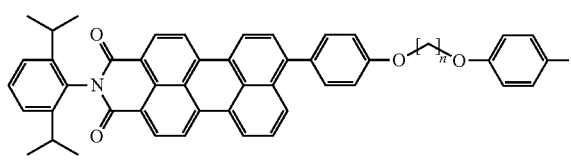
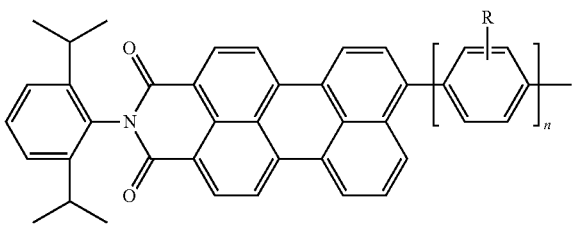
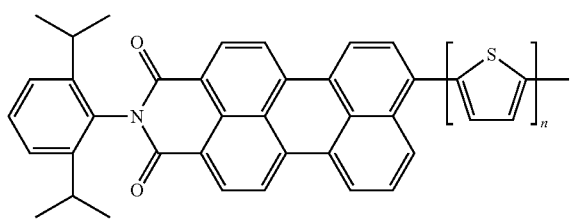
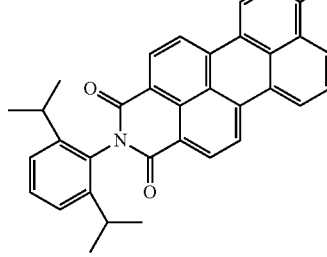
wherein
R is independently selected from hydrogen, an alkyl or aryl substituent,
n is an integer selected from 1 to 10,
and
Ri, at each occurrence, is independently selected from
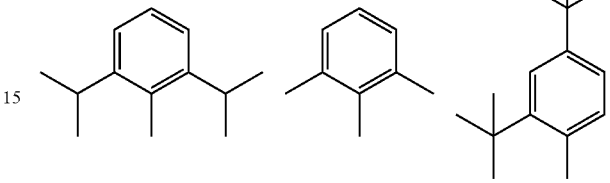
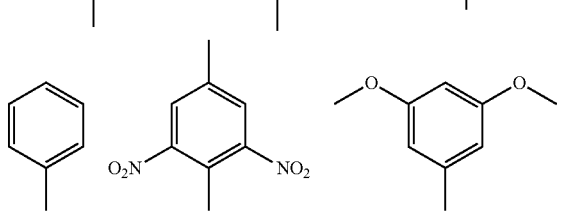
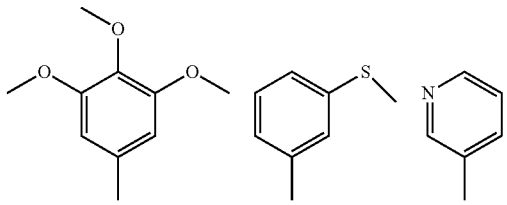
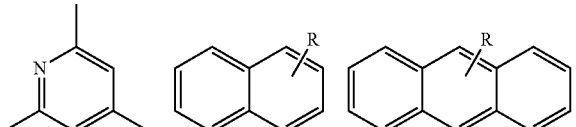
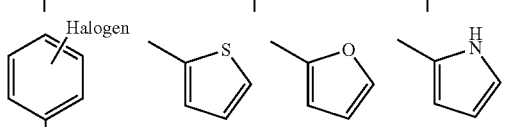
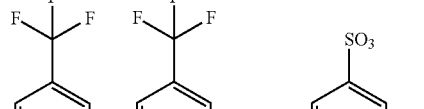
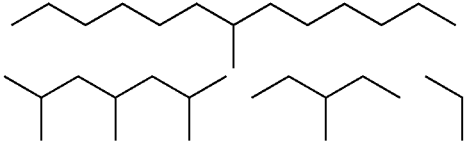

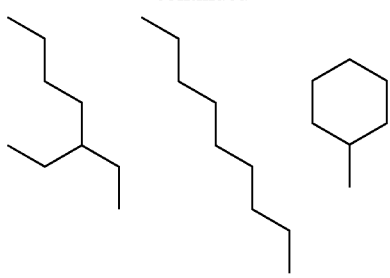

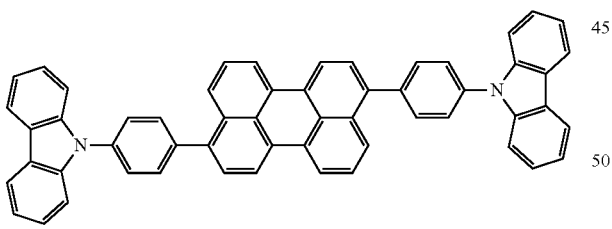

In a preferred embodiment, W, X, and Y are not cyano, nitro, quaternary amino, sulfo, carbonyl, substituted carbonyl, carboxy.

In a preferred embodiment, the molecule is represented by formula I, and

X, Y and Z are H, and

W is an electron donating group (EDG) as defined above.

In one embodiment, the molecule is represented by

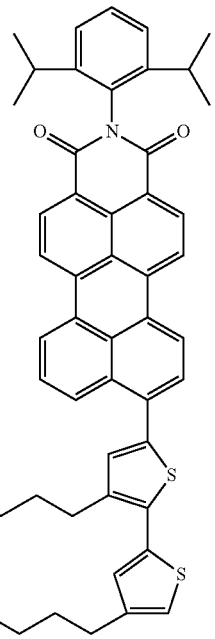

In a preferred embodiment, the molecule is represented by formula I, and

X, Y and Z are H, and

W is an electron withdrawing group (EWG) as defined above.

In a preferred embodiment, the molecule is represented by formula II and

Ri is as defined above,

X, Y and Z are H, and

W is an electron donating group (EDG) as defined above.

In one embodiment, the molecule is represented by any of structures

21
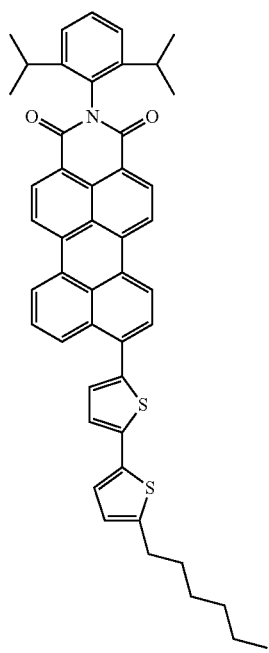
22
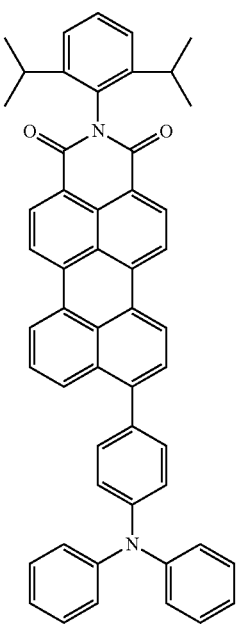 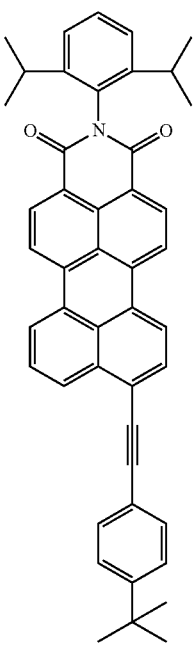
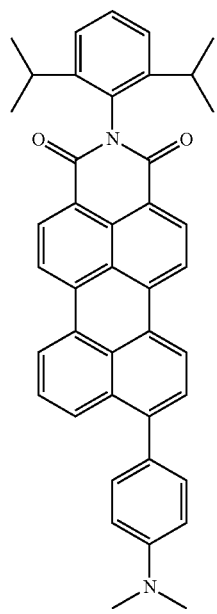 [SMILES: CC(C)c1cccc(C(C)C)c1N1C(=O)c2ccc3c4cccc5c(-c6ccc(N(C)C)cc6)ccc(c6ccc(c2c36)C1=O)c54] 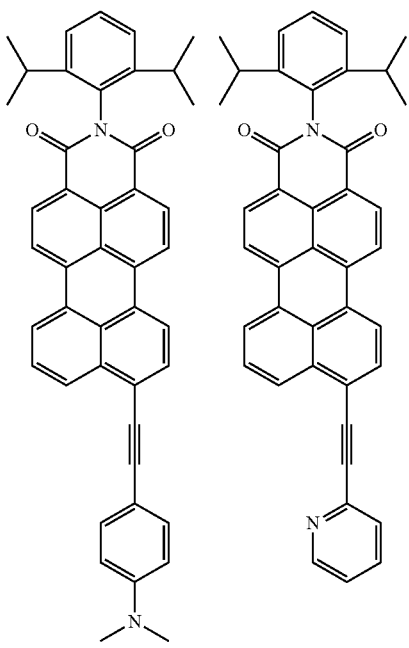

23
-continued
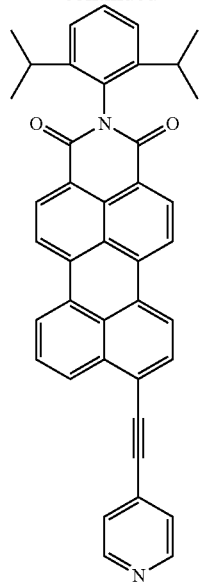
24
-continued
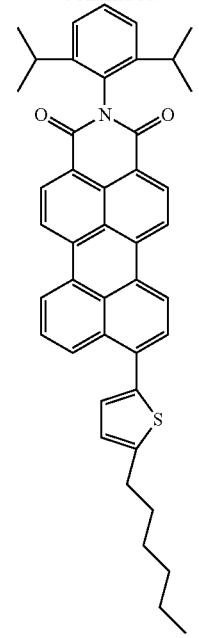
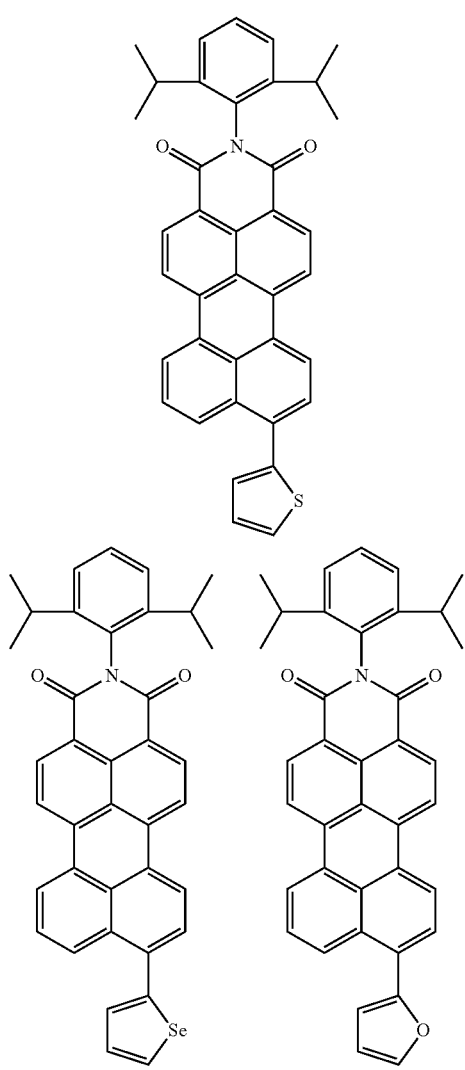
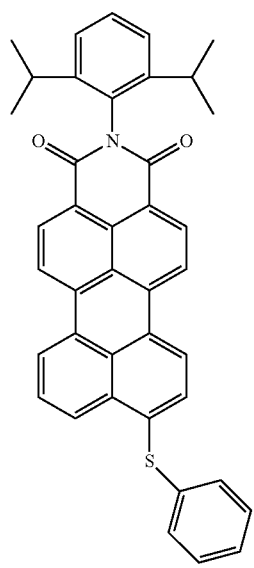
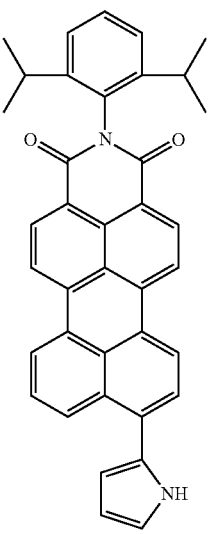 [SMILES: CC(C)c1cccc(C(C)C)c1N1C(=O)c2ccc3c4cccc5c(-c6cccs6)ccc(c6ccc(c2c36)C1=O)c54]

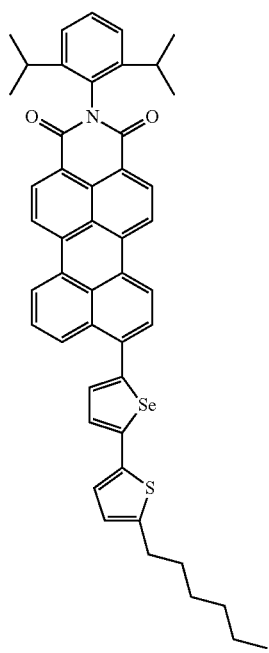 [SMILES: CCCCCCc1ccc(-c2ccc(-c3ccc4c5ccc6c7c(ccc(c8cccc3c84)c75)C(=O)N(c3c(C(C)C)cccc3C(C)C)C6=O)[se]2)s1]
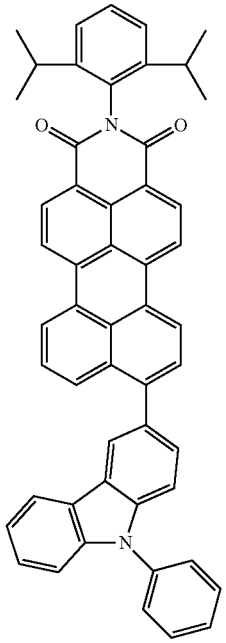
In a preferred embodiment, the molecule is represented by formula III and
R is as defined above.
X and Y are electron donating groups (EDG) as above, and Z is H.
In one embodiment, the molecule is represented by any of structures
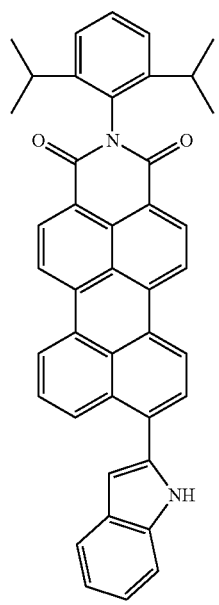
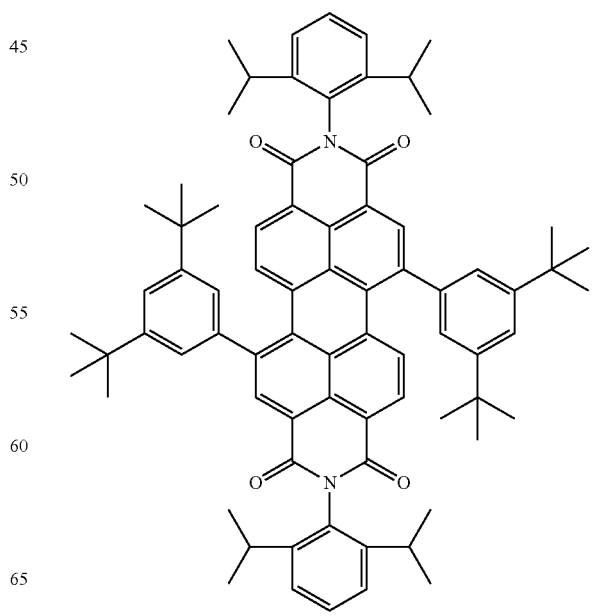

27
-continued
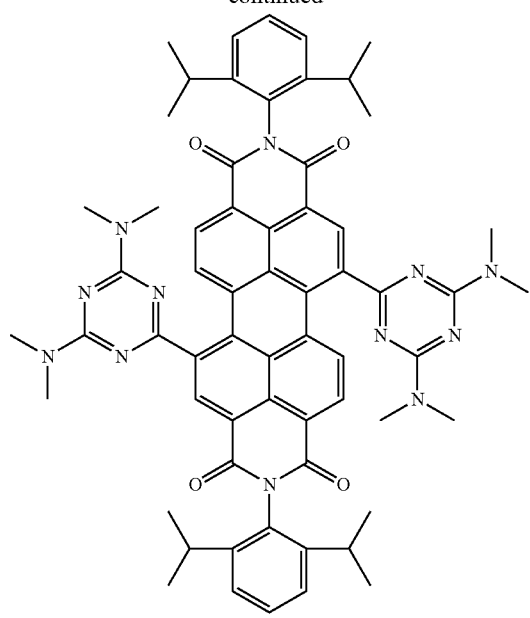
28
-continued
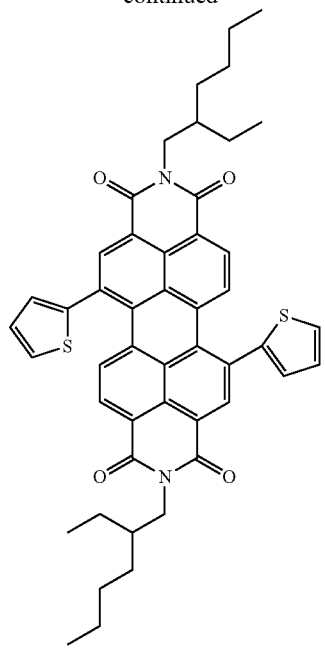
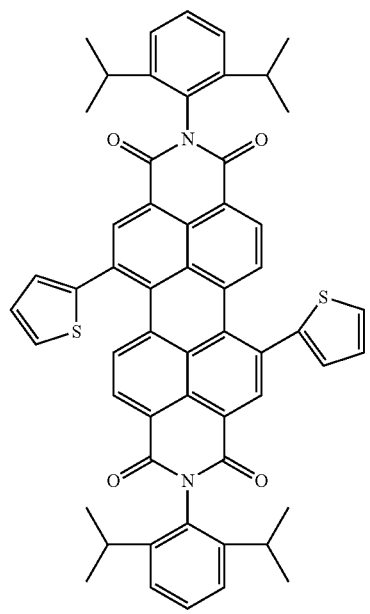
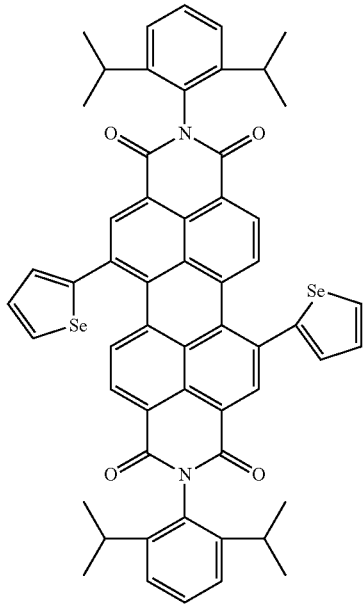

In a preferred embodiment, the molecule is represented by formula III and
R is as defined above,
X and Y are electron withdrawing group (EWG) as defined above, and
Z is H.

In one embodiment, the molecule is represented by any of structures

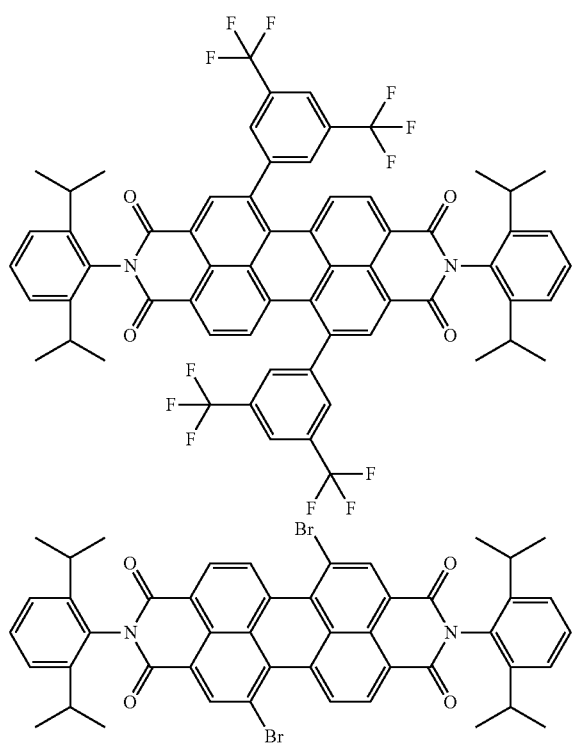

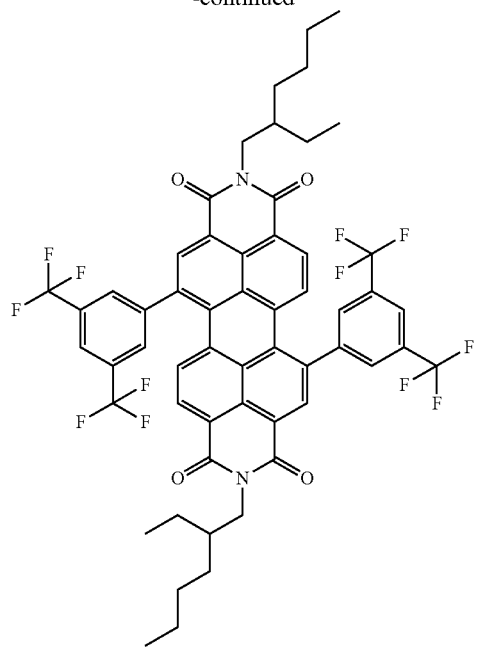

-continued

In a preferred embodiment, the molecule is represented by formula III and
Ri is as defined above,
X and Y are H, and
Z is an electron withdrawing and electron donating group (EWG and EDG).

In one embodiment, the molecule is represented by any of structures

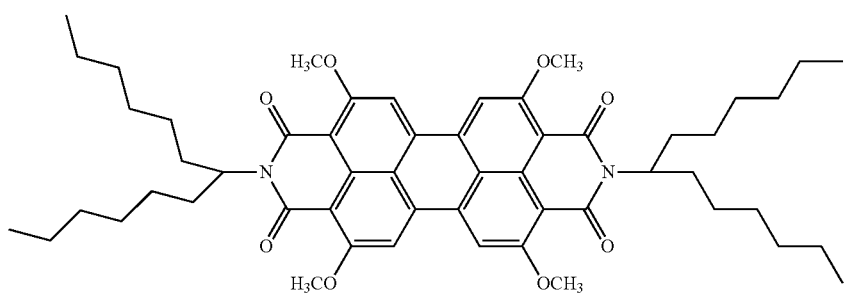

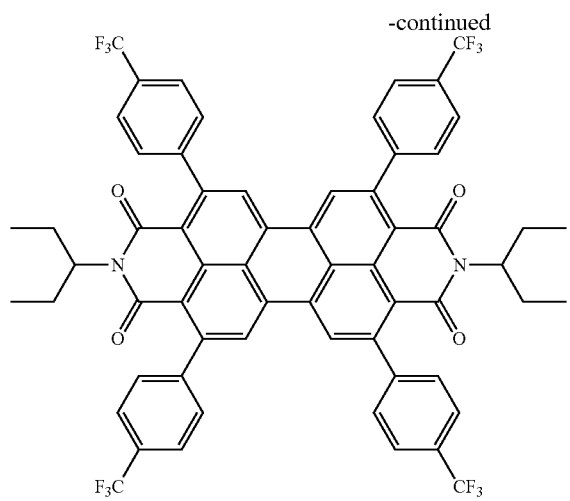
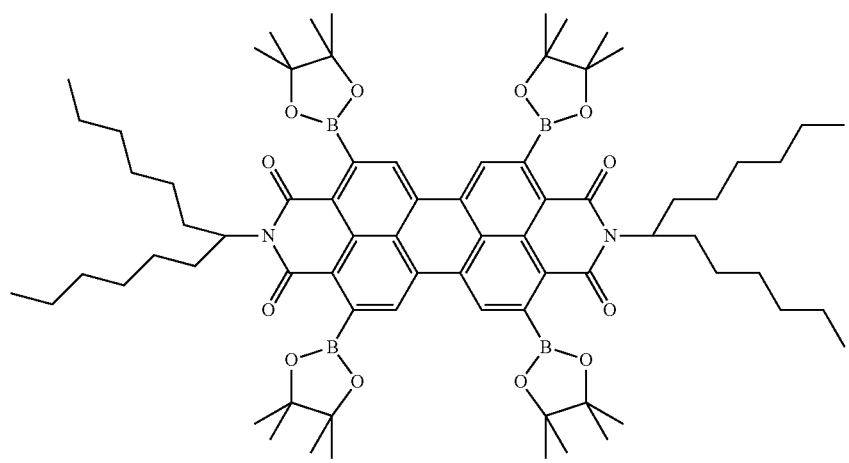
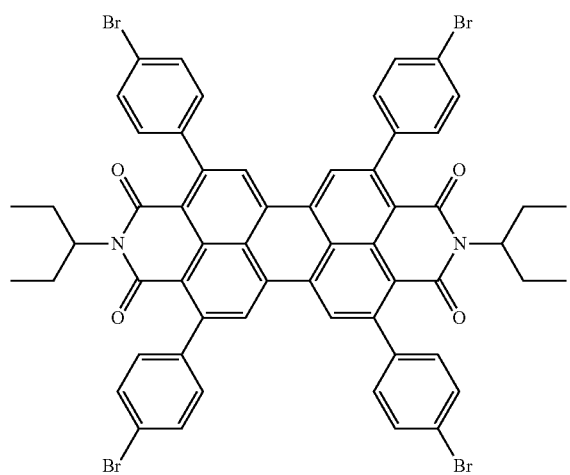 [SMILES: CCC(CC)N1C(=O)c2c(-c3ccc(Br)cc3)cc3c4cc(-c5ccc(Br)cc5)c5c6c(c(-c7ccc(Br)cc7)cc(c7cc(-c8ccc(Br)cc8)c(c2c37)C1=O)c64)C(=O)N(C(CC)CC)C5=O]

In a preferred embodiment, the molecule is represented by any of structures
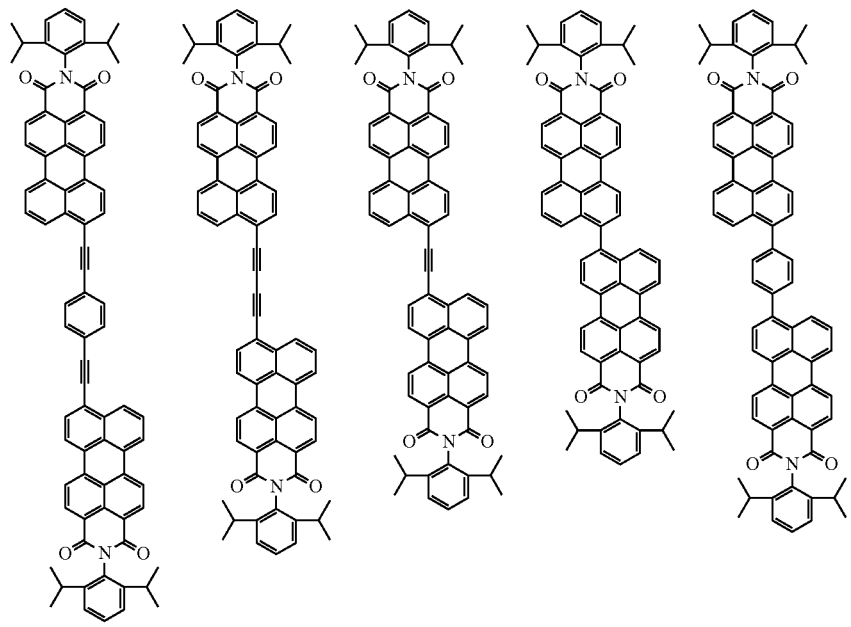
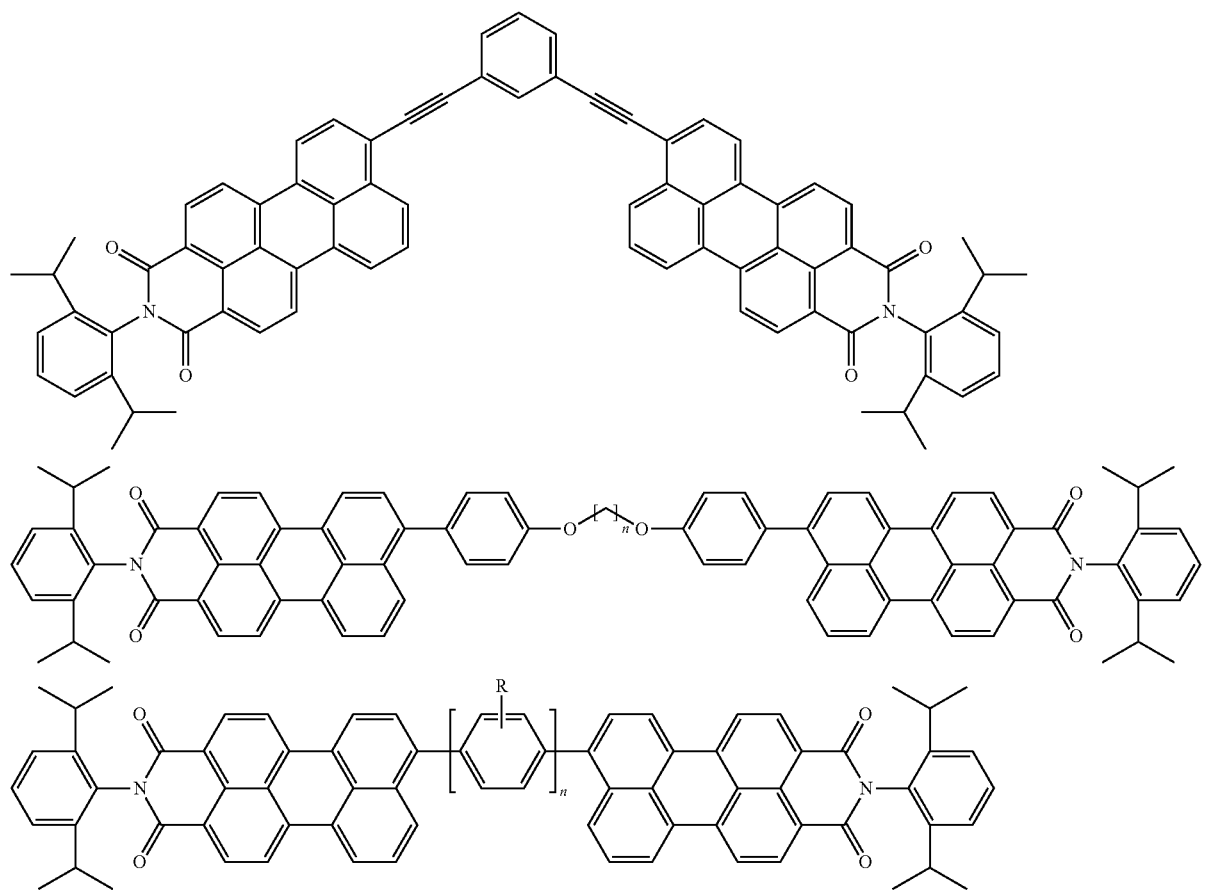

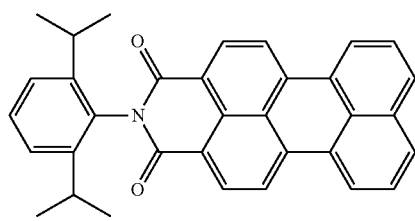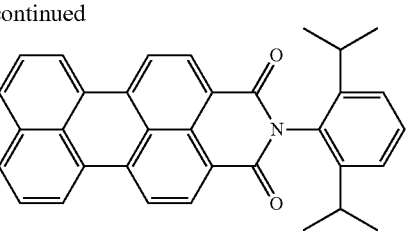

wherein

R is independently selected from hydrogen, an alkyl or alkyl substituent, n is an integer selected from 1 to 10.

A molecule according to the present disclosure is not one of the following:

N,N'-ditridecyl-3,4,9,10-perylene-tetracarboxylic-diimide;
(2,5-di-tert-butyl phenyl)-3,4,9,10-perylene dicarboximide;
diindenoperylene;
dibenzo{[f,f']-4,4',7,7'-tetraphenyl}diindeno[1,2,3-cd:1',2',3'-lm]perylene;
1,2-diaminobenzene perylene-3,4,9,10-tetracarboxylic acid diimide; or
N,N'-bis(1-ethylpropyl)-3,4,9,10-perylene tetracarboxylic diimide.

A molecule according to the present disclosure preferably exhibits absorption in the visible wavelength range (about 400 to about 700 nm) and possibly also absorption in the UV-Vis wavelength range (below 400 nm) and in the IR wavelength range (above 700 nm).

The molecules of the present disclosure absorb in the wavelength range of visible light, preferably in the range from 400 nm to 700 nm, or a sub-range thereof, preferably 400 nm to 500 nm, or 500 nm to 600 nm, or 600 nm to 700 nm.

In one embodiment, the molecules of the present disclosure absorb in the blue absorption range.

In one embodiment, the molecules of the present disclosure absorb in the green absorption range.

In one embodiment, the molecules of the present disclosure absorb in the red absorption range.

Preferably, the molecules absorb less than 20% (more preferably less than 5%) of the maximum absorption outside of their main range of absorption, such as, at wavelengths shorter than 500 and longer than 600 nm when absorption peak is between 0.500 and 600 nm.

A molecule according to the present disclosure preferably shows an extinction coefficient of $>10^4$ $Lmol^{-1}$ $cm^{-1}$.

A molecule according to the present disclosure preferably shows high thermal stability, preferably up to at least about 300° C. or up to at least about 300 to 500° C.

A molecule according to the present disclosure preferably allows furthermore:

easy alteration of HOMO and LUMO energies,
tuning of the absorbion maximum (optical band gap) and shape over a broad range.
tuning of the molecular packing in films.
Films prepared from the molecules of the present disclosure preferably show
high electrons and holes mobilities,
high exciton diffusion efficiencies,
more preferably up to 99%.
Preferably those films are homogeneous (on the nm to μm scale) and even more preferably amorphous.

As discussed above, the present disclosure provides the use of a molecule according to the present disclosure in an absorption layer or filter.

As discussed above, the present disclosure provides the use of a molecule according to the present disclosure in a photoelectric conversion layer and/or in an organic and/or hybrid module for optoelectronic application, such as image sensor, photodiode, organic photovoltaics, comprising organic photoelectric conversion layer(s), OLED and OTFT organic modules.

As discussed above, the present disclosure provides a photoelectric conversion layer comprising at least one molecule according to the present disclosure.

In one embodiment, the photoelectric conversion layer comprises further molecule(s).

As discussed above, the present disclosure provides an absorption layer or filter comprising at least one molecule according to the present disclosure.

Here the application of the molecule(s) of the present disclosure is as filter only, i.e. the films of molecules according to this disclosure are used only to absorb the light in the specific wavelength region (without to contribute to photoelectric conversion).

In one embodiment, the absorption layer or filter comprises further molecule(s).

Absorption layers according to the present disclosure preferably exhibits absorption in the visible wavelength range (about 400 to about 700 nm) and possibly also absorption in the UV-Vis wavelength range (below 400 nm) and in the IR wavelength range (above 700 nm).

Absorption layers of the present disclosure absorb in the wavelength range of visible light, preferably in the range from 400 nm to 700 nm, or a sub-range thereof, preferably 400 nm to 500 nm, or 500 nm to 600 nm, or 600 nm to 700 nm.

In one embodiment, the absorption layers of the present disclosure absorb in the blue absorption range.

In one embodiment, the absorption layers of the present disclosure absorb in the green absorption range.

In one embodiment, the absorption layers of the present disclosure absorb in the red absorption range.

Preferably, the absorption layers absorb less than 20% (more preferably less than 5%) of the maximum absorption outside of their main range of absorption, such as, at wavelengths shorter than 500 and longer than 600 nm when absorption peak is between 500 and 600 nm.

In one embodiment, the photoelectric conversion layer and/or the absorption layer comprises further n and/or p type materials (molecules) that can be used together with the perylene-based molecule(s) of the present disclosure, such as phthalocyanine-based (Pc), subphthalocyanine-based (SubPc), merocyanine-based (MC), diketopyrrolopyrroles-based (DPP), borondipyrromethene-based (BO-DIPY), isoindigo-based (ID), and quinacridone-based (QD), fused acenes, such as pentacene-based and tetracene-based, thiophene-based, selenophene-based, and triphenylamine-based (TPA) molecules.

In a preferred embodiment, said photoelectric (PE) conversion a exhibits photo response in the visible absorption range.

The PE conversion layers according to the present disclosure preferably exhibits absorption in the visible wavelength range (about 400 to about 700 nm) and possibly also absorption in the UV-Vis wavelength range (below 400 nm) and in the IR wavelength range (above 700 nm).

The PE conversion layers of the present disclosure absorb in the wavelength range of visible light, preferably in the range from 400 nm to 700 nm, or a sub-range thereof, preferably 400 nm to 500 nm, or 500 nm to 600 nm, or 600 nm to 700 nm.

In one embodiment, the PE layers of the present disclosure absorb in the blue absorption range (e.g. 400-500 nm).

In one embodiment, the molecules of the present disclosure absorb in the green absorption range (e.g. 500-600 nm).

In one embodiment, the molecules of the present disclosure absorb in the red absorption range (e.g. 600-700 nm).

Preferably, the PE layers absorb less than 20% (more preferably less than 5%) of the maximum absorption outside of their main range of absorption, such as, at wavelengths shorter than 500 and longer than 600 nm when absorption peak is between 500 and 600 nm.

As discussed above, the present disclosure provides a device comprising a photoelectric conversion layer comprising at least one molecule represented by a general formula selected from

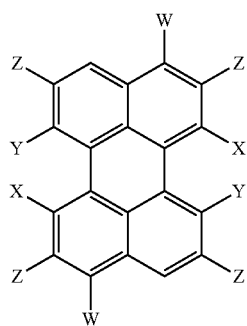

I

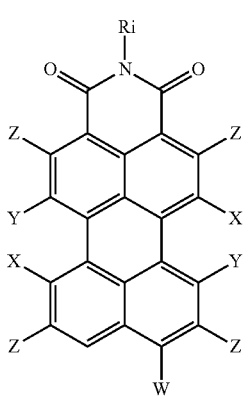

II

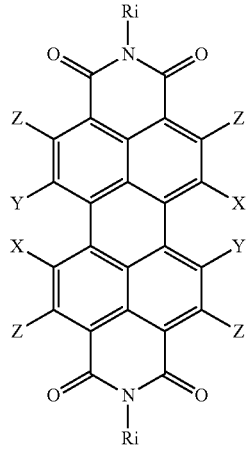

III wherein

X, and Y are the same or different and are, at each occurrence, independently selected from H, electron donating groups (EGD) and electron withdrawing groups (EWD), Z, at each occurrence, is independently selected from H, electron donating groups (EGD) and electron accepting groups (EAD), W, at each occurrence, is independently selected from H, electron donating groups (EGD) and electron withdrawing groups (EWD), R, at each occurrence, is independently selected from alkyl, cycloalkyl, aryl, fluoro-substituted aryl, heteroaryl, fluoro-substituted heteroaryl, halogen-substituted aryl, halogen-substituted heteroaryl, In a preferred embodiment, X, and Y are the same or different and are, at each occurrence, independently selected from H, electron donating groups (EGD) and electron withdrawing groups (EWD), which are preferably halogen, aryl, heteroaryl, substituted aryl, substituted heteroaryl, cycloalkyl, fluoro-substituted moieties such as fluoro-substituted aryl, heteroaryl), amino-substituted moieties (such as amino-substituted aryl, heteroaryl).

In a preferred embodiment, Z, at each occurrence, is independently selected from H, electron donating groups (EGD) and electron accepting groups (EAD), which are preferably carboxy, aryl, substituted aryl, fluoro-substituted moieties (such as fluoro-substituted aryl), amino-substituted moieties (such as amino-substituted aryl).

In a preferred embodiment, W, at each occurrence, is independently selected from H, electron donating groups (EGD) and electron withdrawing groups (EWD), which are preferably aryl, heteroaryl, substituted aryl, substituted heteroaryl, cycloakyl, alkyl-substituted moieties (such as alkyl-substituted aryl, heteroaryl), alkenyl-substituted moieties (such as alkenyl-substituted aryl, heteroaryl), alkynyl-substituted moieties (such as alkynyl-substituted aryl, heteroaryl).

In a preferred embodiment, not all of W, X, Y, and Z are H.

In a preferred embodiment, said device is an organic image sensor, an hybrid image sensor, photodiode, organic photovoltaics, organic light-emitting diode (OLED), organic thin-film transistor (OTFT).

In a preferred embodiment, said photoelectric conversion layer exhibits photo response in the visible absorption range.

In a preferred embodiment, the device according to the present disclosure does not comprise color filter(s).

In a preferred embodiment, the device according to the present disclosure comprises the perylene-based molecule(s) described above or a photoelectric conversion layer(s) comprising said molecule(s), as described above.

The devices according to the present disclosure preferably show (due to the utilization of the molecules):
high EQE
from high absorption efficiency,
high exciton diffusion efficiency,
high exciton dissociation efficiency,
high charge collection efficiency/high mobility.

The devices show also fast response time—preferably less than 1 ms even more preferred is <100 μs.

In one embodiment, the device according to the present disclosure comprises further molecule(s) in the photoelectric conversion layer(s).

In one embodiment, the photoelectric conversion layer comprises further n and p type materials that can be used together with the perylene-based molecule(s) of the present disclosure, such as
phthalocyanine-based (Pc), subphthalocyanine-based (SubPc), merocyanine-based (MC), diketopyrrolopyrroles-based (DPP), borondipyrromethene-based (BODIPY), isoindigo-based (ID), and quinacridone-based (QD), fused acenes, such as pentacene-based and tetracene-based, thiophene-based, selenophene-based, and triphenylamine-based (TPA) molecules.

A device according to the present disclosure does not comprise one of the following:
N,N'-ditridecyl-3,4,9,10-perylene-tetracarboxylic-diimide,
N,N'-bis (2,5-di-tert-butyl phenyl)-3,4,9,10-perylene dicarboximide, diindenoperylene,
dibenzo{[f,f']-4,4',7,7'-tetraphenyl}diindeno[1,2,3-cd:1',2',3'-lm]perylene,
1,2-diaminobenzene perylene-3,4,9,10-tetracarboxylic acid diimide, or
N,N'-bis(1-ethylpropyl)-3,4,9,10-perylene tetracarboxylic diimide.

As discussed above, the present disclosure provides an organic image sensor, comprising
(a) an organic photoelectric conversion unit comprising
photoelectric conversion layer(s) as defined above for the device of the present disclosure
and/or
photoelectric conversion layer(s) according to the present disclosure (comprising the perylene-based molecule(s) of the present disclosure),
(b) at least one electrode,
(c) a substrate,
(d) optionally, a second electrode on top of said photoelectric conversion layer(s), preferably not comprising color filter(s).

The substrate can be silicon, quartz, glass, polymer, such as PMMA, PC, PS, COP, COP, PVA, PVP, PES, PET, PEN, mica, or combinations thereof.

The substrate can also be other photoelectric conversion unit(s) (e.g. blue 400-500 nm and red 600-500 nm conversion devices in case the organic conversion layer according to this disclosure is green 500-600 nm conversion device).

This means, a device of this disclosure can comprise i) two inorganic units with one organic unit, (ii) one inorganic unit with two organic units, or (iii) three organic units combined with each other in the organic image sensor. Any of the organic units can contain molecules/layers/devices according to this disclosure.

In a preferred embodiment, an organic image sensor consists of three organic conversion units containing molecules in layers as of this disclosure (in devices, each with transparent electrodes), combined with each other and operating each in one of the ranges 400 nm to 500 nm, 500 nm to 600 nm and 600 nm to 700 nm.

Combined units can be realized either by vertical and/or horizontal stacking of the organic-organic or organic-inorganic units.

The electrode material can be
transparent metal oxide, such as indium tin oxide (ITO), fluorine-doped indium oxide (IFO), tin oxide, fluorine-doped tin oxide (FTO), antimonium-doped tin oxide (ATO), zinc oxide (including Al, B and Ga doped zinc Oxide), indium oxide-zinc oxide (IZO), $TiO_2$,
non transparent or semitransparent metal or alloy or conductive polymer, such as Au, Ag, Cr, Ni, Pd, AlSiCu, or any metal or metal alloy or metal combination with suitable workfunction; PEDOT/PSS, PANI or PANI/PSS, graphene.

As discussed above, the present disclosure provides a hybrid Silicon-organic image sensor or organic image sensor, comprising
(a) an organic photoelectric conversion unit or units comprising
photoelectric conversion layer(s) as defined above for the device of the present disclosure
and/or
photoelectric conversion layer(s) according to the present disclosure (comprising the perylene-based molecule(s) of the present disclosure),
(b) optionally, a Si based photoelectric conversion unit,
(c) metal wiring,
(d) a (CMOS) substrate,
(e) insulating layer(s), preferably oxide.

In one embodiment, said organic photoelectric conversion unit of the image sensors of the present disclosure comprises different layers within the organic based photoelectrical conversion unit(s), such as
n-type material,
p-type material,
n-buffer layer,
p-buffer, layer,
or combinations and/or mixtures (e.g. n material and p material co-deposited in one layer) thereof.

For example, the organic image sensor of the present disclosure can have the structure:
substrate/first electrode/n-buffer layer/n-material/p-material/p buffer layer/second electrode;
substrate/first electrode/n-buffer layer/n-material/mixture of n- and p-material/p-material/p buffer layer/second electrode;
substrate/first electrode/n-buffer layer/n-material/mixture of n- and p-material/p buffer layer/second electrode;
substrate/first electrode/p-buffer layer/p-material/n-material/n buffer layer/second electrode.
substrate/first electrode/p-buffer layer/p-material/mixture of n- and p-material/n-material/n buffer layer/second electrode.
substrate/first electrode/p-buffer layer/p-material/mixture of n- and p-material/n buffer layer/second electrode.

The organic image sensor of the present disclosure can comprise different layer structures, in particular regarding the position of the n and p material with respect to the CMOS part.

Figure 2:
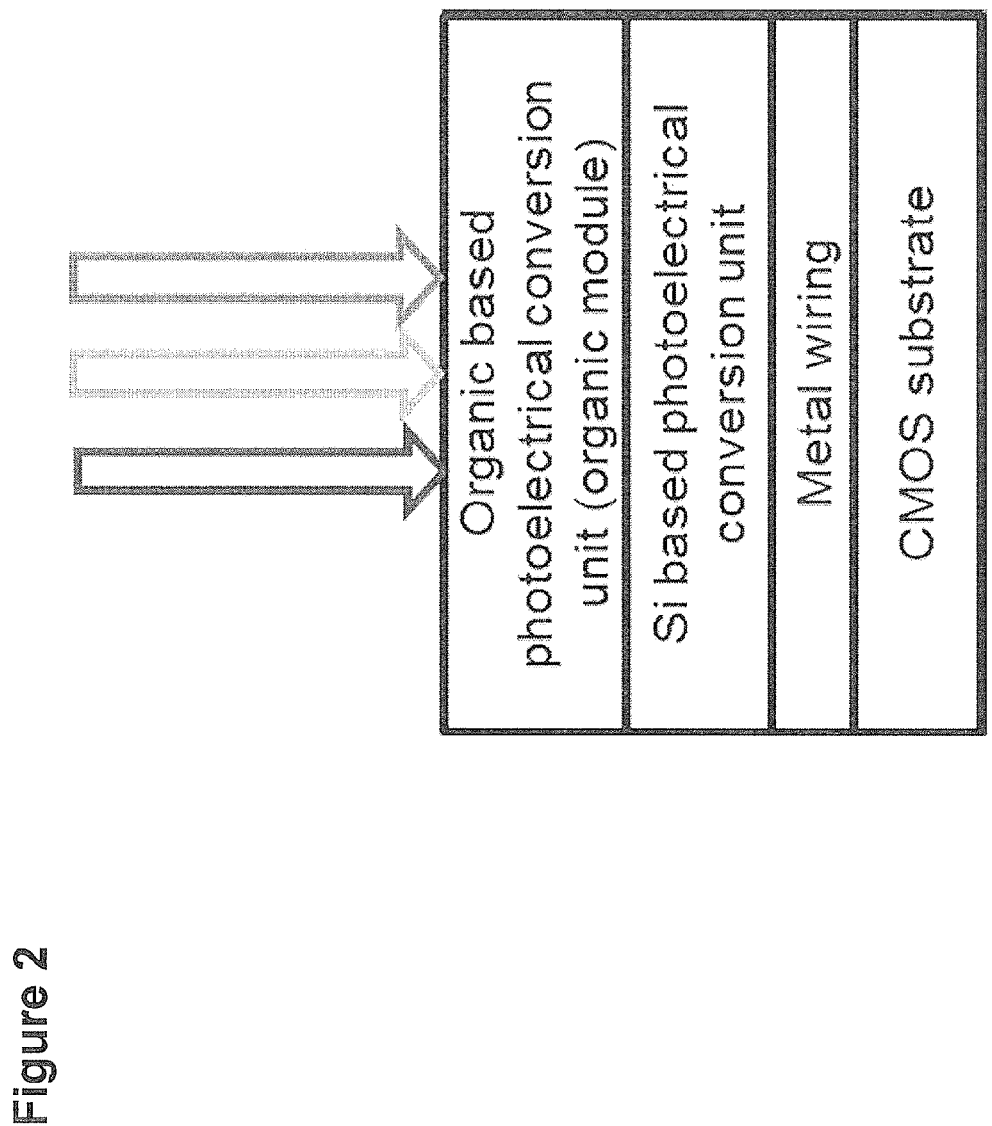
FIG. 2 shows a schematic representation of the hybrid silicon-organic image sensor.
Figure 3:
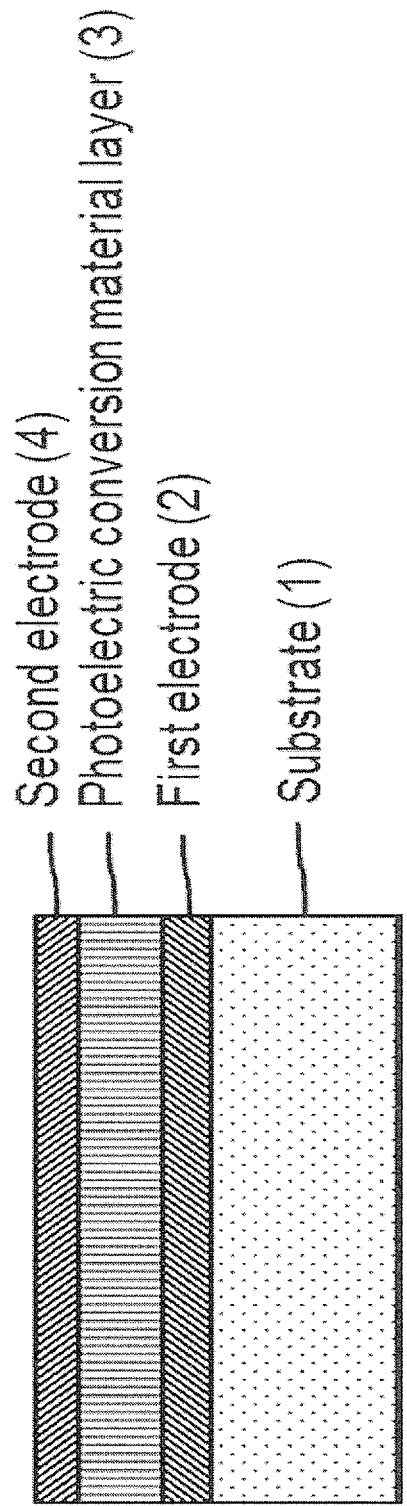
FIG. 3 shows a schematic representation of the organic based photoelectrical conversion unit with the different layers.

The organic photoconversion unit can be used in combination with a Si based photoelectrical conversion unit where different layers absorb different color (BGR) in a hybrid silicon-organic image sensor (see FIG. 2) or can be used without Si based photoelectrical conversion unit. In this case the organic photoconversion unit has the capability of absorbing different color (BGR) (see FIG. 3).

The BGR ranges are 400-500 nm, 500-600 nm and 600-700 nm and the absorption outside of the range is preferably less than 20%, more preferably less than 10 and 5%.

As discussed above, the substrate can also be other photoelectric conversion unit(s) (e.g. blue 400-500 nm and red 600-500 nm conversion devices in case the organic conversion layer according to this disclosure is green 500-600 nm conversion device).

As discussed above, a device of this disclosure can comprise (i) two inorganic units with one organic unit, (ii) one inorganic unit with two organic units, or (iii) three organic units combined with each other in the organic image sensor. Any of the organic units can contain molecules/layers/devices according to this disclosure.

The deposition methods to produce the organic photoelectrical conversion layer are PVD, CVD, spin coating, dipping coating, casting process, inkjet printing, screen printing, spray coating, offset printing.

Different process temperatures for processing the layer are possible, namely from 150 to 245° Celsius.

Note that the present technology can also be configured as described below.

(1) A molecule represented by a general formula selected from

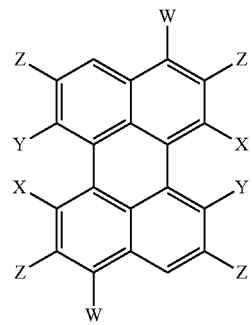

I

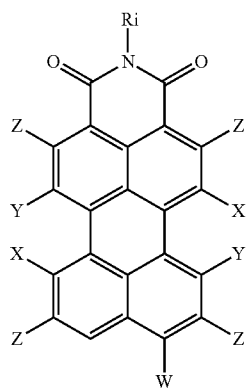

II

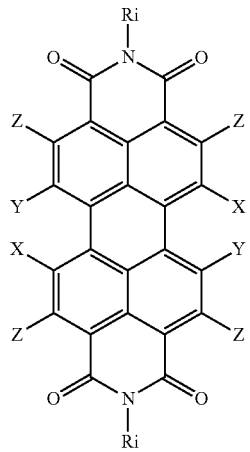

III wherein

X, and Y are the same or different and are, at each occurrence, independently selected from the following electron donating groups (EGD) and electron withdrawing groups (EWD):

hydrogen, halogen,

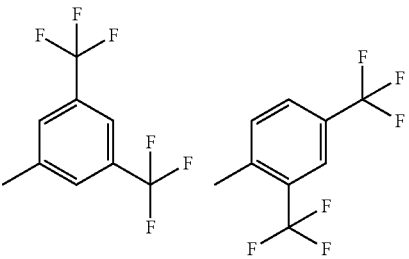

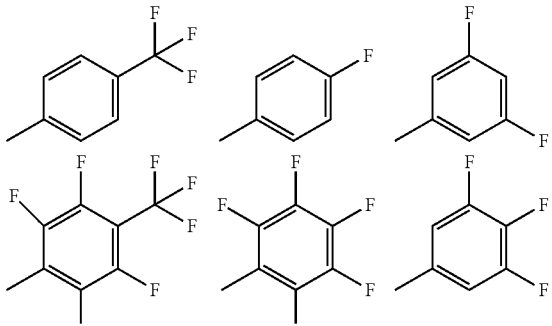

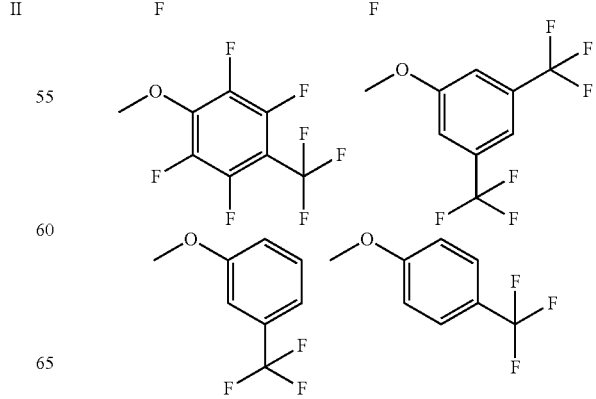

-continued

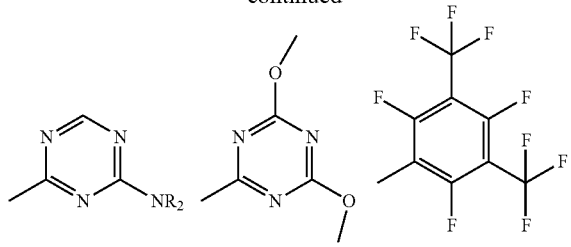

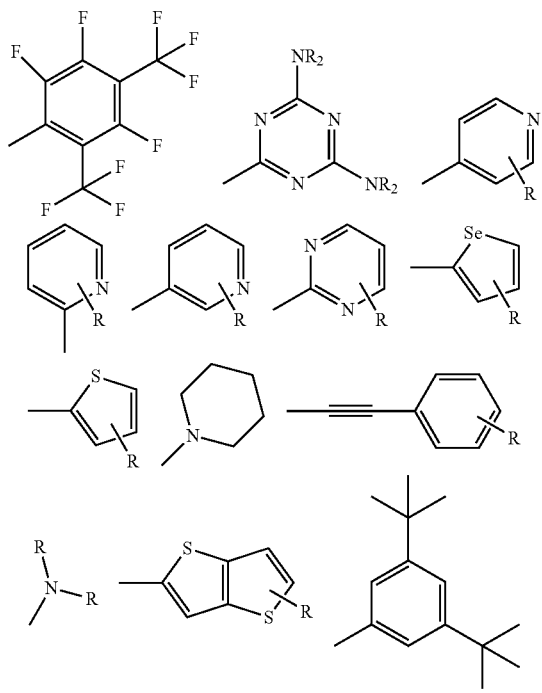

wherein R is independently selected from hydrogen, an alkyl or aryl substituent.

Z, at each occurrence, is independently selected from the following electron donating groups (EGD) and electron accepting groups (EAD)

—OCH$_3$,

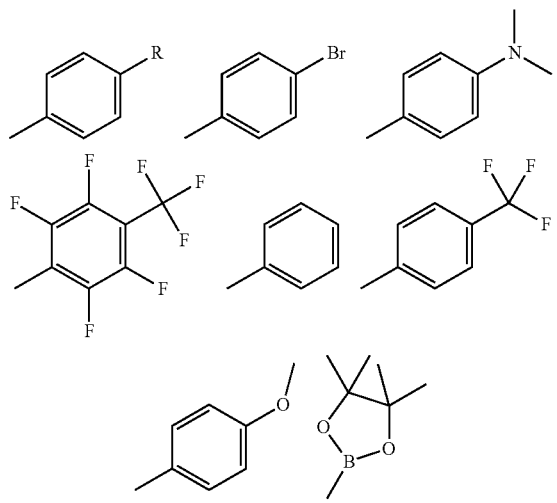

W, at each occurrence, is independently selected from the following electron donating groups (EGD) and electron withdrawing groups (EWD):

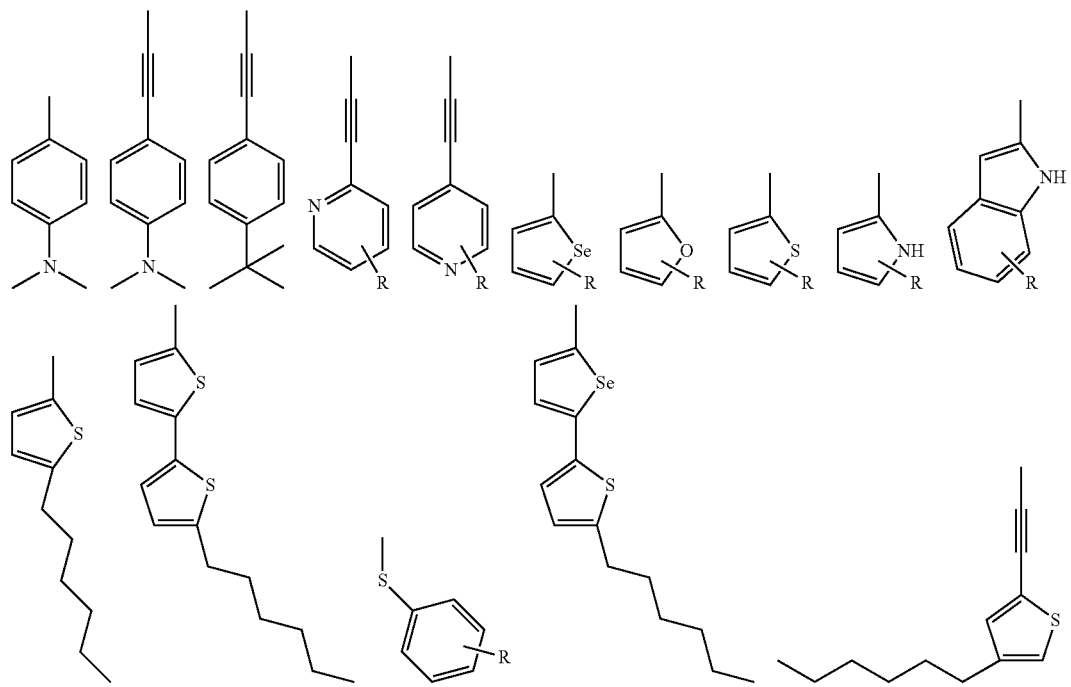

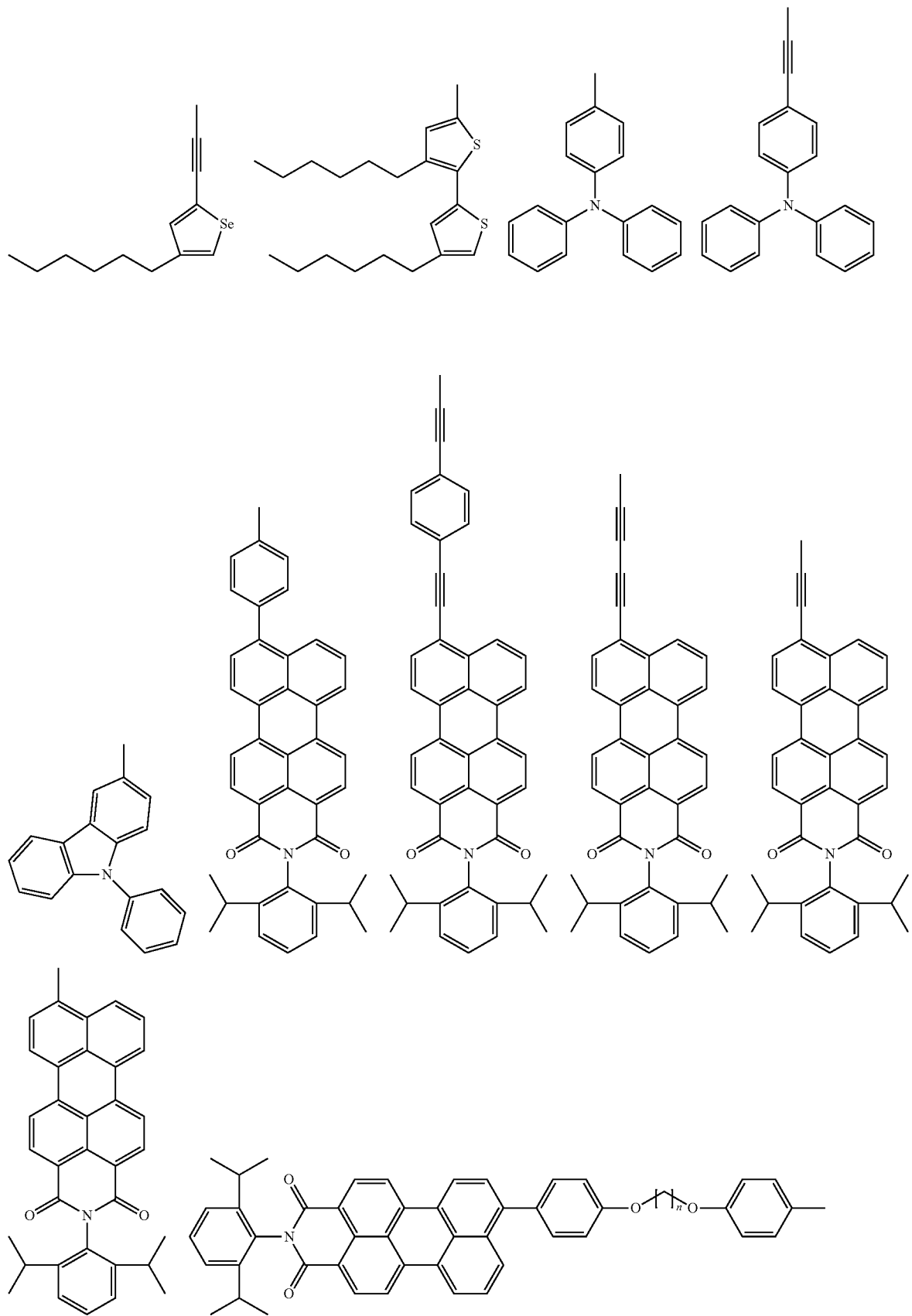

-continued
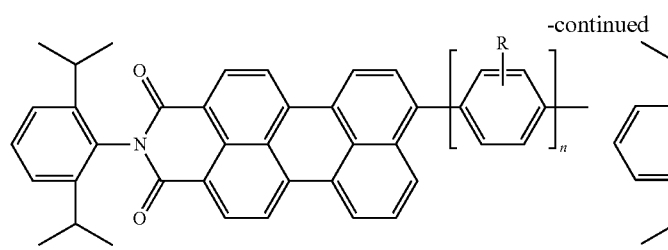
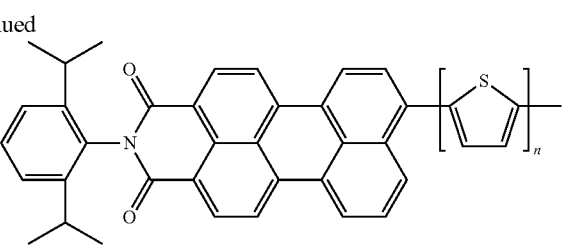
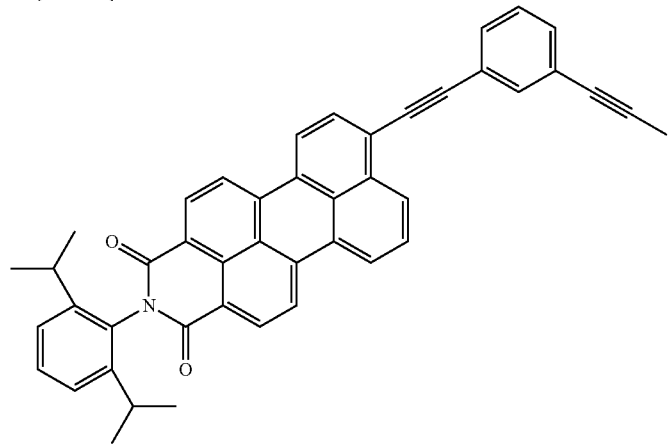
wherein
R is independently selected from hydrogen, an alkyl or aryl substituent,
n is an integer selected from 1 to 10,
and
Ri, at each occurrence, is independently selected from
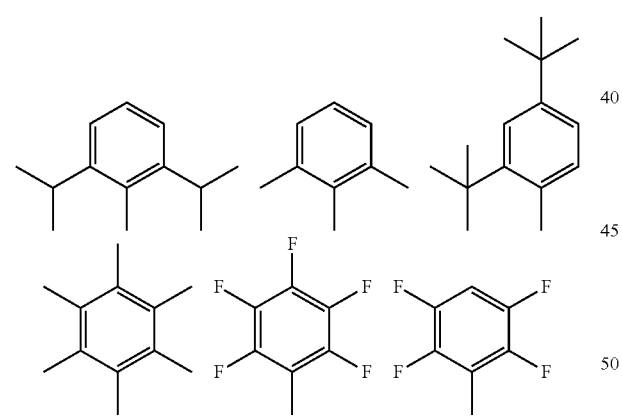
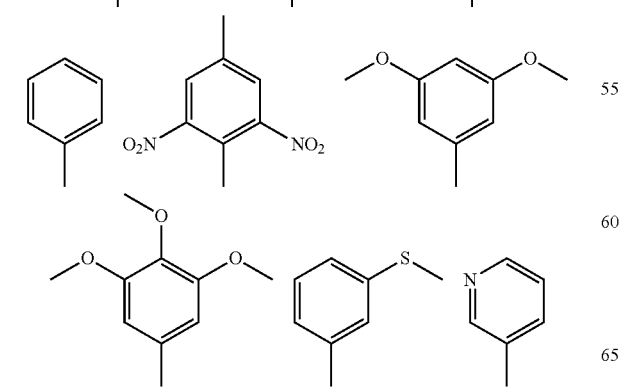
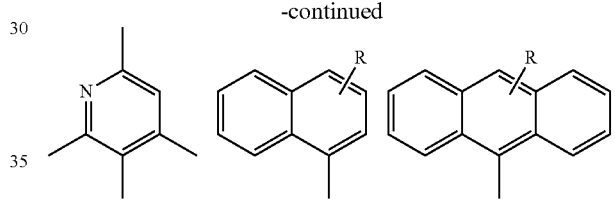
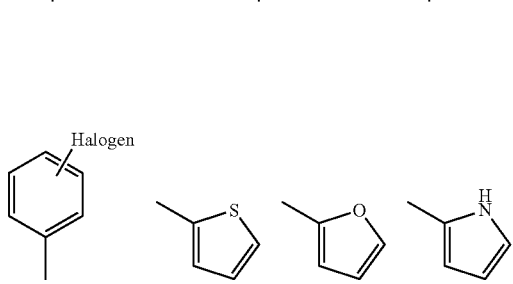
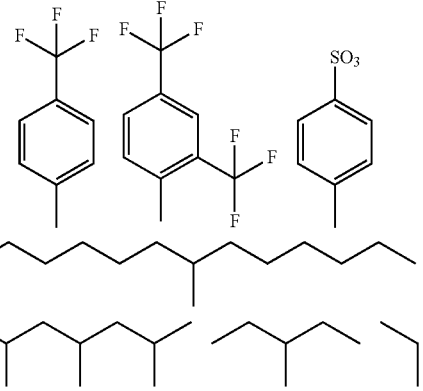

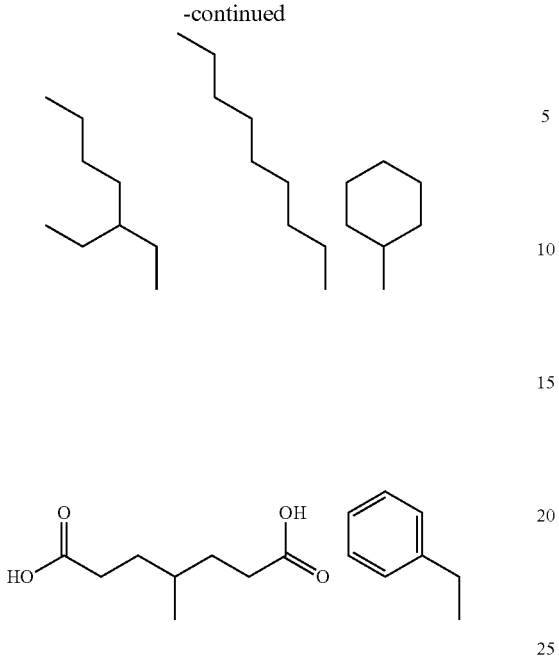

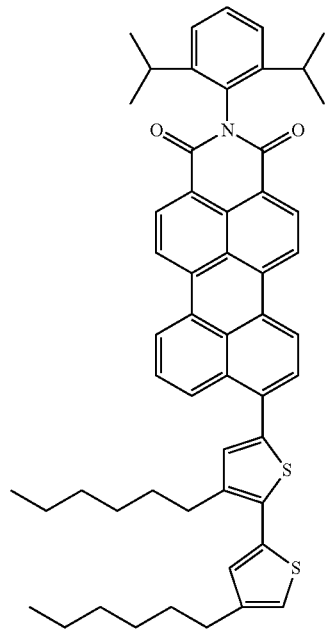

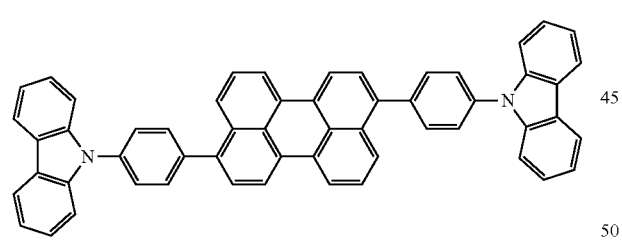

wherein, preferably, W, X, and Y are not cyano, nitro, quaternary amino, sulfo, carbonyl, substituted carbonyl, carboxy.

(2) The molecule according to (I), wherein the molecule is represented by formula I, and X, Y and Z are H, and W is an electron donating group (EDG) as defined in (1), such as the molecule is represented by or X, Y and Z are H, and W is an electron withdrawing group (EWG) as defined in (1).

(3) The molecule according to (1), wherein the molecule is represented by formula II and Ri is as defined in (1), X, Y and Z are and W is an electron donating group (EDG) as defined in (1), preferably the molecule is represented by any of structures

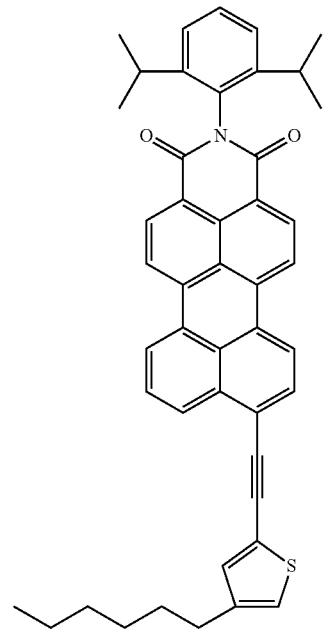

51
-continued
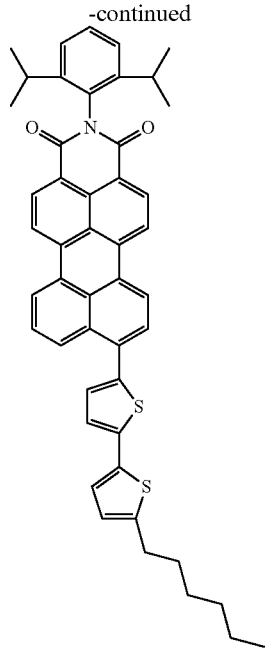
52
-continued
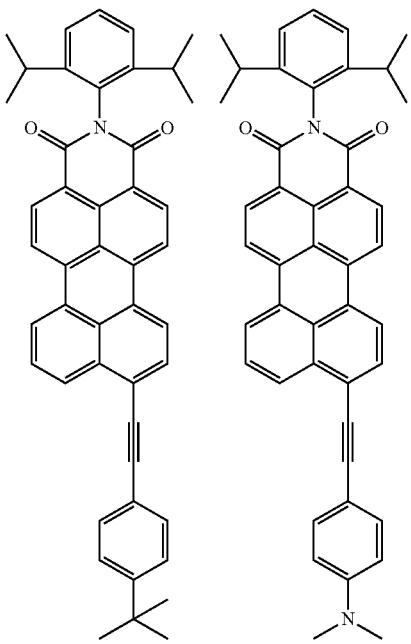
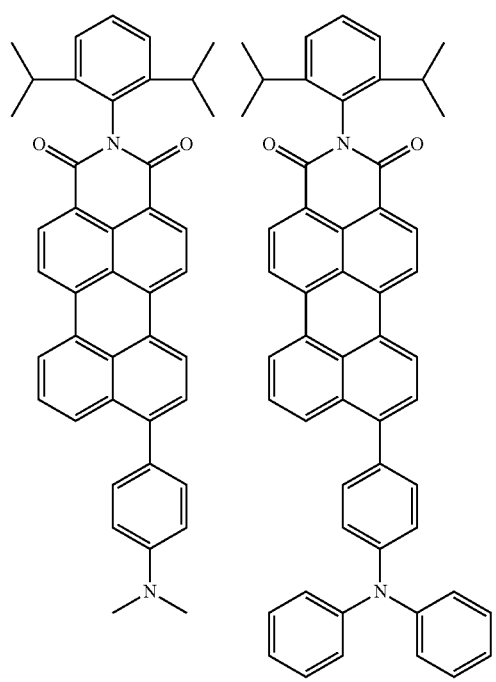
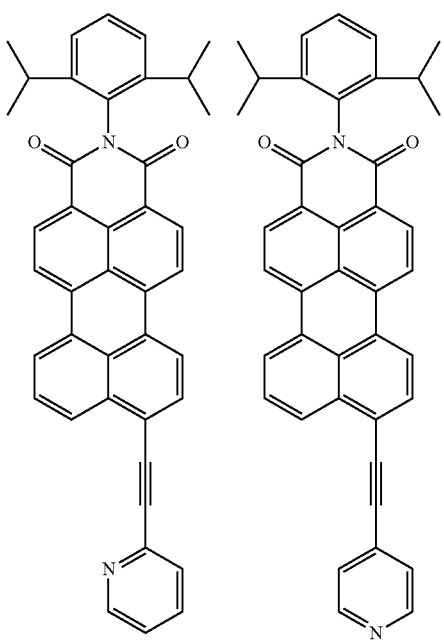

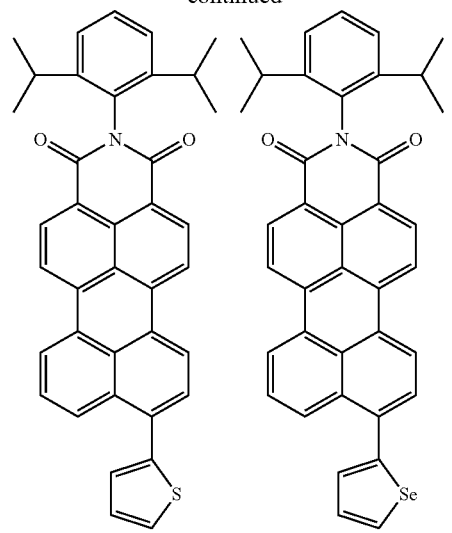
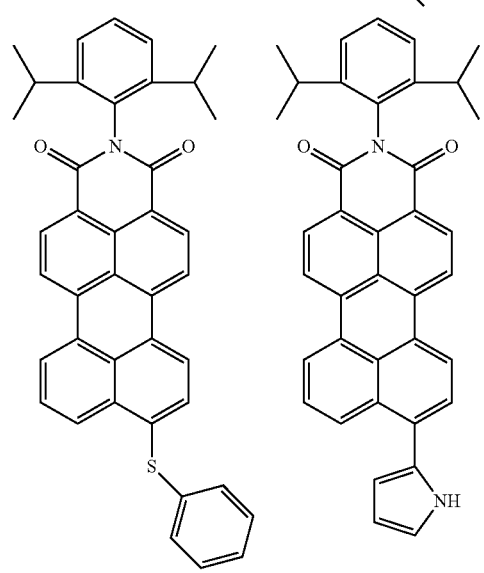
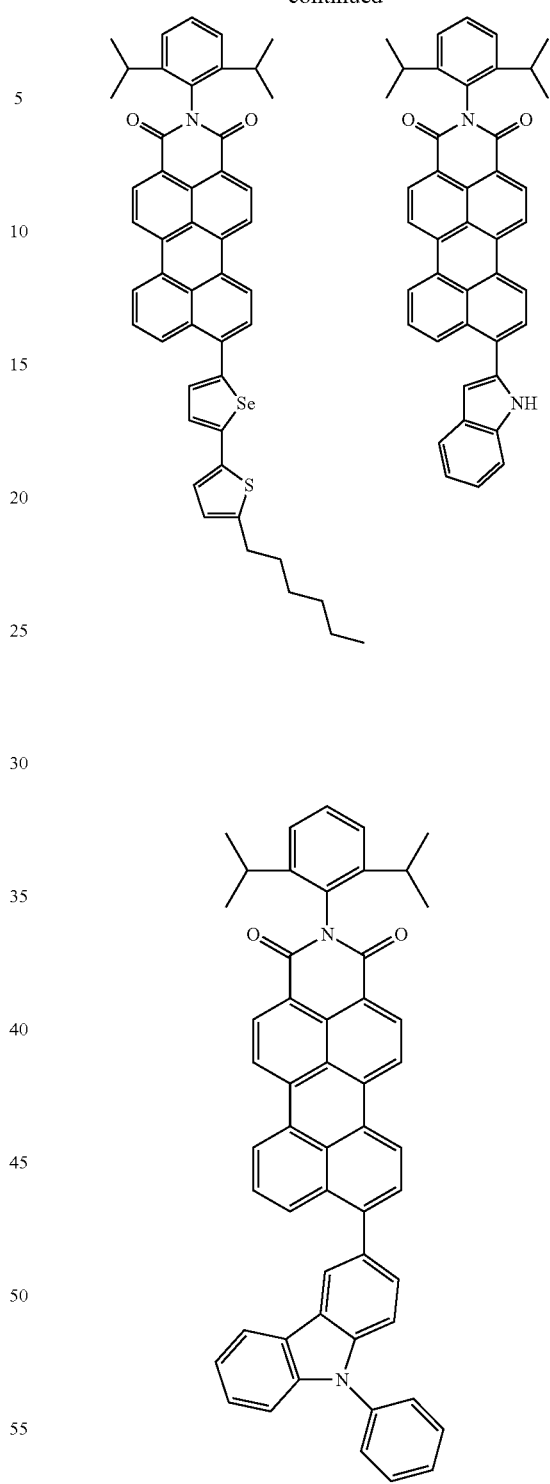
(4) The molecule according to wherein the molecule is represented by formula III and
Ri is as defined in (1),
X and Y are electron donating groups (EDG) as defined in (1), and
Z is H,
preferably the molecule is represented by any of structures 55
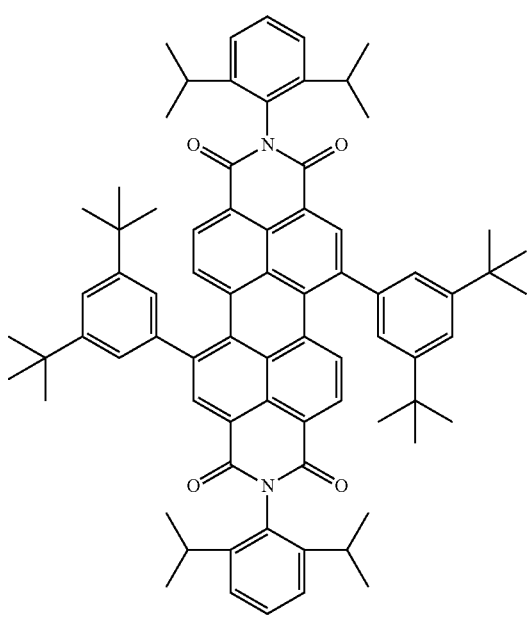
56
-continued
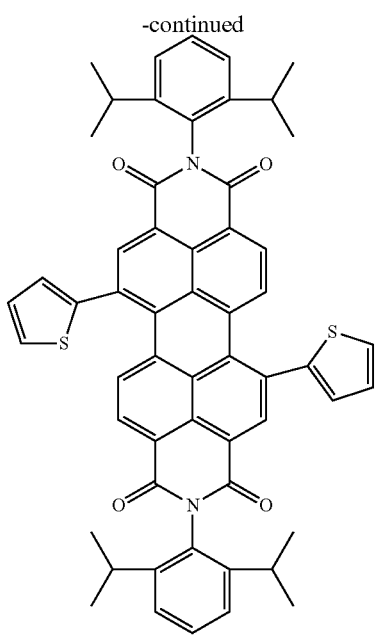
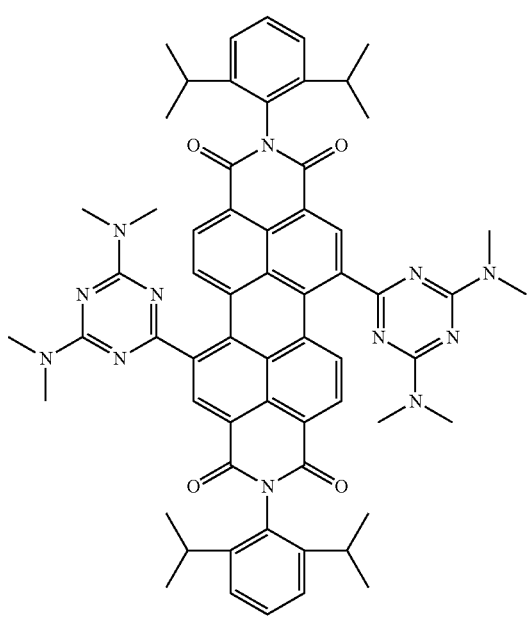
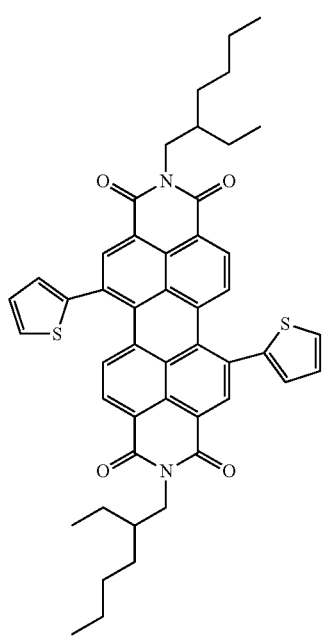

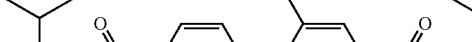

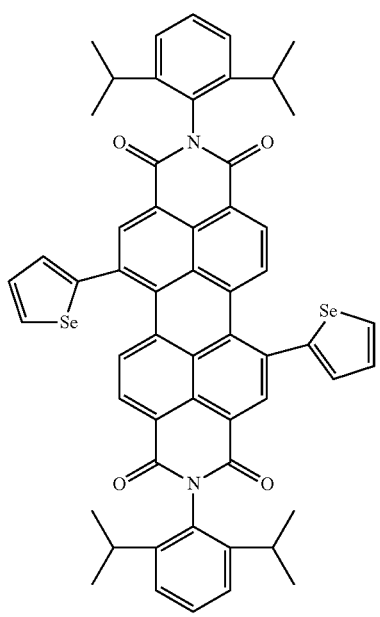

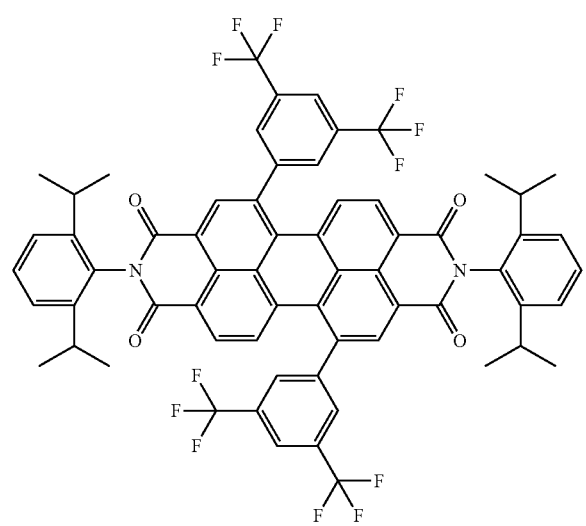

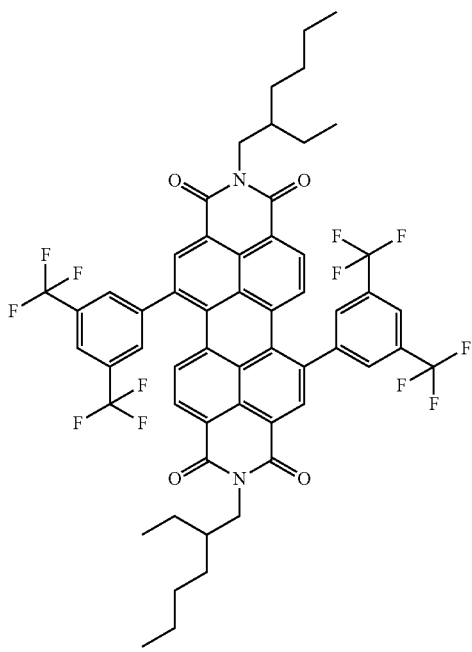

(5) The molecule according to (1), wherein the molecule is represented by formula III and Ri is as defined in (1).

X and Y are electron withdrawing group (EWG) as defined in (I), and

Z is H, preferably the molecule is represented by any of structures (6) The molecule according to (1), wherein the molecule is represented by formula HI and Ri is as defined in (1),
X and Y are H, and
Z is an electron withdrawing and electron donating group (EWG and EDG), preferably the molecule is represented by any of structures

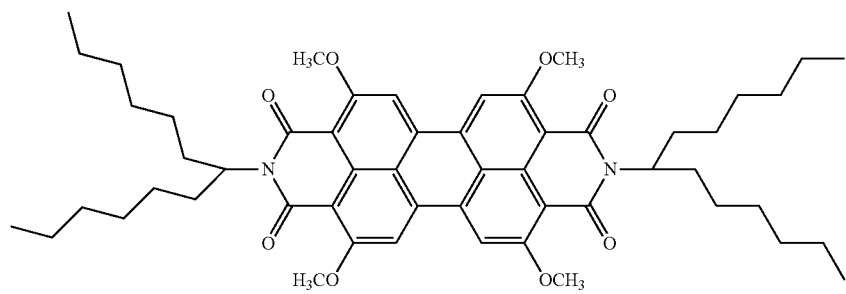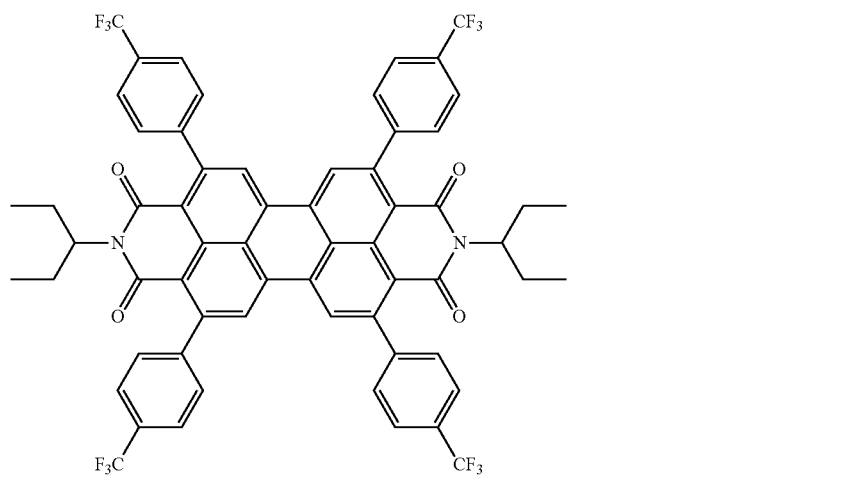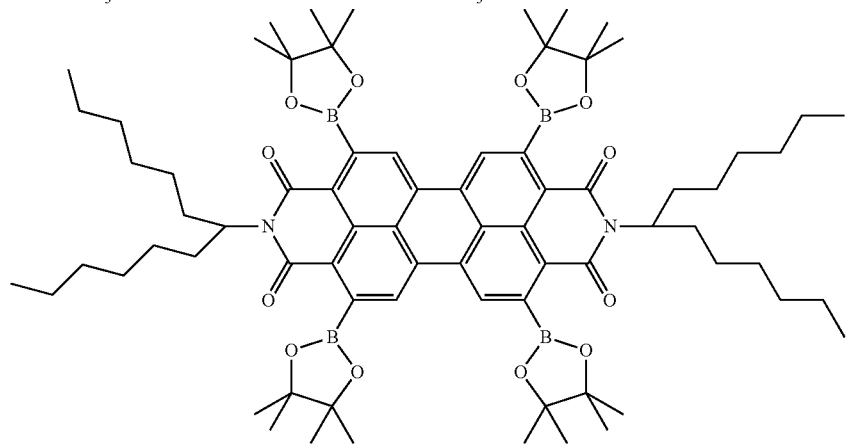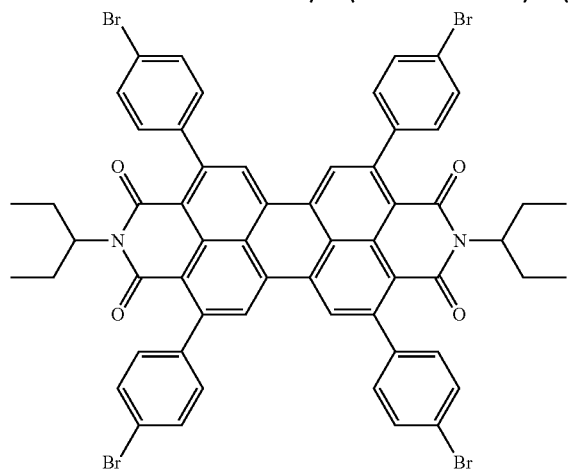

(7) The molecule according to (1) represented by any of structures
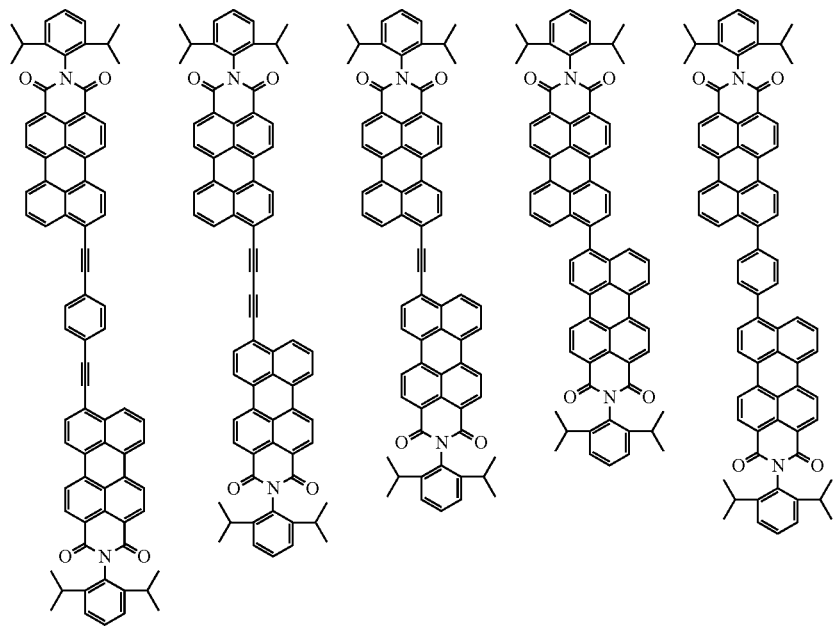
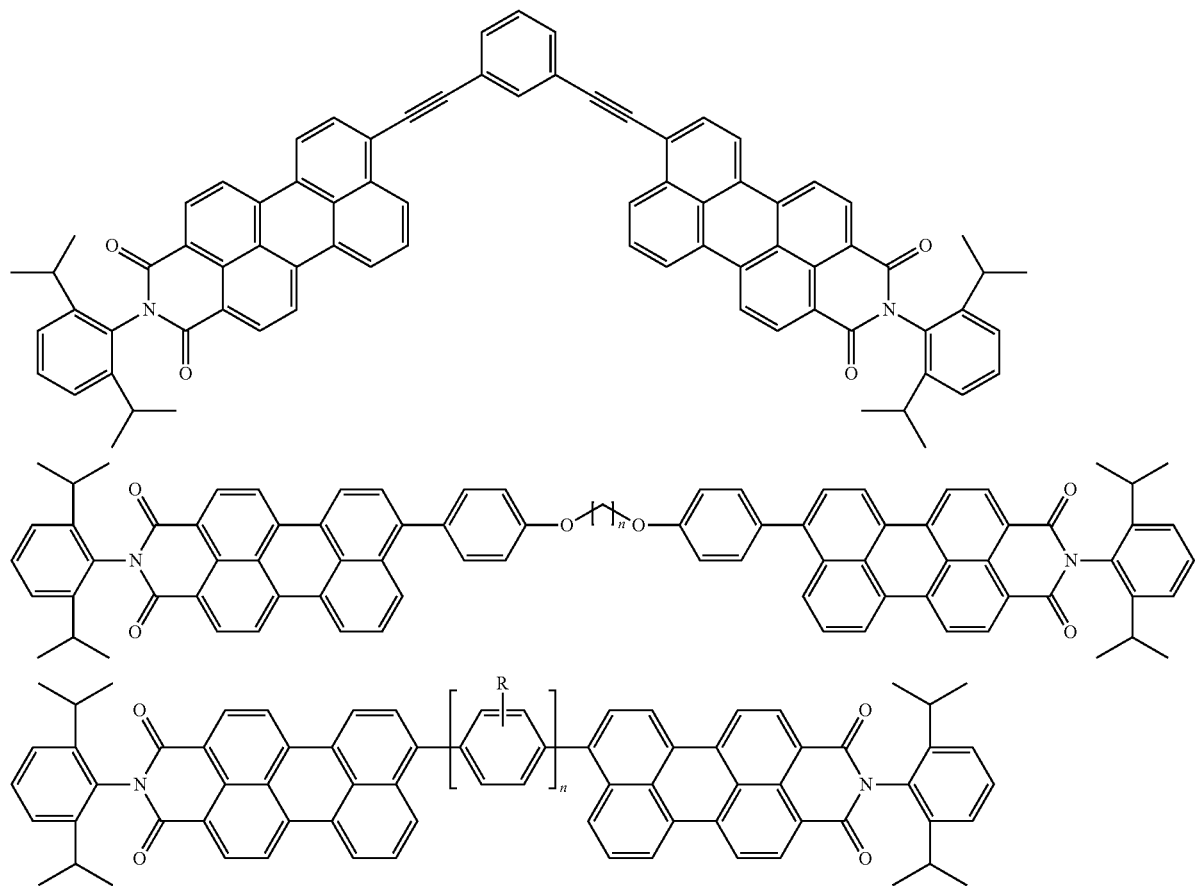

-continued

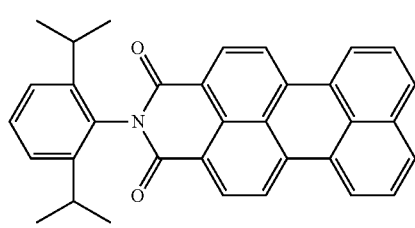
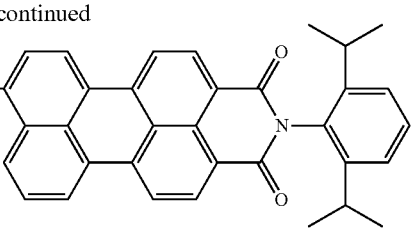

wherein
R is independently selected from hydrogen, an alkyl or aryl substituent,
n is an integer selected from 1 to 10.

(8) The molecule according to any one of (1) to (7), wherein the molecule exhibits
- absorption in the visible wavelength range (about 400 to about 700 nm),
- an extinction coefficient of $>10^4$ $Lmol^{-1}cm^{-1}$, and/or
- high thermal stability, preferably up to at least about 300° C. or up to at least about 300 to 500° C., preferably the molecule
- exhibits absorption in the wavelength range of visible light, preferably in the range from 400 nm to 700 nm, or a sub-range thereof, preferably 400 nm to 500 nm, or 500 nm to 600 nm, or 600 nm to 700 nm.
- absorbs in the blue absorption range or absorbs in the green absorption range or absorbs in the red absorption range,
- absorbs less than 20% (more preferably less than 5%) of the maximum absorption outside of its main range of absorption.

(9) Use of a molecule according to any one of (1) to (8) in an absorption layer and/or a photoelectric conversion layer and/or in an organic and/or hybrid module for optoelectronic application, such as image sensor, photodiode, organic photovoltaics, including organic photoelectric conversion layer(s), OLED and OTFT organic modules.

(10) A photoelectric conversion layer including a molecule according to any one of (1) to (8), optionally including further molecule(s).

(11) An absorption layer comprising a molecule according to any one of optionally including further molecule(s).

(12) A device including a photoelectric conversion layer including at least one molecule represented by a general formula selected from

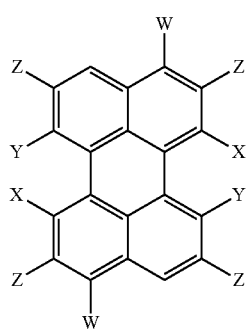

I

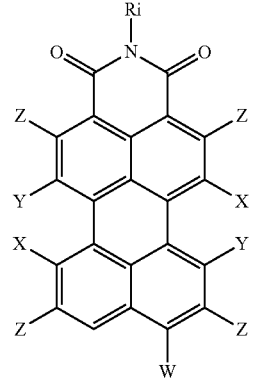

II

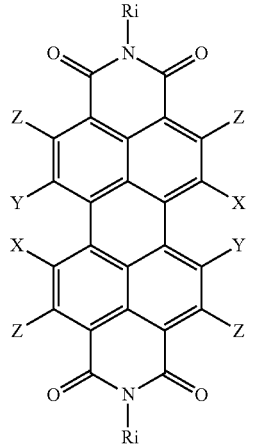

III wherein
X, and Y are the same or different and are, at each occurrence, independently selected from H, electron donating groups (EGD) and electron withdrawing groups (EWD),
preferably halogen, aryl, heteroaryl, substituted aryl, substituted heteroaryl, cycloakyl, fluoro-substituted moieties (such as fluoro-substituted aryl, heteroaryl), amino-substituted moieties (such as amino-substituted aryl, heteroaryl), Z, at each occurrence, is independently selected from H, electron donating groups (EGD) and electron accepting groups (EAD),
preferably carboxy, aryl, substituted aryl, fluoro-substituted moieties (such as fluoro-substituted aryl), amino-substituted moieties (such as amino-substituted aryl), W, at each occurrence, is independently selected from H, electron donating groups (EGD) and electron withdrawing groups (EWD),
preferably aryl, heteroaryl, substituted aryl, substituted heteroaryl, cycloalkyl, alkyl-substituted moieties (such as alkyl-substituted aryl, heteroaryl), alkenyl-substituted moieties (such as alkenyl-substituted aryl, heteroaryl), alkynyl-substituted moieties (such as alkynyl-substituted aryl, heteroaryl), preferably not all of W, X, Y, and Z are H, Ri, at each occurrence, is independently selected from alkyl, cycloalkyl, aryl, fluoro-substituted aryl, heteroaryl, fluoro-substituted heteroaryl, halogen-substituted aryl, halogen-substituted heteroaryl, wherein said device preferably is an organic image sensor, an hybrid image sensor, photodiode, organic photovoltaics, organic light-emitting diode (OLED), organic thin-film transistor (OTFT).

(13) The device according to (12), wherein said photoelectric conversion layer exhibits photo response in the visible absorption range.

(14) The device according to (12) or (13), including molecule(s) according to any one of (1) to (8) or photoelectric conversion layer(s) according to (14), and/or including further molecule(s).

(15) An organic image sensor, including (a) an organic photoelectric conversion unit including photoelectric conversion layer(s) as defined in (12) or according to (10), (b) at least one electrode, (c) a substrate, (d) optionally, a second electrode on top of said photoelectric conversion layer(s), preferably not including color filter(s).

(16) A hybrid Silicon-organic image sensor or organic image sensor, including (a) an organic photoelectric conversion unit or units including photoelectric conversion layer(s) as defined in (12) or according to (10), (b) optionally, a Si based photoelectric conversion unit, (c) metal wiring, (d) a (CMOS) substrate, (e) insulating layer(s), preferably oxide.

(17) The organic image sensor according to (15) or (16), wherein said organic photoelectric conversion unit comprises different layers, such as n-type material, p-type material, n-buffer layer and/or p-buffer layer or combinations or mixtures thereof.

The term "perylene molecule" or "perylene-based molecule", as used herein, refers to a molecule having two naphthalene molecules connected by a carbon-carbon bond at the 1 and 8 positions on both molecules. The perylene-based molecules herein also comprise perylene monoimides, perylene diimides, perylene monoimide dimers.

The term "absorption in the visible wavelength range" or "molecule exhibiting absorption in the visible wavelength range", as used herein, is meant to refer to a molecule/dye that is able to absorb light in only one or several parts of the entire range indicated or over the total range. For example a molecule may only absorb in the range of from 500-700 nm, whereas another molecule may absorb in the range of from 400-700 nm, whereas a third molecule may absorb over the range of from 400-500 nm (or the above described sub-ranges of 400 nm to 500 nm or 500 nm to 600 nm or 600 nm to 700 nm). All these scenarios are meant to be encompassed by such wording.

In accordance with the present disclosure, the term "electrode" refers to an electrical lead to apply voltage. An electrode may be "interdigitated", meaning that it has a comb-like shape with two combs lying opposite each other and the respective figures of the combs engaging with each other. Alternatively, an electrode may be a non-interdigitated. An electrode may be transparent or non-transparent. A transparent electrode may, for example, be formed from indium tin oxide (ITO) or from fluorinated tin oxide (FTO) or from IZO or IGZO. A non-transparent electrode may be reflective and may, for example, be formed from silver (Ag) or gold (Au).

The requirements of a photoelectric conversion layer to be used in image sensors are demanding and can be summarised as followed:

(i) defined or narrow absorption band;

(ii) high extinction coefficient, $\epsilon > 10^4$ $Lmol^{-1}cm^{-1}$ (for high absorptance and absorption efficiency in thin film);

(iii) correspondingly thin films with high absorption coefficient;

(iv) heat resistant;

(v) high photoelectric conversion efficiency (EQE);

(vi) fast response/high charge carrier mobility;

(vii) low dark-current in device or low trap density;

(viii) thin film by physical vapour deposition (Tvp<Tdec).

The present inventors have found novel perylene-based molecules which are highly suitable as active materials for organic photoelectric conversion layers with improved conversion efficiency and response speed in organic photodiodes. The advantages of those materials with respect to the requirements, the different type of possible molecular structures and example of molecules for use as photoelectrical conversion layer are reported herein.

The present disclosure relates to perylene-base molecules with specific molecular formulas that absorb in the visible range (400-700 nm), but are not limited to it and their use as active materials for use in bulk heterojunction (mixed p-n layer) or PN heterojunction (formed between a p layer and n layer) or PiN junction (p layer-mixed layer as p-n bulk heterojunction-n-layer) in the photoelectric conversion material layer.

The organic photoconversion unit can be used in combination with a Si based photoelectrical conversion unit where different layer absorbed different colour (BGR) in a hybrid Silicon-organic image sensor or can be used without Si based photoelectrical conversion unit. In this case the organic photoconversion unit having the capability of absorbing different colour (BGR). The general structure of the resulting hybrid image sensor device as well as the details of the organic based photoelectrical conversion unit are schematic represented in the FIGS. 2 and 3.

The main advantages of the perylene based molecules for the application in photoelectrical conversion layers are as follows:

(1) high exciton diffusion efficiencies in thin films (up to 99%);

(2) high exciton dissociation ability—allow for photoconversion devices with high EQE;

(3) good extinction coefficients ($\epsilon > 10^4$ $Lmol^{-1}cm^{-1}$);

(4) tuning of the absorbion maximum (optical band gap) and shape over a broad range is possible;

(5) easy alteration of HOMO and LUMO energy levels;

(6) excellent photostability;

(7) hi stability (300 to 500° C. depending on substituents but at least 300° C.)

(8) high electrons and holes mobilities.

The absorption energy levels and the morphology in thin film are tunable by the type of substituent X, Y, Z, W and Ri.

This makes the perylens based molecules of the present disclosure very versatile molecules to be used in the organic photoelectric conversion layer.

EXAMPLES

Example 1: Perylene-Hosed Molecule

Scheme 1 shows the general synthetic route for perylene-based molecules of the present disclosure where the perylene is modified in pery position (W).

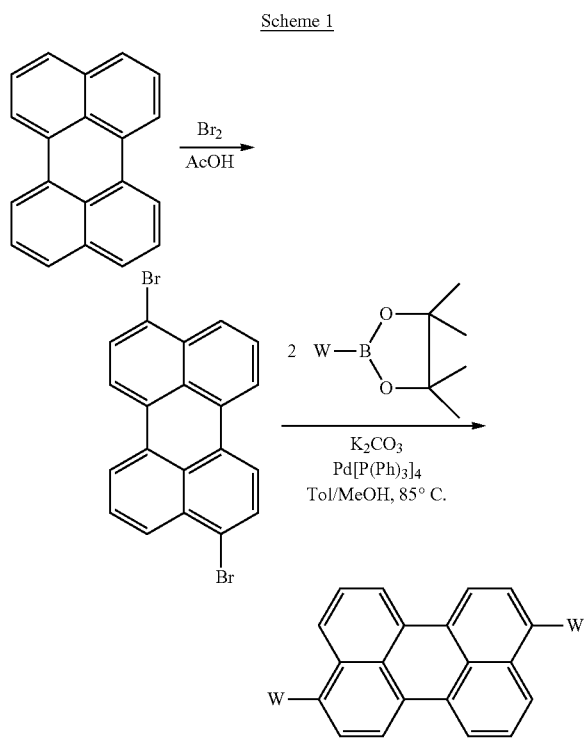

Figure 4:
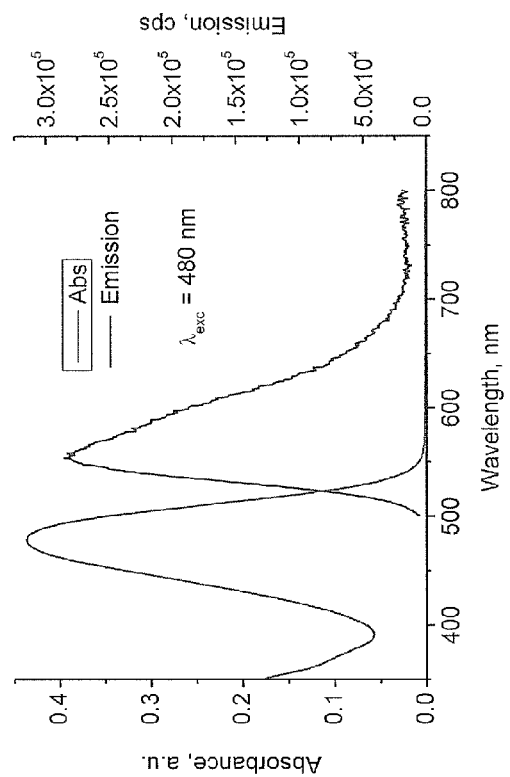
FIG. 4 shows the perylene molecule of Example 1, its synthesis route and its absorption in solution.
Figure 4:
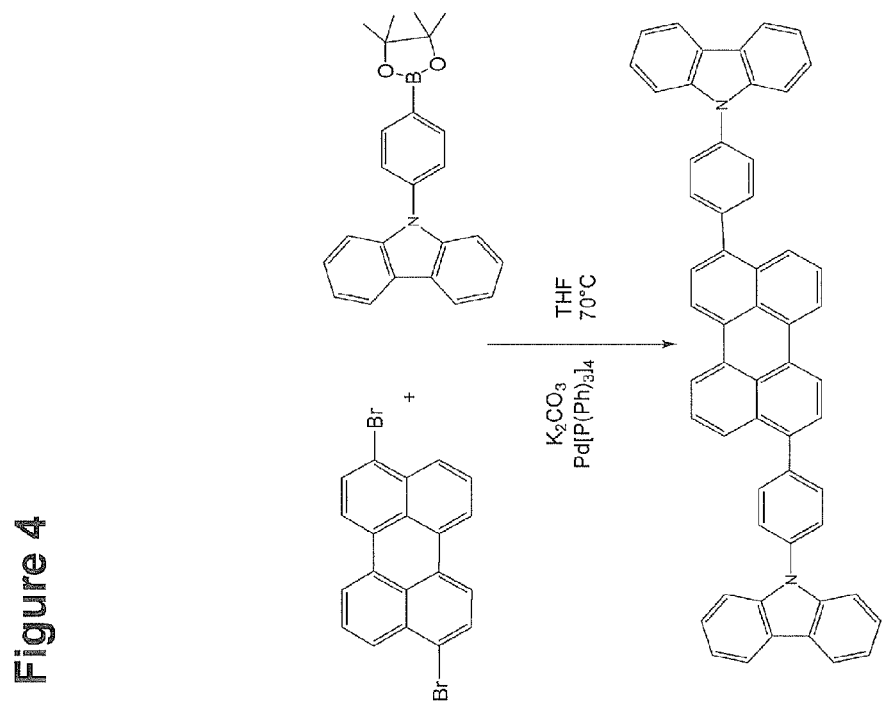

Following Scheme 1, the inventors synthesized the perylene-based molecule PPhCarbazole (shown below), a diphenyl carbazole derivative, that showed and absorption maximum at 458 nm (see FIG. 4).

PPhCarbazole

Example 2: Perylene-Diimide-Based Molecules

In the scheme below (Scheme 2) is reported the general synthetic route for the preparation of perylene dimide substituted in the bay position (X, Y).

Figure 5A:
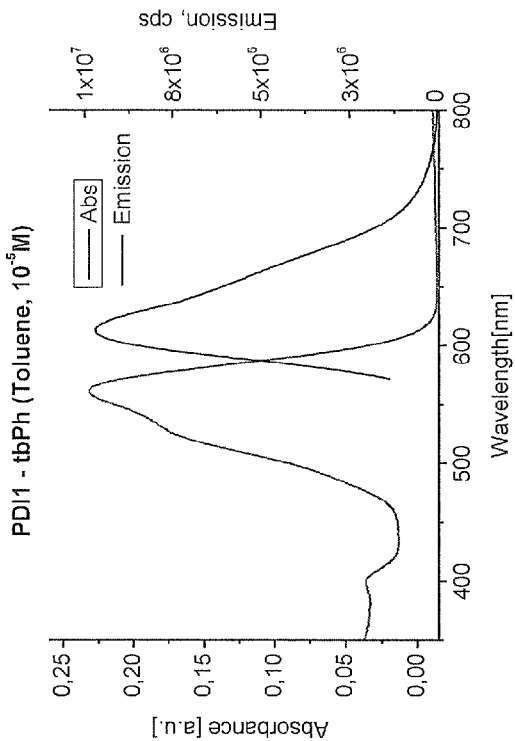
FIG. 5 shows (A) the perylene diimide molecule of Example 2, its absorption in solution and (B) its melting curves (TG and DSC).
Figure 5A:
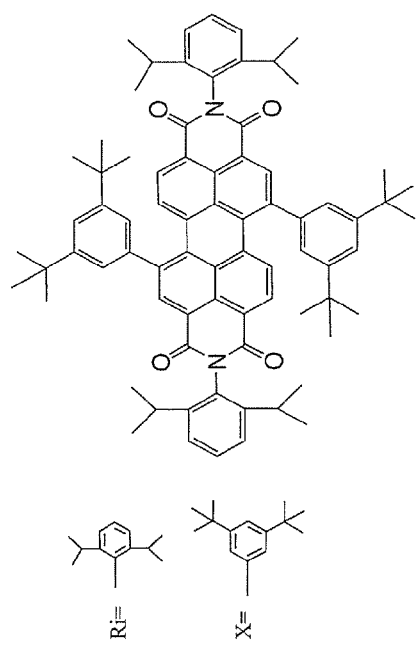
Figure 5:
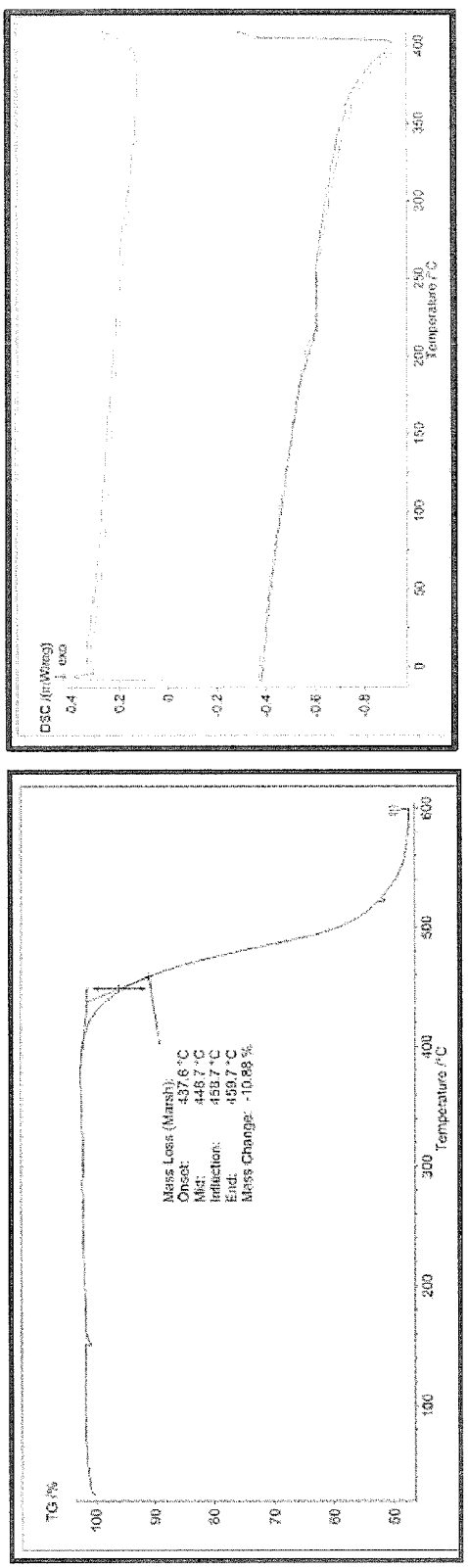

Using this synthetic route several compounds have been synthesised. The compound PDI 1-tBuPh is shown as example. It shows excellent thermal stability as it can be seen from the TG ($T_{onset}$ circa 400° C.), no crystallinity (DSC traces do not show melting and crystallization transitions) and absorption maximum at 561 nm. See FIG. 5.

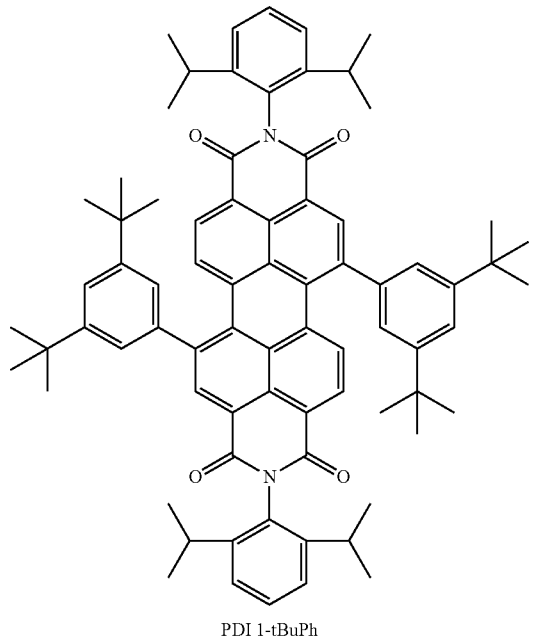 [SMILES: CC(C)c1cccc(C(C)C)c1N1C(=O)c2ccc3c4c(-c5cc(C(C)(C)C)cc(C(C)(C)C)c5)cc5c6c(ccc(c7c(-c8cc(C(C)(C)C)cc(C(C)(C)C)c8)cc(c2c37)C1=O)c64)C(=O)N(c1c(C(C)C)cccc1C(C)C)C5=O]

PDI 1-tBuPh

Figure 6:
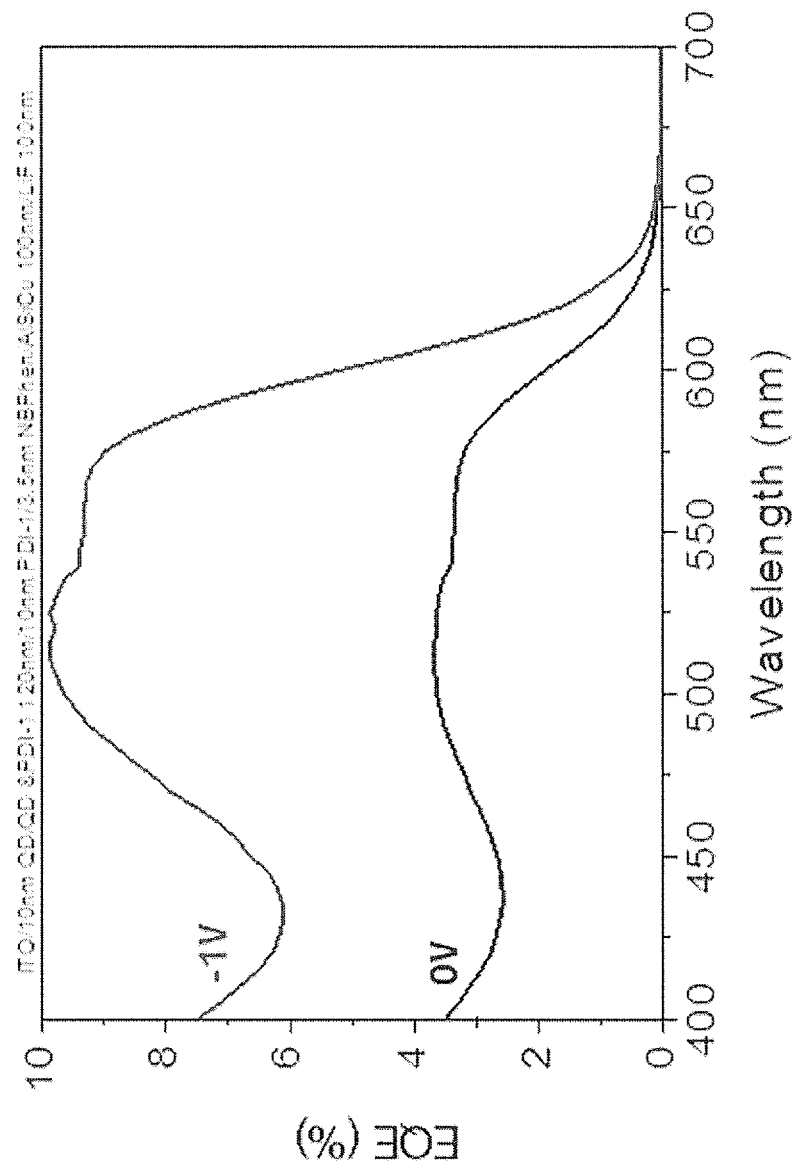
FIG. 6 shows the External Quantum Efficiency (EQE) of a photoelectric conversion layer wherein the perylene diimide molecule of Example 2 was used as acceptor material in combination with quinacridone (QD) as donor.

The PDI 1-TBuPh derivate was used as acceptor material in combination with quinacridone (QD) as donor in the following configuration: ITO/10 nm QD/QD & PDI1 120 nm/10 nm PDI1/3.5 nm NBPhen/AlSiCu 100 nm/LiF 100 nm. The device gave an EQE at 517 nm of 3.4% @0V and 9.9%@-1V. See FIG. 6. The exciton diffusion efficiencies (EDE) of this layer is up to 88±1%.

Example 3: Perylene Monoimide Based Molecules

In the scheme below (Scheme 3) is reported the general synthetic route for the preparation of perylene monoimide substituted in the pery position (W).

Scheme 3

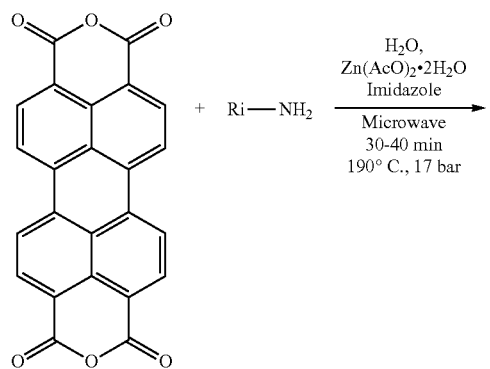

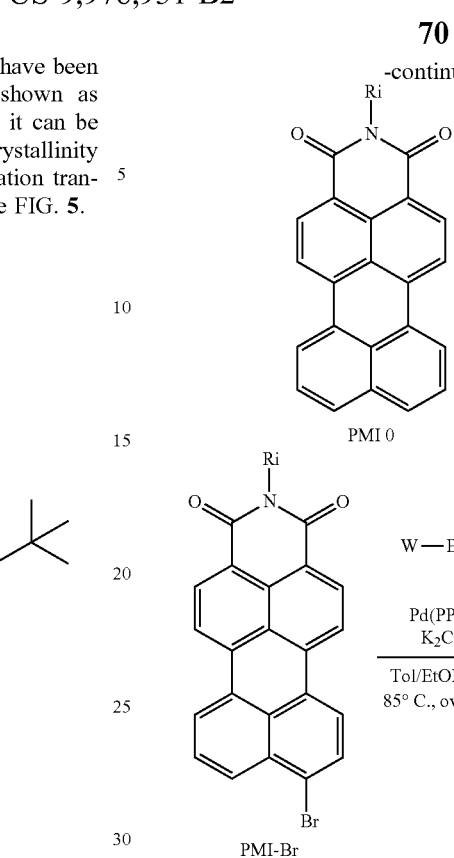

PMI 0

PMI-Br

Figure 7A:
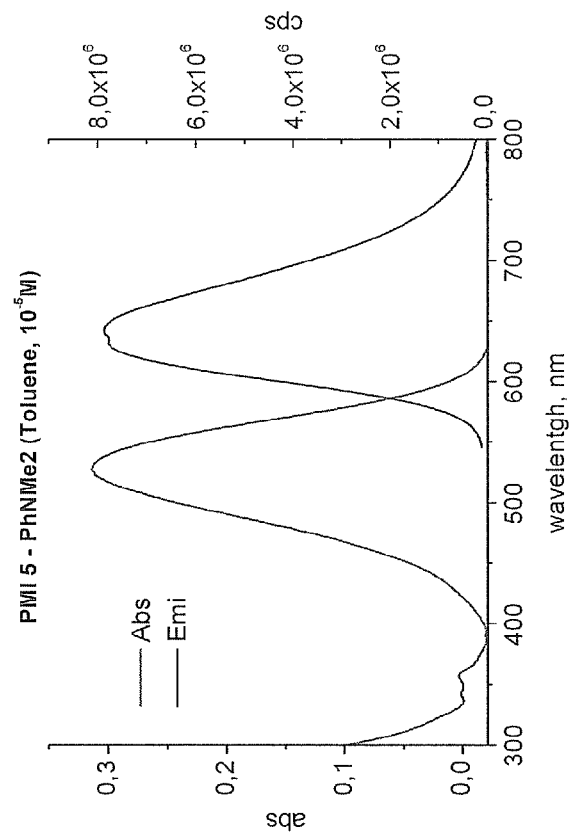
FIG. 7 shows (A) the perylene monoimide molecule of Example 3, its absorption in solution and (B) its melting curves (TG and DSC).
Figure 7A:
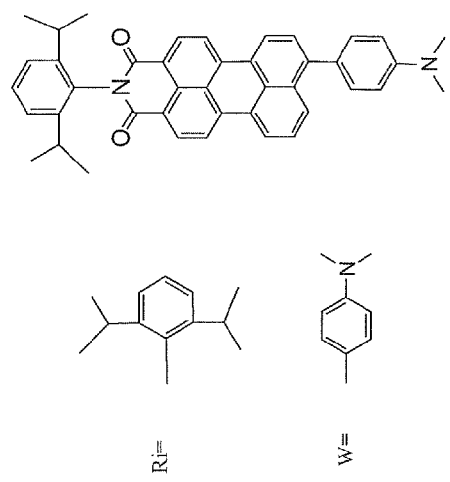
Figure 7:
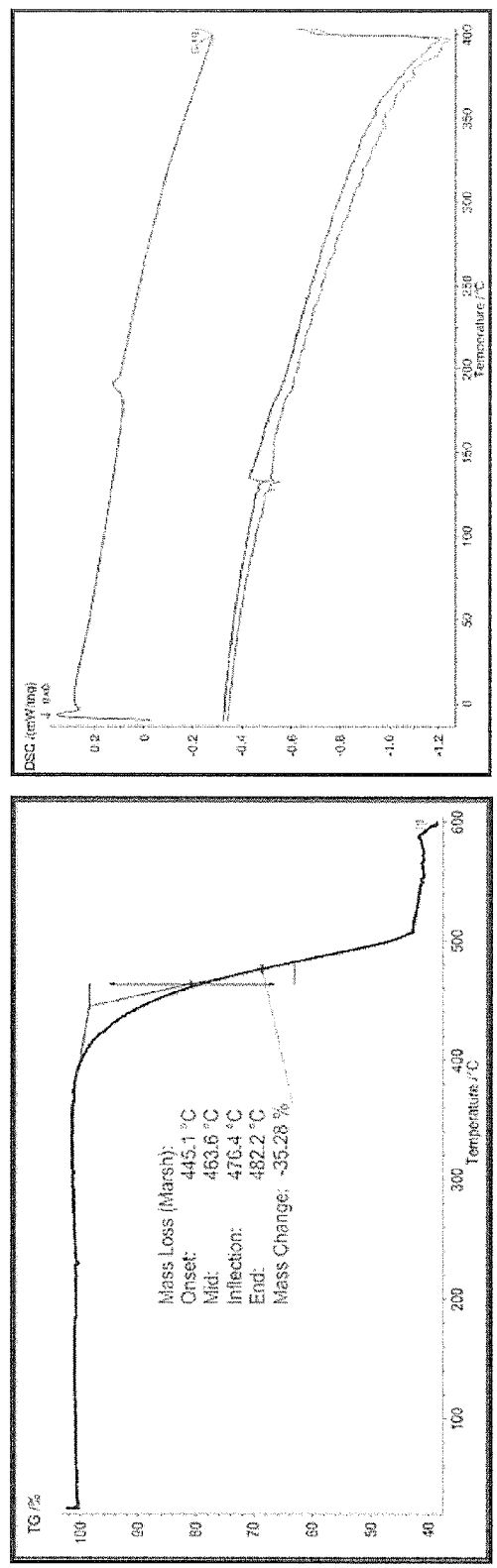

Using this synthetic route several compounds have been synthesized. The compound PMI5-PhNMe2 is shown as example. It shows excellent thermal stability as it can be seen from the TG ($T_{onset}$ circa 400° C.), no crystallinity (DSC traces do not show melting and crystallization transitions) and absorption maximum at 528 nm. See FIG. 7.

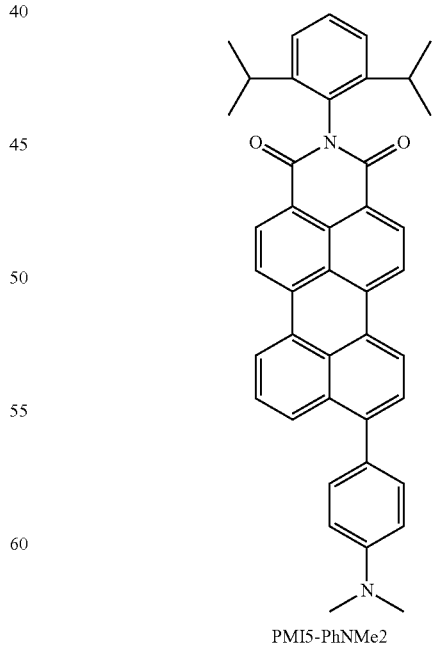

PMI5-PhNMe2

Figure 8:
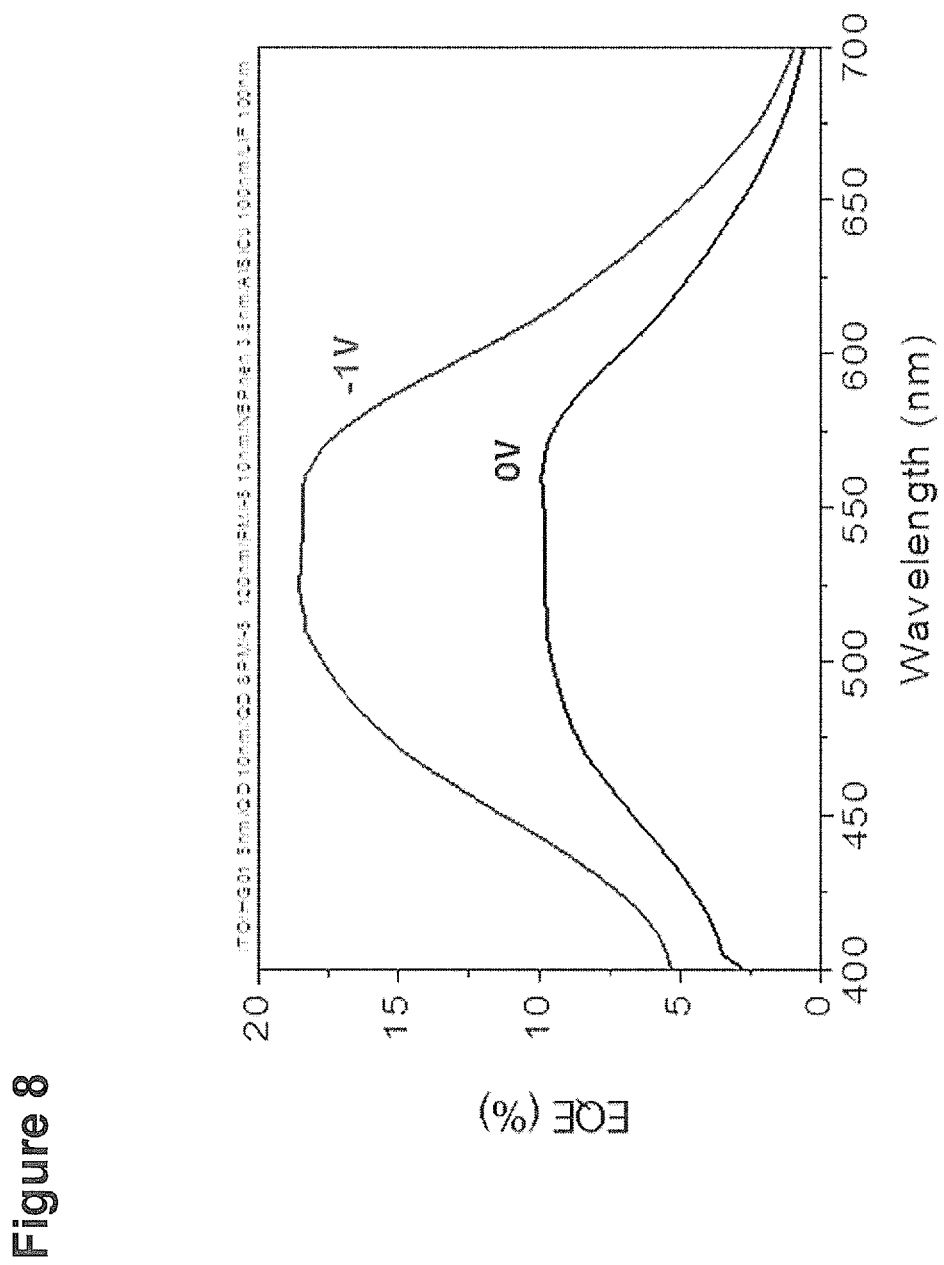
FIG. 8 shows the External Quantum Efficiency (EQE) of a photoelectric conversion layer wherein the perylene monoimide molecule of Example 3 was used as acceptor material in combination with quinacridone (QD) as donor.

The PMI5-PhNMe2 derivate was used in combination with quinacridone (QD) as in the following configuration:

ITO/10 nm QD/QD & PMI5 120 nm/10 nm PMI5/3.5 nm NBPhen/AlSiCu 100 nm/LiF 100 nm. The device gave an EQE at 561 nm of 9.9%@0V and 18.5% @−1V. See FIG. 8. The exciton diffusion efficiencies (EDE) of this layer is 75±3%.

Thus, the foregoing discussion discloses and describes merely exemplary embodiments of the present disclosure. As will be understood by those skilled in the art, the present disclosure may be embodied in other specific forms without departing from the spirit or essential characteristics thereof. Accordingly, the disclosure of the present disclosure is intended to be illustrative, but not limiting of the scope of the disclosure, as well as other claims. The disclosure, including any readily discernible variants of the teachings herein, defines, in part, the scope of the foregoing claim terminology such that no inventive subject matter is dedicated to the public.

The present application claims priority to European Patent Application 14162902.2, filed in the European Patent Office on Mar. 31, 2014, the entire contents of which being incorporated herein by reference.

The invention claimed is:

1. A molecule represented by a general formula selected from I, II or III:

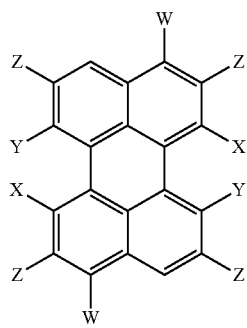

I

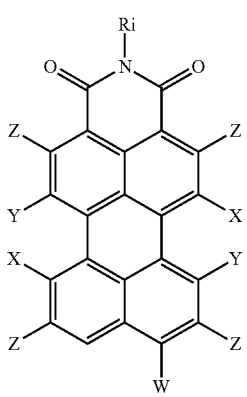

II

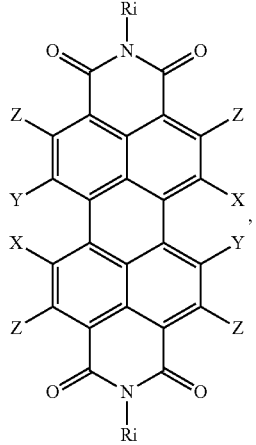

III wherein

X, and Y are the same or different and are, at each occurrence, independently selected from the following electron donating groups (EGD) and electron withdrawing groups (EWD):

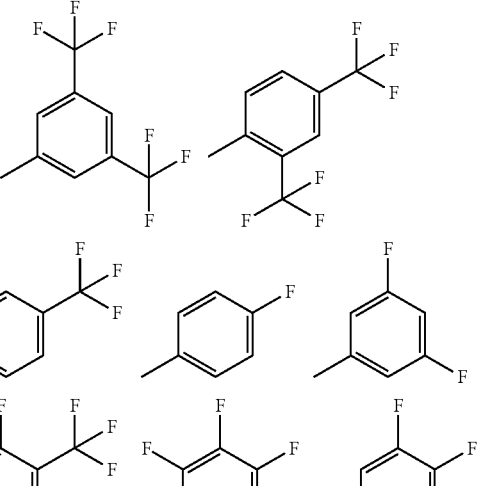

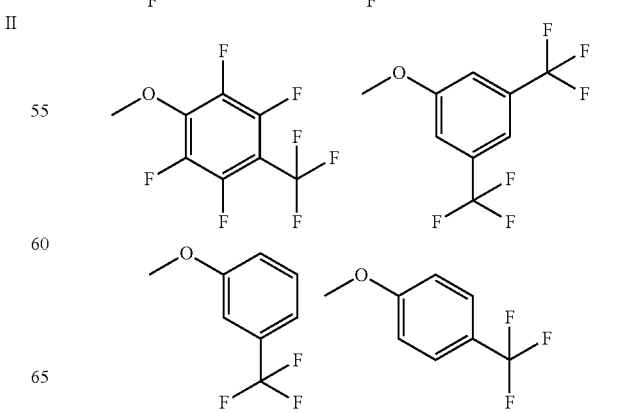

-continued

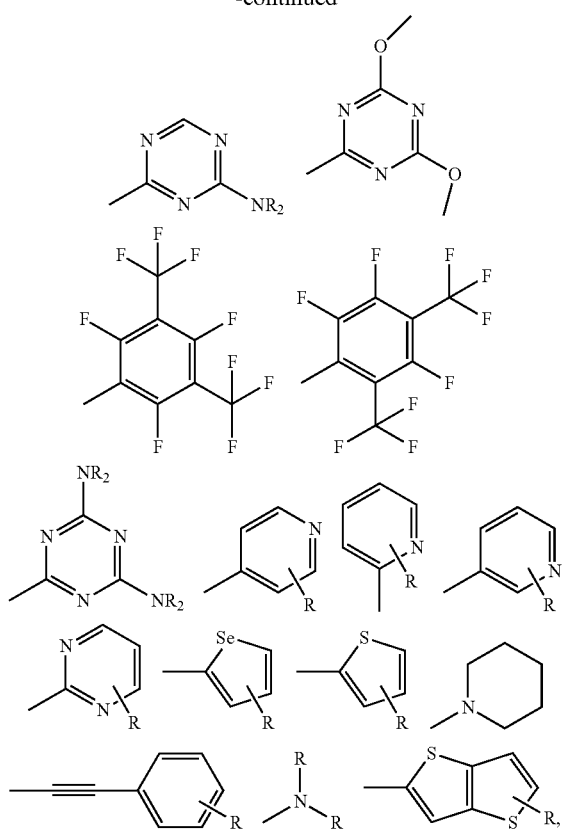

or hydrogen, wherein in formula III, when Y is hydrogen and each X is the same, wherein R is independently selected from hydrogen, an alkyl or aryl substituent, Z, at each occurrence, is independently selected from the following electron donating groups (EGD) and electron accepting groups (EAD):

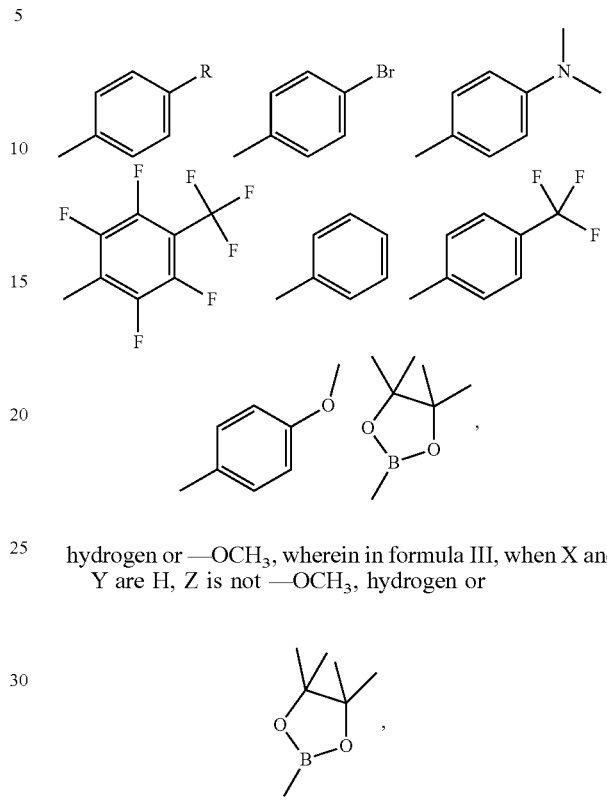

hydrogen or —OCH$_3$, wherein in formula III, when X and Y are H, Z is not —OCH$_3$, hydrogen or W, at each occurrence, is independently selected from the following electron donating groups (EGD) and electron withdrawing groups (EWD):

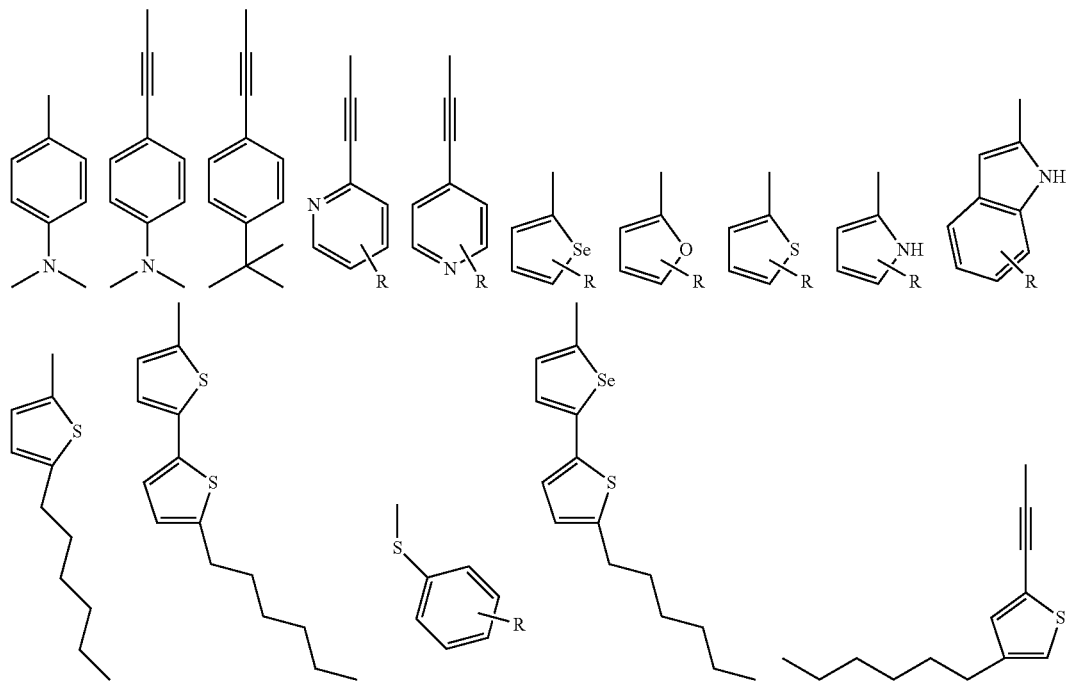

-continued
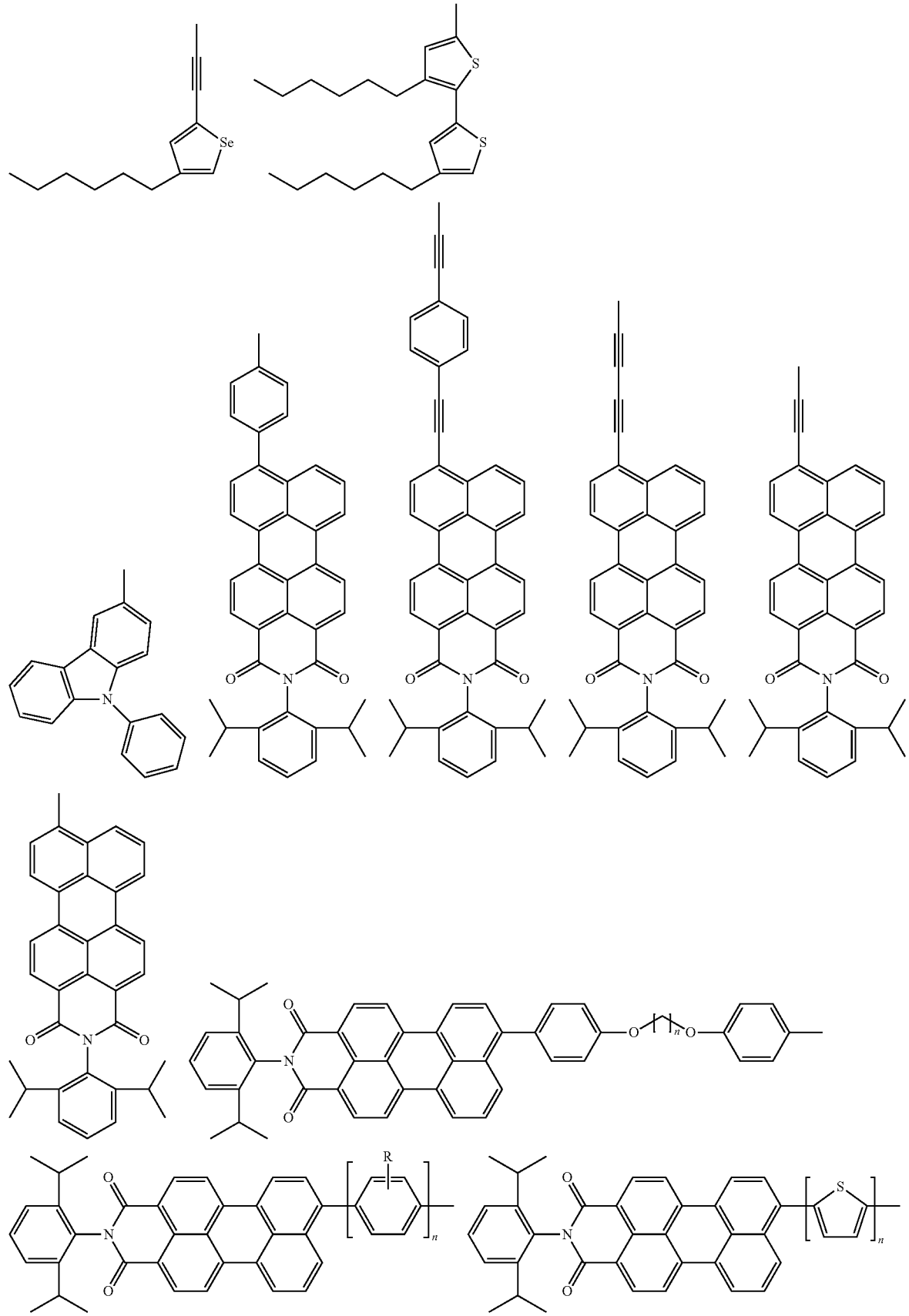
or

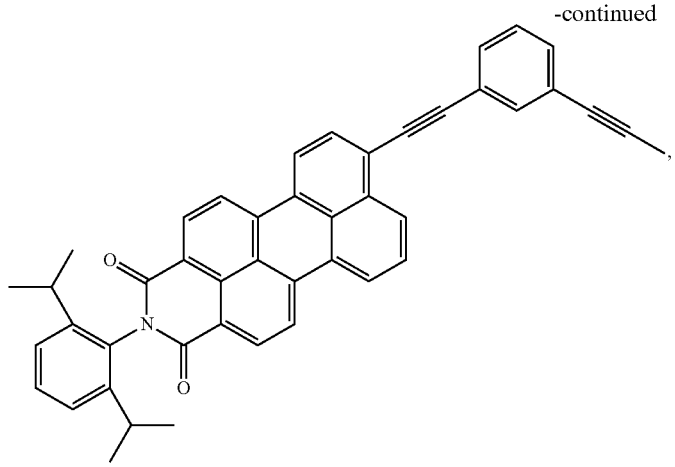

wherein

R is independently selected from hydrogen, an alkyl or aryl substituent, n is an integer selected from 1 to 10, and Ri, at each occurrence, is independently selected from:

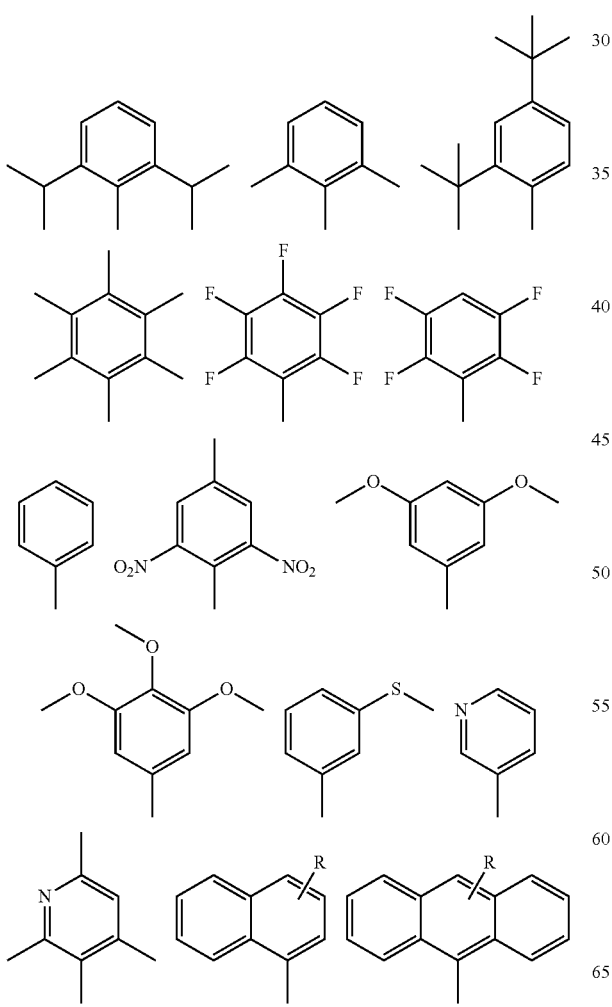

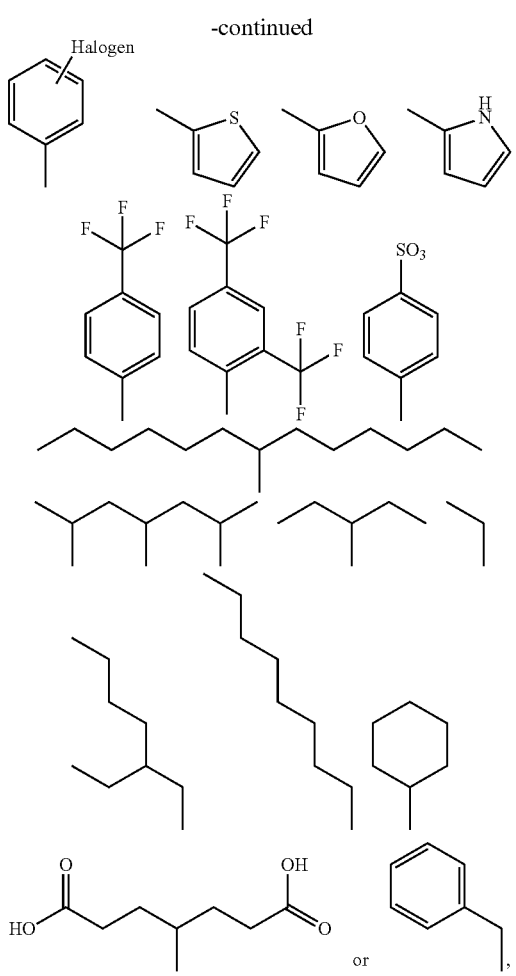

wherein, W, X, and Y are not cyano, nitro, quaternary amino, sulfo, carbonyl, substituted carbonyl, or carboxy.

2. The molecule according to claim 1,
wherein the molecule is represented by formula I, and X, Y and Z are H, and W is as defined in formula I.

3. The molecule according to claim 1, wherein the molecule is represented by formula II and Ri is as defined formula II, X, Y and Z are H, and W is an electron donating group (EDG) as defined in formula II, wherein the molecule is represented by any of the following structures:
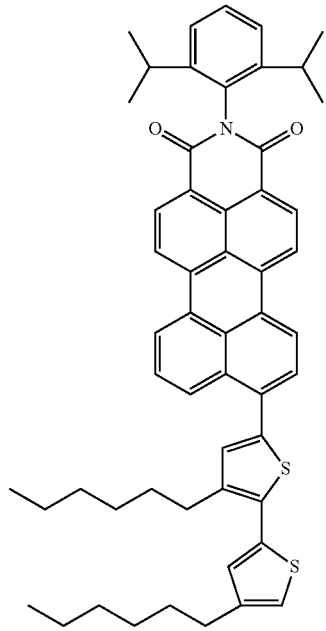
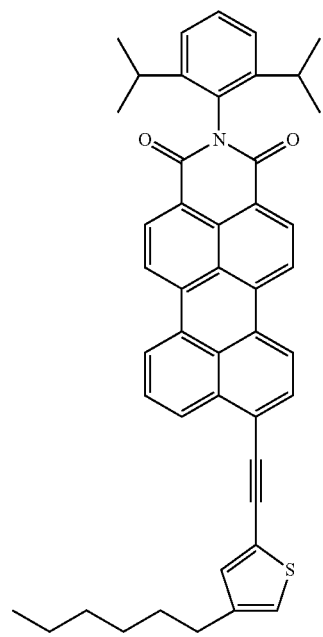
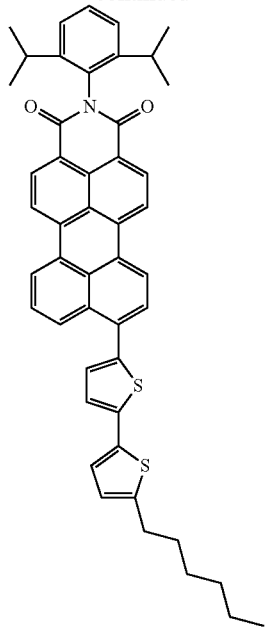
-continued
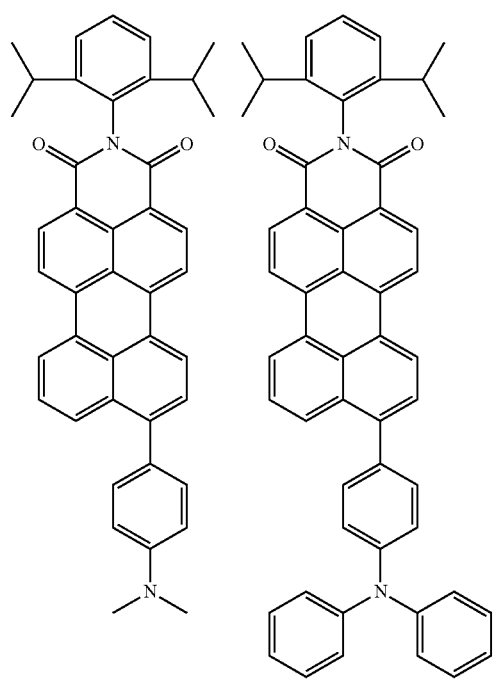

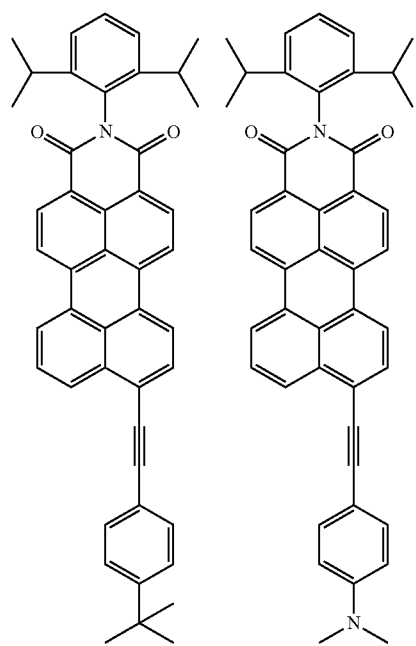
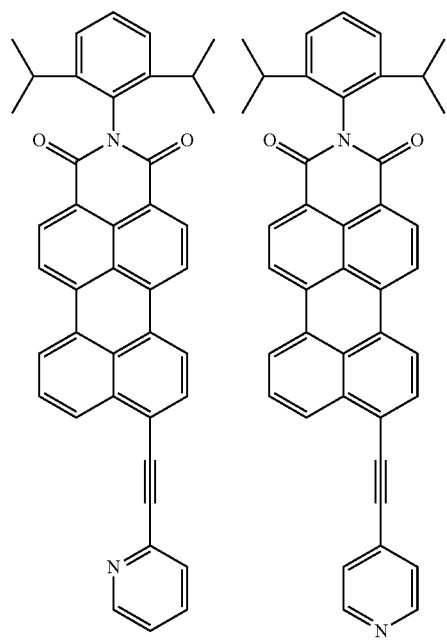
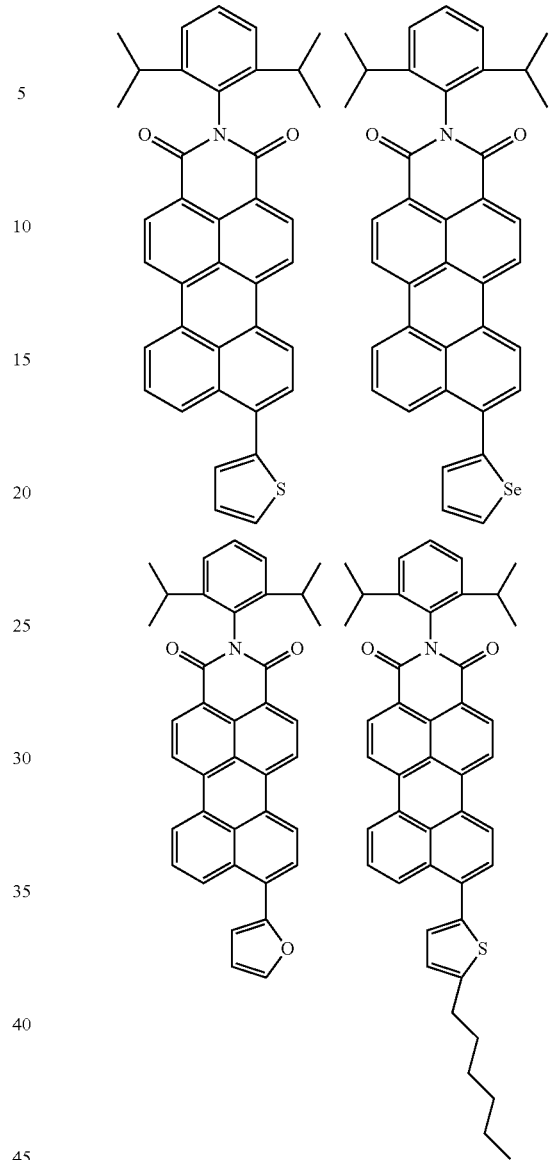
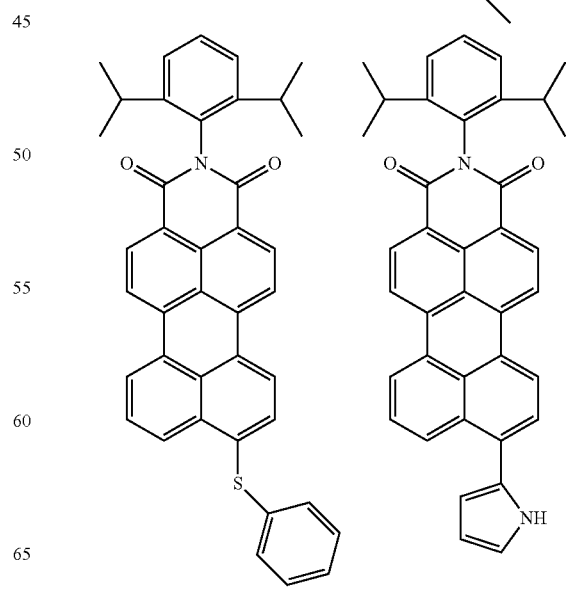

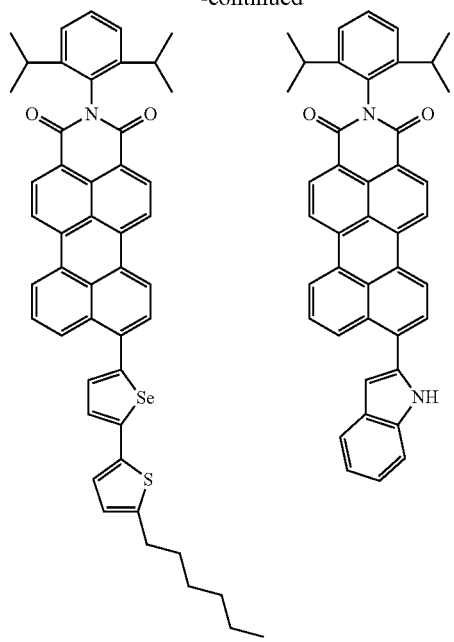
or
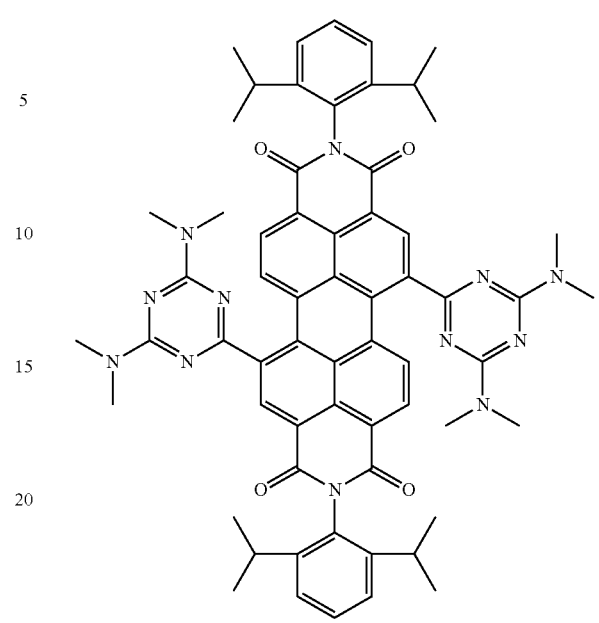
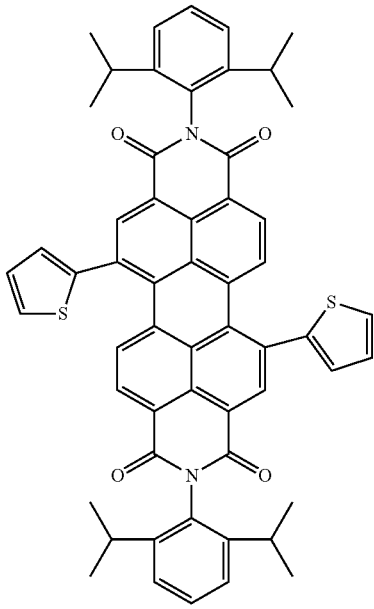
4. The molecule according to claim 1, wherein the molecule is represented by formula III and
Ri is as defined in formula III,
X is electron donating groups (EDG) as defined in formula III,
Y is H and
Z is H,
wherein the molecule is represented by any of the following structures:

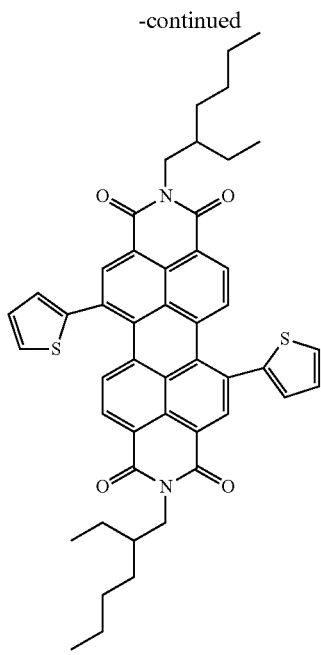

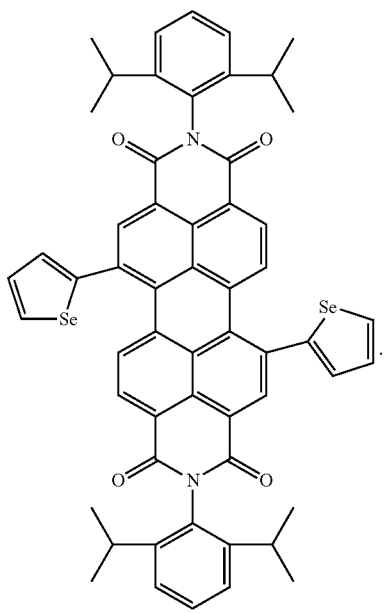

or

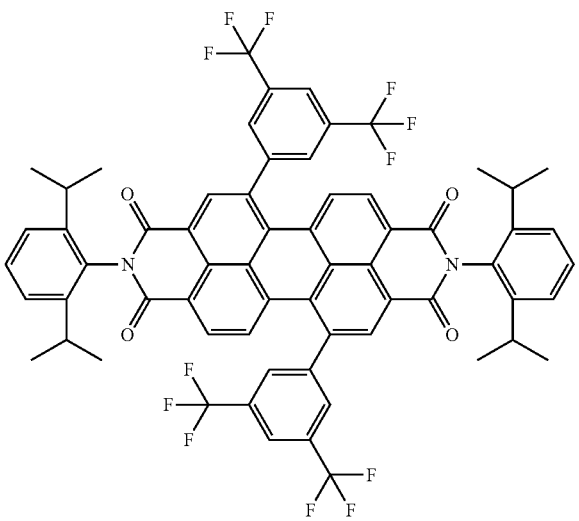

or

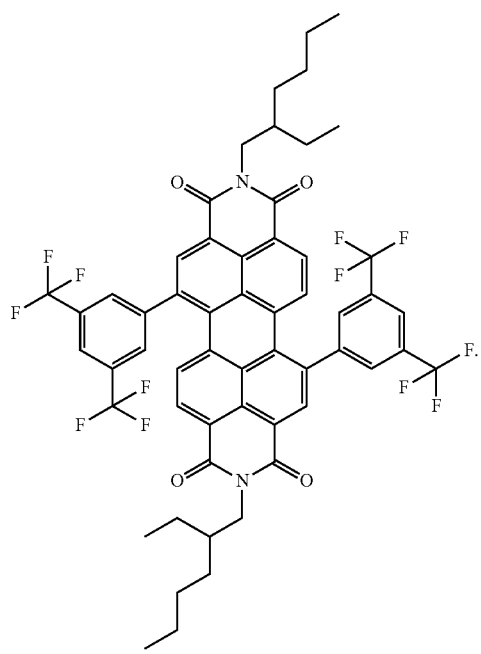

5. The molecule according to claim 1, wherein the molecule is represented by formula III and
Ri is as defined in formula III,
X is electron withdrawing group (EWG) as defined in formula III,
Y is H, and
Z is H,
wherein the molecule is represented by any of the following structures 6. The molecule according to claim 1, wherein the molecule is represented by formula III and
Ri is as defined in formula III,
X and Y are H, and
Z is an electron withdrawing or electron donating group (EWG and EDG) as defined in formula III,
wherein the molecule is represented by any of the following structures:

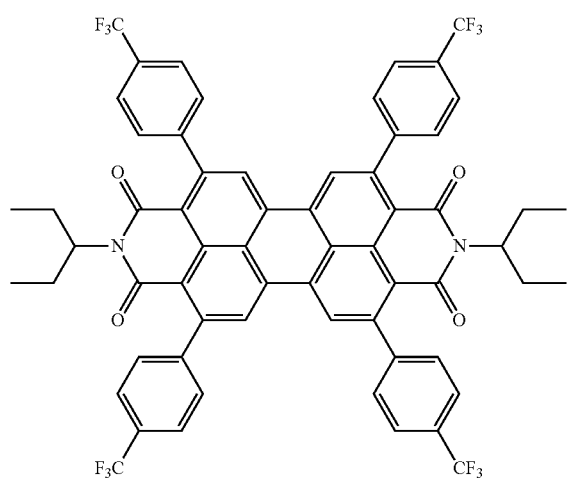
or
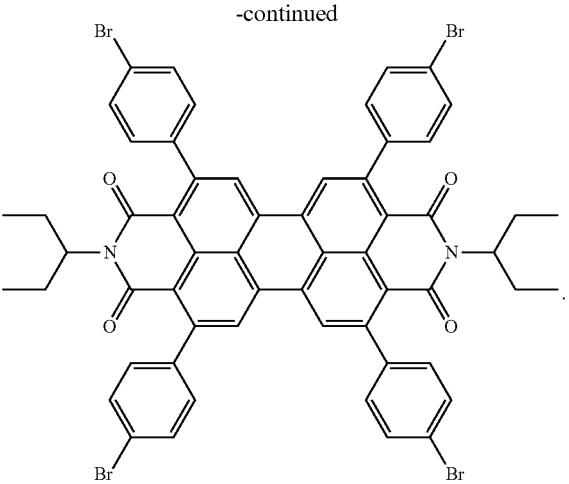
-continued
7. The molecule according to claim 1 represented by any of the following structures:
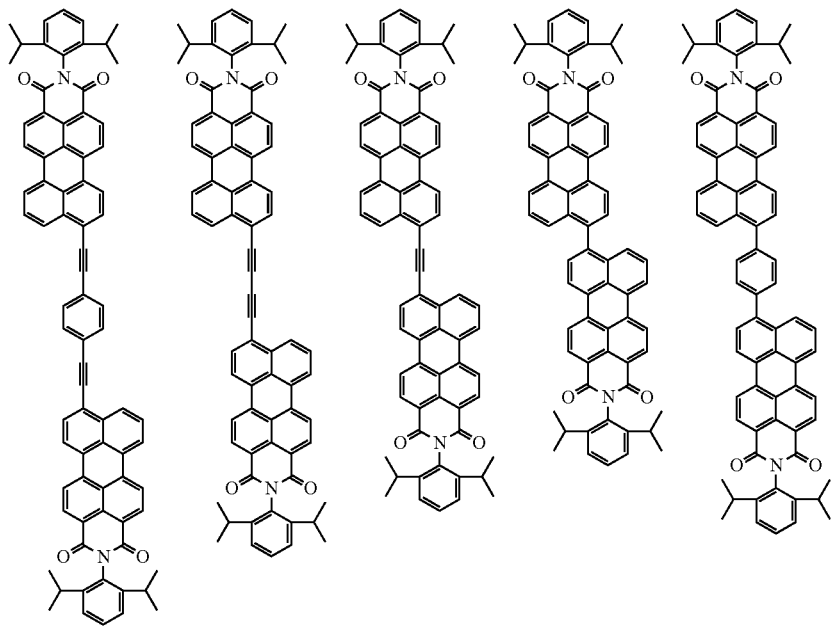
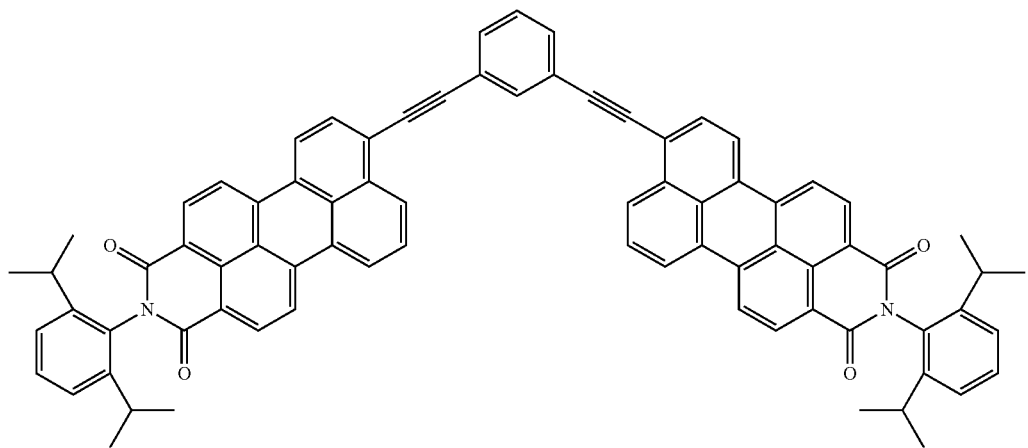

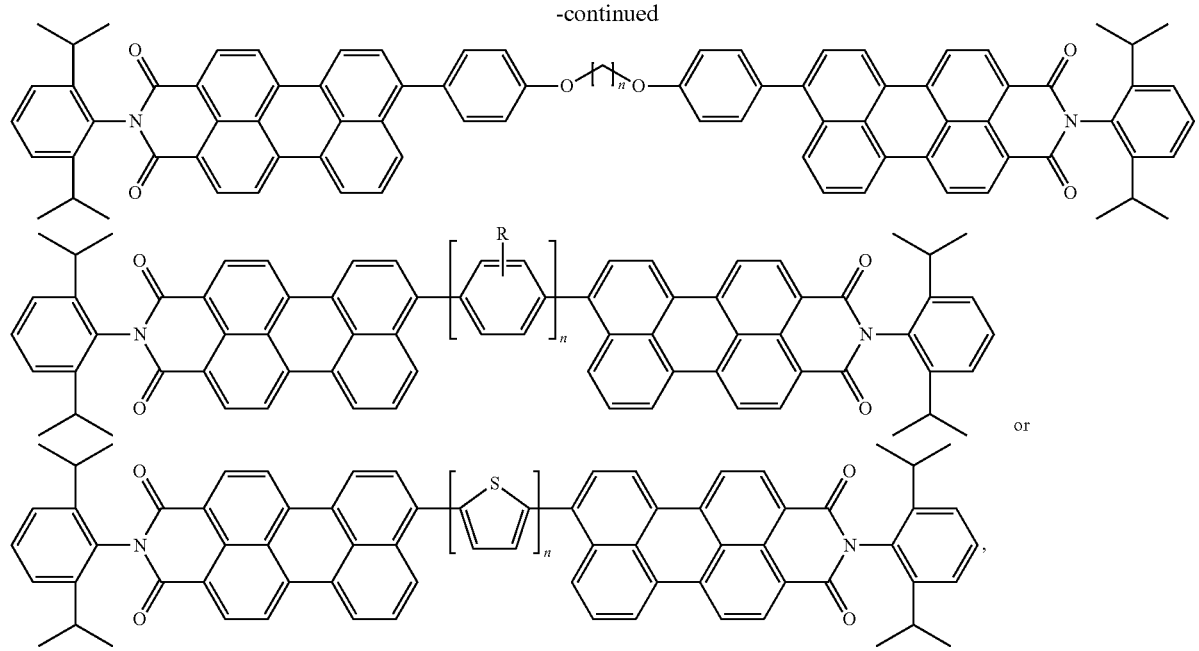

wherein
R is independently selected from hydrogen, an alkyl or aryl substituent, and
n is an integer selected from 1 to 10.

8. The molecule according to claim 1, wherein the molecule exhibits:
absorption in the visible wavelength range about 400 to about 700 nm,
an extinction coefficient of >$10^4$ Lmol$^{-1}$cm$^{-1}$, and/or
high thermal stability, up to at least about 300° C. or up to at least about 300 to 500° C.

9. The molecule according to claim 8, wherein the molecule
exhibits absorption in the wavelength range of visible light, in the range from 400 nm to 700 nm, or a sub-range thereof, 400 nm to 500 nm, or 500 nm to 600 nm, or 600 nm to 700 nm,
absorbs in the blue absorption range or absorbs in the green absorption range or absorbs in the red absorption range, and/or
absorbs less than 20% of the maximum absorption outside of its main range of absorption.

10. An absorption layer and/or a photoelectric conversion layer and/or in an organic and/or hybrid module for optoelectronic application, comprising organic photoelectric conversion layer(s), OLED and OTFT organic modules comprising the molecule according to claim 1.

11. A photoelectric conversion layer comprising a molecule according to claim 1.

12. An absorption layer comprising a molecule according to claim 1.

13. A device comprising a photoelectric conversion layer comprising the molecule according to claim 1,
wherein said device is an organic image sensor, an hybrid image sensor, photodiode, organic photovoltaics, organic light-emitting diode (OLED), or an organic thin-film transistor (OTFT).

14. The device according to claim 13, wherein said photoelectric conversion layer exhibits photo response in the visible absorption range.

15. The device according claim 13, further comprising molecule(s) according to general formula I, II or III or photoelectric conversion layer(s) comprising a molecule according to general formula I, II or III.

16. An organic image sensor, comprising
(a) an organic photoelectric conversion unit comprising photoelectric conversion layer(s) comprising the molecule according to claim 1,
(b) at least one electrode,
(c) a substrate,
(d) a second electrode on top of said photoelectric conversion layer(s).

17. A hybrid silicon-organic image sensor or organic image sensor, comprising
(a) an organic photoelectric conversion unit or units comprising photoelectric conversion layer(s) comprising the molecule according to claim 1,
(b) a Si based photoelectric conversion unit,
(c) metal wiring,
(d) a (CMOS) substrate, and
(e) insulating layer(s).

18. The organic image sensor according to claim 16, wherein said organic photoelectric conversion unit comprises another layer, which may be an n-type material, p-type material, n-buffer layer and/or p-buffer layer or combinations or mixtures thereof.

19. The molecule according to claim 1, wherein, in formula III, Ri is not the following group:

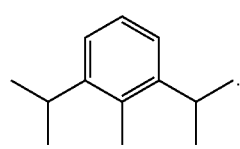

* * * * *